(12) United States Patent
Garcia Rubio et al.

(10) Patent No.: US 8,658,797 B2
(45) Date of Patent: Feb. 25, 2014

(54) ASYMMETRIC UREAS AND MEDICAL USES THEREOF

(75) Inventors: Silvina Garcia Rubio, Princeton, NJ (US); Claudio Giuliano, Como (IT); Claudio Pietra, Como (IT); Zhigang Li, Shanghai (CN)

(73) Assignee: Helsinn Healthcare SA, Lugano/Pazzallo (CH)

( * ) Notice: Subject to any disclaimer, the term of this patent is extended or adjusted under 35 U.S.C. 154(b) by 0 days.

(21) Appl. No.: 13/404,165

(22) Filed: Feb. 24, 2012

(65) Prior Publication Data

US 2012/0220629 A1 Aug. 30, 2012

Related U.S. Application Data

(60) Provisional application No. 61/466,070, filed on Mar. 22, 2011.

(51) Int. Cl.
*C07D 211/56* (2006.01)
*A61K 31/445* (2006.01)

(52) U.S. Cl.
USPC .......................................... 546/224; 514/329

(58) Field of Classification Search
USPC .......................................... 546/224; 514/329
See application file for complete search history.

(56) References Cited

U.S. PATENT DOCUMENTS

| | | | |
|---|---|---|---|
| 6,399,619 B1 | 6/2002 | Berk et al. | |
| 7,534,893 B2 | 5/2009 | Alvaro et al. | |
| 2008/0306055 A1 | 12/2008 | Egner et al. | |

FOREIGN PATENT DOCUMENTS

| | | | |
|---|---|---|---|
| JP | 52085174 | * | 7/1977 |
| WO | WO 95/06635 A1 | | 3/1995 |
| WO | WO 98/06709 A1 | | 2/1998 |
| WO | WO 01-66521 | * | 9/2001 |
| WO | WO 02/070479 A1 | | 9/2002 |
| WO | WO 02/076948 A1 | | 10/2002 |
| WO | WO 03/042205 A1 | | 5/2003 |
| WO | WO 03/080574 A1 | | 10/2003 |
| WO | WO 2004/046110 A1 | | 6/2004 |
| WO | WO 2005/077914 | * | 8/2005 |
| WO | WO 2006/001751 A1 | | 1/2006 |
| WO | WO 2006/014136 A1 | | 2/2006 |
| WO | WO 2009/020960 A1 | | 2/2009 |
| WO | WO 2009/089659 A1 | | 7/2009 |
| WO | WO 2009/092293 A1 | | 7/2009 |

OTHER PUBLICATIONS

Definition of the term adduct—dictionary.com (2012).*
Burrows et al Bioorganic and Medicinal Chemistry Letters 2005, 15, 25-28.*
CAS RN 355401-28-4 (Entered into CAS STN system Sep. 10, 2001).
CAS RN 1290954-39-0 (Entered into CAS STN system May 6, 2011).
CAS RN 1259089-82-1 (Entered into CAS STN system Jan. 12, 2011).
CAS RN 1259199-34-2 (Entered into CAS STN system Jan. 12, 2011).

* cited by examiner

*Primary Examiner* — John Mabry
(74) *Attorney, Agent, or Firm* — Clark G. Sullivan; Troutman Sanders LLP

(57) ABSTRACT

Disclosed are compounds, compositions and methods for the prevention and/or treatment of diseases which are pathophysiologically mediated by the ghrelin receptor. The compounds have the general formula (I):

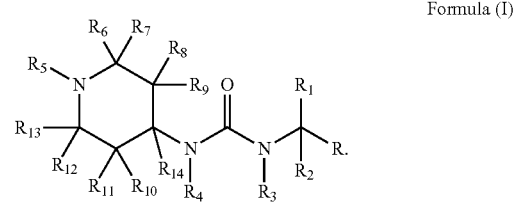

Formula (I)

19 Claims, No Drawings

ASYMMETRIC UREAS AND MEDICAL USES THEREOF

CROSS-REFERENCES TO RELATED APPLICATIONS

This application claims priority under 35 U.S.C. §365(a) to PCT Application No. PCT/CN2011/000298, filed Feb. 25, 2011, and under 35 U.S.C. §119(e) to Provisional U.S. Application No. 61/466,070, filed Mar. 22, 2011. The disclosure of PCT Application No. PCT/CN2011/000298 and U.S. Application No. 61/466,070 are hereby incorporated by reference in their entirety.

FIELD OF THE INVENTION

The present invention relates to novel compounds based on asymmetric ureas, and medical uses thereof, particularly in the treatment of medical conditions modulated by the ghrelin receptor.

BACKGROUND

The growth hormone secretagogue receptor (GHS-R) regulates a number of physiological processes, including growth hormone (GH) release, metabolism, and appetite. Ghrelin, a circulating hormone produced predominantly by endocrine cells in the stomach, is its endogenous ligand. Ghrelin is a 28 amino acid peptide with an acyl side chain required for biological activity (Kojima et al., Nature, 402, 656-660, 1999). Ghrelin has been shown to stimulate growth hormone (GH) release and to increase food intake when administered both centrally and peripherally (Wren et al., Endocrinology, 141, 4325-4328, 2000).

Endogenous levels of ghrelin rise on fasting and fall on re-feeding in humans (Cummings et al., Diabetes, 50, 1714-1719, 2001). Ghrelin also appears to play a role in maintaining long term energy balance and appetite regulation. Chronic administration of ghrelin in rodents leads to hyperphagia and weight gain that are independent of growth hormone secretion (Tschop et al., Nature, 407, 908-913, 2000). Circulating ghrelin levels decrease in response to chronic overfeeding and increase in response to chronic negative energy balance associated with anorexia or exercise. Obese people generally have low plasma ghrelin levels (Tschop et al., Diabetes, 50, 707-709, 2001) accordingly to the physiological response of the body in reducing calories intake. Intravenous ghrelin is effective in stimulating food intake in humans. A recent study showed a 28% food intake increase from a buffet meal with a ghrelin infusion compared with saline control (Wren et al., J Clin Endocrinology and Metabolism, 86, 5992, 2001).

In view of the above experimental evidence, compounds that modulate ghrelin receptor activity have been proposed for preventing and/or treating disorders associated with ghrelin receptor physiology. For example, antagonists at ghrelin receptor may reduce appetite, reduce food intake, induce weight loss and treat obesity without affecting or reducing the circulating growth hormone levels. On the other hand, agonists at ghrelin receptor may be useful in stimulating food intake and thus be useful in treating eating disorders, for example anorexia nervosa, or in treating cachexia resulting from cancer, AIDS or Chronic Obstructive Pulmonary Disease (COPD). Ghrelin agonists may also be useful as gastroprokinetic agents which can enhance gastrointestinal motility by increasing the frequency of contractions in the small intestine or making them stronger, but without disrupting their rhythm. Gastroprokinetic agents are used to relieve gastrointestinal symptoms such as abdominal discomfort, bloating, constipation, heart burn, nausea, and vomiting, and are used to treat a number of gastrointestinal disorders, including but not limiting to, irritable bowel syndrome, gastritis, acid reflux disease, gastroparesis, and functional dyspepsia. Furthermore, compounds that modulate ghrelin receptor activity can also be used to prevent or treat diseases related to substance abuse, for example, alcohol or drug (e.g., amphetamines, barbiturates, benzodiazepines, cocaine, methaqualone, and opioids) abuse, which refers to a maladaptive pattern of use of a substance that is not considered dependent.

A number of compounds acting on the ghrelin receptor have been reported in the literature. YIL-781, for example, is a small molecule ghrelin receptor antagonist from Bayer that reportedly improves glucose tolerance, suppress appetite and promote weigh loss (Esler et al., Endocrinology 148 (11): 5175-5185); LY444711 is an orally active ghrelin receptor agonist from Lilly that reportedly induces adiposity by stimulating food consumption and sparing fat utilization (Bioorg. & Med. Chem. Lett., 2004, 14, 5873-5876); Anamorelin is an orally available ghrelin receptor small molecule agonist from Helsinn Therapeutics that is in clinical trials for the treatment of anorexia and cachexia in cancer patients. Other small molecule ghrelin receptor modulators can be found in WO 2008/092681, US 2009/0253673, WO 2008/148853, WO 2008/148856, US 2007/0270473 and US 2009/0186870.

In view of the above, it is desirable to find new compounds which modulate ghrelin receptor activity with enhanced efficacy and fewer undesirable side effects.

SUMMARY

In view of the foregoing, the inventors have developed a novel class of compounds particularly well-suited for modulating the ghrelin receptor and having the general formula (I):

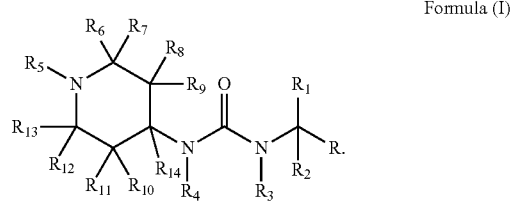

Formula (I)

with R and $R_1$-$R_{14}$ as defined herein, and pharmaceutically acceptable salts or adducts thereof Compounds of formula (I), also known as asymmetric ureas, are particularly useful for preventing and/or treating diseases that are pathophysiologically related to the ghrelin receptor in a subject. Accordingly, in another embodiment the invention provides a method of treating a disease that is mediated by the ghrelin receptor, comprising administering to said subject a therapeutically effective amount of a compound of formula (I), or a pharmaceutically acceptable salt or adduct thereof.

Also disclosed are pharmaceutical compositions for preventing and/or treating diseases which are pathophysiologically related to ghrelin receptor in a subject, comprising a therapeutically effective amount of a compound of formula (I), or a pharmaceutically acceptable salt or adduct thereof, and one or more pharmaceutically acceptable excipients.

DETAILED DESCRIPTION

Before the present compounds, compositions, articles, devices, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular embodiments only and is not intended to be limiting.

Materials

A. Compounds

Disclosed are compounds, and pharmaceutically acceptable salts or adducts thereof, represented by formula (I):

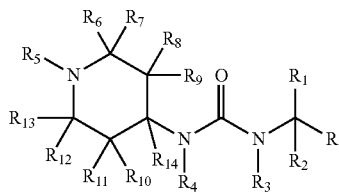

Formula (I)

wherein:

R is selected from the group consisting of aryl, arylalkyl, carbocyclic ring, heterocycloalkyl, heterocycloalkylalkyl, heteroaryl and heteroarylalkyl, optionally substituted with one or more independent $R^{103}$ substituents;

$R_1$ is selected from the group consisting of hydrogen, hydroxy, hydroxyalkyl, amino, alkyl, alkenyl, cycloalkyl, halogen, alkoxy, alkoxyalkyl, —C(O)$R^{101}$, —C(O)O$R^{101}$, aryl, arylalkyl, heterocycloalkyl, heterocycloalkylalkyl, heteroaryl and heteroarylalkyl, each optionally independently substituted with one or more independent $R^{103}$ substituents;

$R_2$ is hydrogen or $R_1$ and $R_2$, together with the atoms connecting the same, form a fused or non-fused mono, bicyclic or tricyclic heterocyclic or carbocyclic ring which is optionally independently substituted with one or more $R^{103}$ substituents;

$R_3$ is selected from the group consisting of hydrogen, alkyl, alkenyl, cycloalkyl, aryl, arylalkyl, heterocycloalkyl, heterocycloalkylalkyl, heteroaryl, heteroarylalkyl, —C(O)$R^{101}$, —C(O)O$R^{101}$, —C(O)N$R^{101}R^{102}$, —S(O)$_2R^{102}$, —S$R^{101}$ and —S(O)$_2$N$R^{101}$N$R^{102}$, optionally substituted with one or more independent $R^{103}$ substituents;

$R_4$ is selected from the group consisting of alkyl, alkenyl, cycloalkyl, aryl, arylalkyl, heterocycloalkyl, heterocycloalkylalkyl, heteroaryl, heteroarylalkyl, —O$R^{103}$, N$R^{101}R^{102}$, —C(O)$R^{101}$, —C(O)O$R^{101}$, —C(O)N$R^{101}R^{102}$, -alkylN$R^{101}R^{102}$, —S(O)$_2R^{102}$, —S$R^{101}$ and —S(O)$_2$N$R^{101}R^{102}$, optionally substituted with one or more independent $R^{103}$ substituents; or $R_3$ and $R_4$, together with the atoms connecting $R_3$ and $R_4$, form a fused or non-fused mono, bicyclic or tricyclic heterocyclic or carbocyclic ring which is optionally independently substituted with one or more $R^{103}$ substituents;

$R_5$ is selected from the group consisting of alkyl, alkenyl, cycloalkyl, aryl, arylalkyl, heterocycloalkyl, heteroaryl, heteroarylalkyl, oxide (=O), —C(O)$R^{101}$, —C(O)O$R^{101}$, —C(O)N$R^{101}R^{102}$, —S(O)$_2R^{102}$, —S$R^{101}$ and —S(O)$_2$N$R^{101}R^{102}$;

$R_6$, $R_7$, $R_8$, $R_9$, $R_{10}$, $R_{11}$, $R_{12}$, $R_{13}$ and $R_{14}$ are each independently selected from the group consisting of hydrogen, cyano, —NO$_2$, —O$R^{101}$, hydroxy, amino, alkyl, alkenyl, cycloalkyl, halogen, alkoxy, alkoxyalkyl, aryl, arylalkyl, heterocycloalkyl, heterocycloalkylalkyl, heteroaryl, heteroarylalkyl, —C(O)$R^{101}$, —C(O)O$R^{101}$, —C(O)N$R^{101}R^{102}$, N$R^{101}R^{102}$, —N$R^{101}$S(O)$_2R^{102}$, —N$R^{101}$C(O)$R^{102}$, —S(O)$_2R^{102}$, —S$R^{101}$ and —S(O)$_2$N$R^{101}R^{102}$, each optionally independently substituted with one or more independent $R^{103}$ substituents; or any two or more substituents selected from the group consisting of $R_6$, $R_7$, $R_8$, $R_9$, $R_{10}$, $R_{11}$, $R_{12}$, $R_{13}$ and $R_{14}$ together with the atoms connecting the same, form a fused or non-fused mono, bicyclic or tricyclic heterocyclic or carbocyclic ring which is optionally independently substituted with one or more $R^{103}$ substituents; and $R^{101}$, $R^{102}$ and $R^{103}$ are each independently selected from the group consisting of hydrogen, cyano, —NO$_2$, hydroxy, amino, alkyl, alkenyl, cycloalkyl, halogen, alkoxy, alkoxyalkyl, aryl, arylalkyl, heterocycloalkyl, heterocycloalkylalkyl, heteroaryl, heteroarylalkyl, —C(O)$R^{104}$, —C(O)O$R^{104}$, —C(O)N$R^{104}R^{105}$, —N$R^{104}R^{105}$, —N$R^{104}$S(O)$_2R^{105}$, —N$R^{104}$C(O)$R^{105}$, —S(O)$_2R^{104}$, —S$R^{104}$ and —S(O)$_2$N$R^{104}R^{105}$, each optionally independently substituted with one or more independent $R^{103}$ substituents; or $R^{101}$, $R^{102}$, together with the atoms connecting the same, form a fused or non-fused mono, bicyclic or tricyclic heterocyclic or carbocyclic ring which is optionally independently substituted with one or more $R^{103}$ substituents; and $R^{104}$ and $R^{105}$ are each independently selected from the group consisting of hydrogen, cyano, —NO$_2$, hydroxy, hydroxyalkyl, amino, alkyl, alkenyl, cycloalkyl, halogen, alkoxy, alkoxyalkyl, aryl, arylalkyl, heterocycloalkyl, heterocycloalkylalkyl, heteroaryl and heteroarylalkyl.

In some forms, the compounds as presently disclosed are compounds of formula (I), or pharmaceutically acceptable salts or adducts thereof, wherein R is aryl or heteroaryl. In some other forms, the compounds as presently disclosed are compounds of formula (I), or pharmaceutically acceptable salts or adducts thereof, wherein R is R is selected from the group consisting of phenyl, naphthalene, tetrahydronaphthalenyl, indenyl, isoindenyl, indanyl, anthracenyl, phenanthrenyl, benzonaphthenyl, fluorenyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl, which is optionally independently substituted with from one to six substituents independently selected from the group consisting of hydrogen, halogen, alkoxy, haloalkyl, cyano, —NO$_2$, —O$R^{101}$, hydroxy, amino, alkyl, alkenyl, cycloalkyl, aryl, arylalkyl, heterocycloalkyl, heterocycloalkylalkyl, heteroaryl, heteroarylalkyl, —C(O)$R^{101}$, —C(O)O$R^{101}$, —C(O)N$R^{101}R^{102}$, —N$R^{101}R^{102}$, —N$R^{101}$S(O)$_2R^{102}$, —N$R^{101}$C(O)$R^{102}$, —S(O)$_2R^{102}$, —S$R^{101}$ and —S(O)$_2$N$R^{101}R^{102}$.

In some forms, the compounds as presently disclosed are compounds of formula (I), or pharmaceutically acceptable salts or adducts thereof, wherein R is phenyl or naphthalene which is optionally independently substituted with from one to six substituents independently selected from the group consisting of hydrogen, chloro, fluoro, bromo, trifluoromethyl, cyano, methoxy, ethoxy, methyl and ethyl.

In some forms, the compounds as presently disclosed are compounds of formula (I), or pharmaceutically acceptable salts or adducts thereof, wherein $R_1$ is selected from the group consisting of hydrogen, alkoxy, alkoxyalkyl, —O$R^{101}$, hydroxy, hydroxyalkyl, amino, alkyl, alkenyl, cycloalkyl, aryl, arylalkyl, heterocycloalkyl, heterocycloalkylalkyl, heteroaryl and heteroarylalkyl. In some other forms, the compounds as presently disclosed are compounds of formula (I), or pharmaceutically acceptable salts or adducts thereof, wherein $R_1$ is selected from the group consisting of alkyl, cycloalkyl, hydroxyalkyl, alkoxyalkyl, arylalkyl and heteroarylalkyl. In some other forms, the compounds as presently disclosed are compounds of formula (I), or pharmaceutically acceptable salts or adducts thereof, wherein $R_1$ is selected from the group consisting of methyl, —$CH_2OH$, and —$CH_2$—O—$CH_2$-phenyl.

In some other forms, the compounds as presently disclosed are compounds of formula (I), or pharmaceutically acceptable salts or adducts thereof, wherein $R_3$ is hydrogen, alkyl or cycloalkyl.

In some forms, the compounds as presently disclosed are compounds of formula (I), or pharmaceutically acceptable salts or adducts thereof, wherein $R_4$ is selected from the group consisting of alkyl, cycloalkyl, hydroxy, amino, alkoxy, alkylamino, aryl, arylalkyl, heterocycloalkyl, heterocycloalkylalkyl, heteroaryl, heteroarylalkyl and aminoalkyl. In some other forms, the compounds as presently disclosed are compounds of formula (I), or pharmaceutically acceptable salts or adducts thereof, wherein $R_4$ is methyl, ethyl, benzyl, or benzyl substituted with from one to five substituents independently selected from the group consisting of methyl, fluoro, chloro, trifluoromethyl, methoxy, cyano and hydroxy.

In some forms, the compounds as presently disclosed are compounds of formula (I), or pharmaceutically acceptable salts or adducts thereof, wherein $R_5$ is selected from the group consisting of alkyl, cycloalkyl, oxide (=O), aryl, arylalkyl, heterocycloalkyl, heterocycloalkylalkyl, heteroaryl, heteroarylalkyl, —$C(O)R^{101}$, —$C(O)OR^{101}$ and —$C(O)NR^{101}R^{102}$. In some other forms, the compounds as presently disclosed are compounds of formula (I), or pharmaceutically acceptable salts or adducts thereof, wherein $R_5$ is methyl.

In some forms, the compounds as presently disclosed are compounds of formula (I), or pharmaceutically acceptable salts or adducts thereof, wherein $R_6$, $R_7$, $R_8$, $R_9$, $R_{10}$, $R_{11}$, $R_{12}$, $R_{13}$ and $R_{14}$ are each independently selected from the group consisting of hydrogen, alkyl, cycloalkyl, —$C(O)OR^{101}$, and -alkyl$OR^{103}$. In some other forms, the compounds as presently disclosed are compounds of formula (I), or pharmaceutically acceptable salts or adducts thereof, wherein $R_8$ and $R_9$ are each independently hydrogen, alkyl, cycloalkyl, —$C(O)OR^{101}$, or -alkyl$OR^{103}$. In some other forms, the compounds as presently disclosed are compounds of formula (I), or pharmaceutically acceptable salts or adducts thereof, wherein $R_8$ and $R_9$ are each independently hydrogen, methyl, ethyl, —$C(=O)OEt$, or —$CH_2OH$. In some other forms, the compounds as presently disclosed are compounds of formula (I), or pharmaceutically acceptable salts or adducts thereof, wherein $R_8$ and $R_9$, together with the atom connecting them, form a cycloalkyl ring. In some forms, the compounds as presently disclosed are compounds of formula (I), or pharmaceutically acceptable salts or adducts thereof, wherein said cycloalkyl ring as formed by $R_8$ and $R_9$ together with the atom connecting them, is cyclopropane.

In some forms, the compounds as presently disclosed are compounds of formula (I), or pharmaceutically acceptable salts or adducts thereof, wherein the compound of formula (I) is a compound selected from the group consisting of:

| Compound No. | Chemical Structure | Chemical Name |
|---|---|---|
| GA1 | 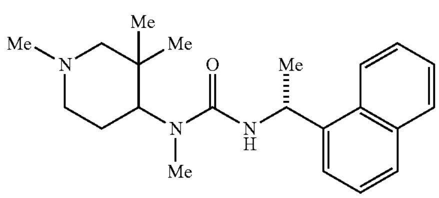 [SMILES: C[C@@H](NC(=O)N(C)C1CCN(C)CC1(C)C)c1cccc2ccccc12] | 1-methyl-3-((R)-1-(naphthalen-1-yl)ethyl)-1-(1,3,3-trimethylpiperidin-4-yl)urea, |
| GA2 | 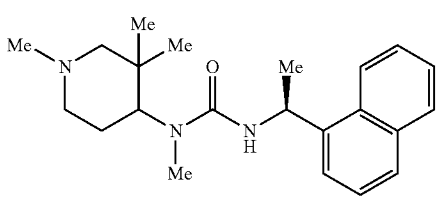 [SMILES: C[C@H](NC(=O)N(C)C1CCN(C)CC1(C)C)c1cccc2ccccc12] | 1-methyl-3-((S)-1-(naphthalen-1-yl)ethyl)-1-(1,3,3-trimethylpiperidin-4-yl)urea, |
| GA3 | 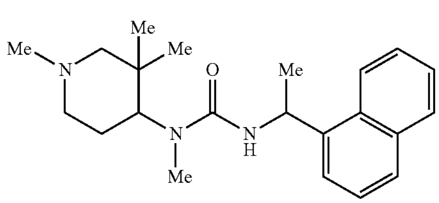 [SMILES: CC(NC(=O)N(C)C1CCN(C)CC1(C)C)c1cccc2ccccc12] | 1-methyl-3-(1-(naphthalen-1-yl)ethyl)-1-(1,3,3-trimethylpiperidin-4-yl)urea, |

-continued

| Compound No. | Chemical Structure | Chemical Name |
|---|---|---|
| GA4 | 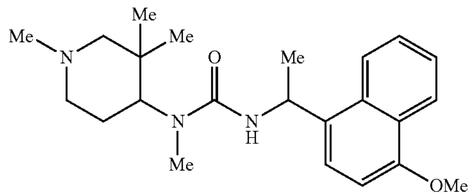 [SMILES: COc1ccc(C(C)NC(=O)N(C)C2CCN(C)CC2(C)C)c2ccccc12] | 3-(1-(4-methoxynaphthalen-1-yl)ethyl)-1-methyl-1-(1,3,3-trimethylpiperidin-4-yl)urea, |
| GA5 | 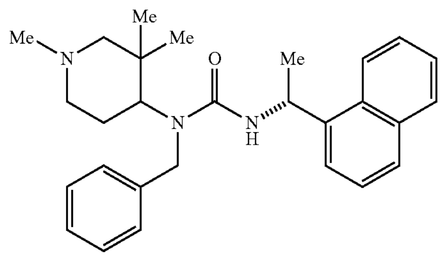 | 1-benzyl-3-((R)-1-(naphthalen-1-yl)ethyl)-1-(1,3,3-trimethylpiperidin-4-yl)urea, |
| GA6 | 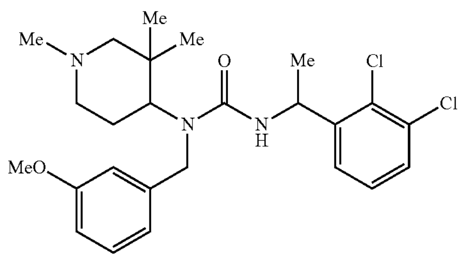 | 3-(1-(2,3-dichlorophenyl)ethyl)-1-(3-methoxybenzyl)-1-(1,3,3-trimethylpiperidin-4-yl)urea, |
| GA7 | 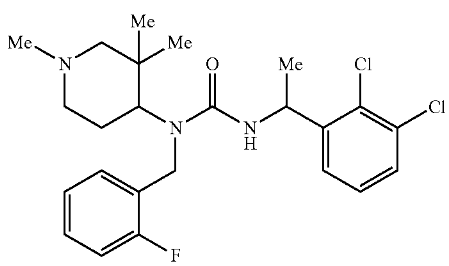 [SMILES: CC(NC(=O)N(Cc1ccccc1F)C1CCN(C)CC1(C)C)c1cccc(Cl)c1Cl] | 3-(1-(2,3-dichlorophenyl)ethyl)-1-(2-fluorobenzyl)-1-(1,3,3-trimethylpiperidin-4-yl)urea, |
| GA8 | 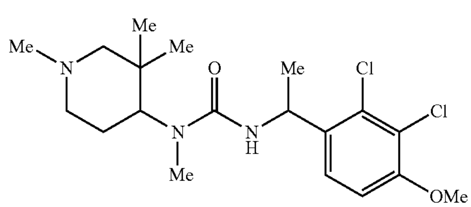 [SMILES: COc1ccc(C(C)NC(=O)N(C)C2CCN(C)CC2(C)C)c(Cl)c1Cl] | 3-(1-(2,3-dichloro-4-methoxyphenyl)ethyl)-1-methyl-1-(1,3,3-trimethylpiperidin-4-yl)urea, |
| GA9 | 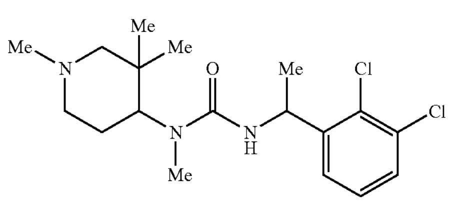 | 3-(1-(2,3-dichlorophenyl)ethyl)-1-methyl-1-(1,3,3-trimethylpiperidin-4-yl)urea, |

-continued

| Compound No. | Chemical Structure | Chemical Name |
|---|---|---|
| GA10 | 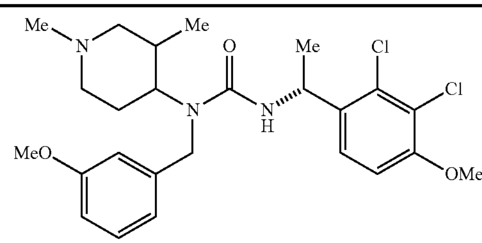 | 3-((R)-1-(2,3-dichloro-4-methoxyphenyl)ethyl)-1-(1,3-dimethylpiperidin-4-yl)-1-(3-methoxybenzyl)urea, |
| GA11 | 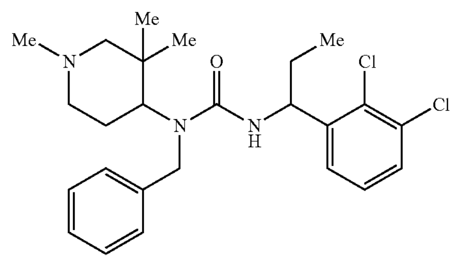 [SMILES: CCC(NC(=O)N(Cc1ccccc1)C1CCN(C)CC1(C)C)c1cccc(Cl)c1Cl] | 1-benzyl-3-(1-(2,3-dichlorophenyl)propyl)-1-(1,3,3-trimethylpiperidin-4-yl)urea, |
| GA12 | 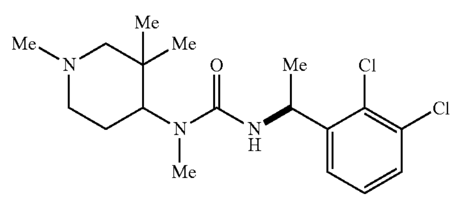 | 3-((S)-1-(2,3-dichlorophenyl)ethyl)-1-methyl-1-(1,3,3-trimethylpiperidin-4-yl)urea, |
| GA13 | 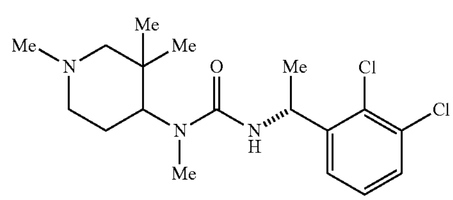 | 3-((R)-1-(2,3-dichlorophenyl)ethyl)-1-methyl-1-(1,3,3-trimethylpiperidin-4-yl)urea, |
| GA14 | 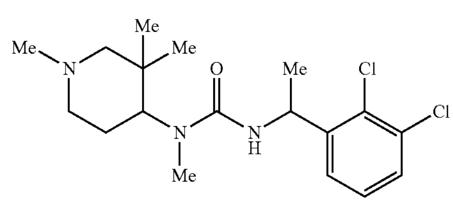 [SMILES: CC(NC(=O)N(C)C1CCN(C)CC1(C)C)c1cccc(Cl)c1Cl] | 3-(1-(2,3-dichlorophenyl)ethyl)-1-methyl-1-(1,3,3-trimethylpiperidin-4-yl)urea, |
| GA15 | 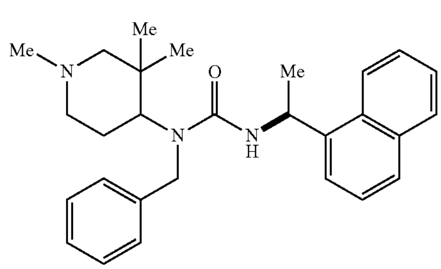 | 1-benzyl-3-((S)-1-(naphthalen-1-yl)ethyl)-1-(1,3,3-trimethylpiperidin-4-yl)urea, |

-continued

| Compound No. | Chemical Structure | Chemical Name |
|---|---|---|
| GA16 | 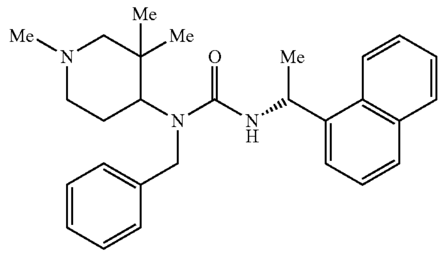 | 1-benzyl-3-((R)-1-(naphthalen-1-yl)ethyl)-1-(1,3,3-trimethylpiperidin-4-yl)urea, |
| GA17 | 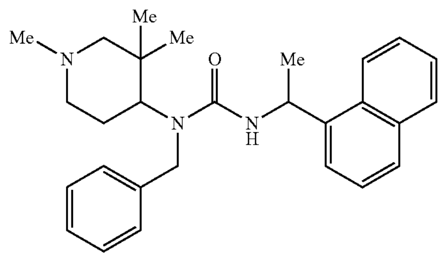 | 1-benzyl-3-(1-(naphthalen-1-yl)ethyl)-1-(1,3,3-trimethylpiperidin-4-yl)urea, |
| GA18 | 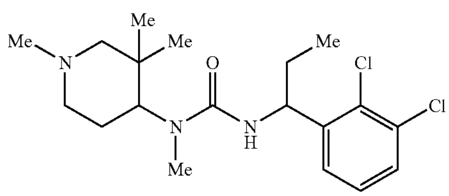 [SMILES: CCC(NC(=O)N(C)C1CCN(C)CC1(C)C)c1cccc(Cl)c1Cl] | 3-(1-(2,3-dichlorophenyl)propyl)-1-methyl-1-(1,3,3-trimethylpiperidin-4-yl)urea, |
| GA19 | 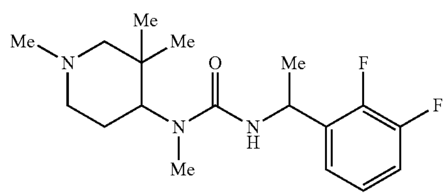 [SMILES: CC(NC(=O)N(C)C1CCN(C)CC1(C)C)c1cccc(F)c1F] | 3-(1-(2,3-difluorophenyl)ethyl)-1-methyl-1-(1,3,3-trimethylpiperidin-4-yl)urea, |
| GA20 | 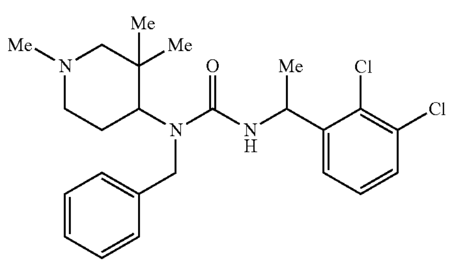 [SMILES: CC(NC(=O)N(Cc1ccccc1)C1CCN(C)CC1(C)C)c1cccc(Cl)c1Cl] | 1-benzyl-3-(1-(2,3-dichlorophenyl)ethyl)-1-(1,3,3-trimethylpiperidin-4-yl)urea, |
| GA21 | 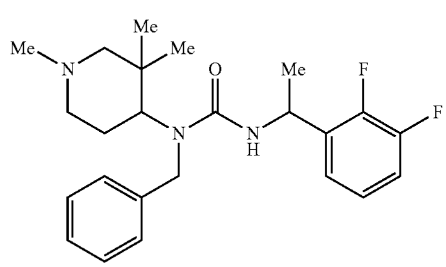 [SMILES: CC(NC(=O)N(Cc1ccccc1)C1CCN(C)CC1(C)C)c1cccc(F)c1F] | 1-benzyl-3-(1-(2,3-difluorophenyl)ethyl)-1-(1,3,3-trimethylpiperidin-4-yl)urea, |

-continued

| Compound No. | Chemical Structure | Chemical Name |
|---|---|---|
| GA22 | 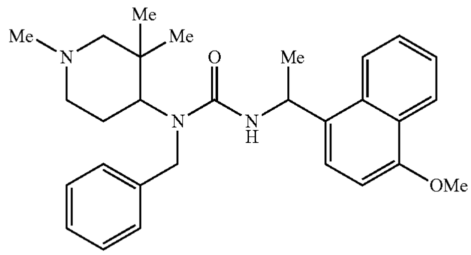 [SMILES: COc1ccc(C(C)NC(=O)N(Cc2ccccc2)C2CCN(C)CC2(C)C)c2ccccc12] | 1-benzyl-3-(1-(4-methoxynaphthalen-1-yl)ethyl)-1-(1,3,3-trimethylpiperidin-4-yl)urea, |
| GA23 | 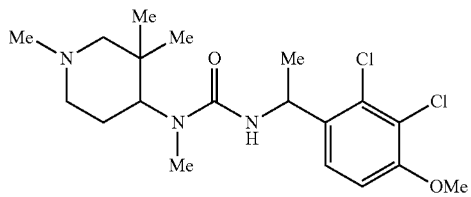 [SMILES: COc1ccc(C(C)NC(=O)N(C)C2CCN(C)CC2(C)C)c(Cl)c1Cl] | 3-(1-(2,3-dichloro-4-methoxyphenyl)ethyl)-1-methyl-1-(1,3,3-trimethylpiperidin-4-yl)urea, |
| GA24 | 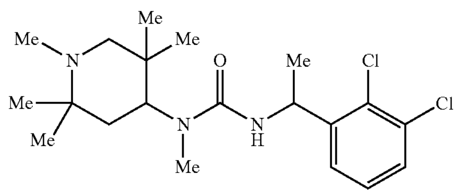 [SMILES: CC(NC(=O)N(C)C1CC(C)(C)N(C)CC1(C)C)c1cccc(Cl)c1Cl] | 3-(1-(2,3-dichlorophenyl)ethyl)-1-methyl-1-(1,2,2,5,5-pentamethylpiperidin-4-yl)urea, |
| GA25 | 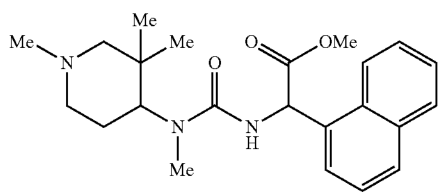 [SMILES: COC(=O)C(NC(=O)N(C)C1CCN(C)CC1(C)C)c1cccc2ccccc12] | methyl 2-(3-methyl-3-(1,3,3-trimethylpiperidin-4-yl)ureido)-2-(naphthalen-1-yl)acetate, |
| GA26 | 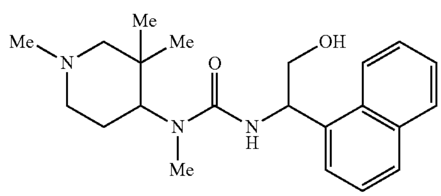 [SMILES: CN1CCC(N(C)C(=O)NC(CO)c2cccc3ccccc23)C(C)(C)C1] | 3-(2-hydroxy-1-(naphthalen-1-yl)ethyl)-1-methyl-1-(1,3,3-trimethylpiperidin-4-yl)urea, |
| GA27 | 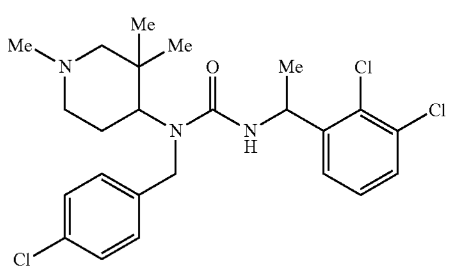 [SMILES: CC(NC(=O)N(Cc1ccc(Cl)cc1)C1CCN(C)CC1(C)C)c1cccc(Cl)c1Cl] | 1-(4-chlorobenzyl)-3-(1-(2,3-dichlorophenyl)ethyl)-1-(1,3,3-trimethylpiperidin-4-yl)urea, |
| GA28 | 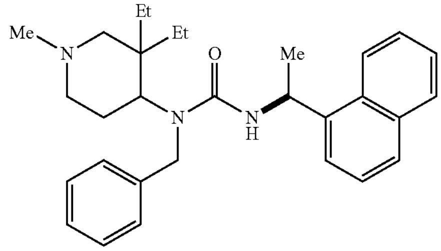 | 1-benzyl-1-(3,3-diethyl-1-methylpiperidin-4-yl)-3-((S)-1-(naphthalen-1-yl)ethyl)urea, |

-continued

| Compound No. | Chemical Structure | Chemical Name |
|---|---|---|
| GA29 | 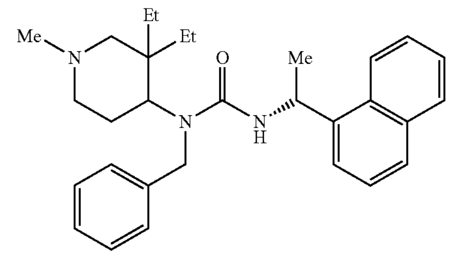 | 1-benzyl-1-(3,3-diethyl-1-methylpiperidin-4-yl)-3-((R)-1-(naphthalen-1-yl)ethyl)urea, |
| GA30 | 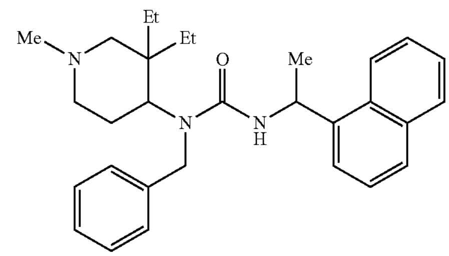 | 1-benzyl-1-(3,3-diethyl-1-methylpiperidin-4-yl)-3-(1-(naphthalen-1-yl)ethyl)urea, |
| GA31 | 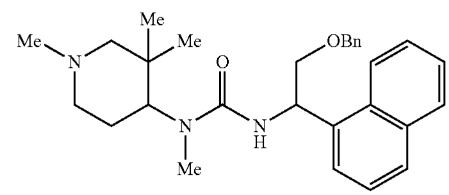 [SMILES: CN1CCC(N(C)C(=O)NC(COCc2ccccc2)c2cccc3ccccc23)C(C)(C)C1] | 3-(2-(benzyloxy)-1-(naphthalen-1-yl)ethyl)-1-methyl-1-(1,3,3-trimethylpiperidin-4-yl)urea, |
| GA32 | 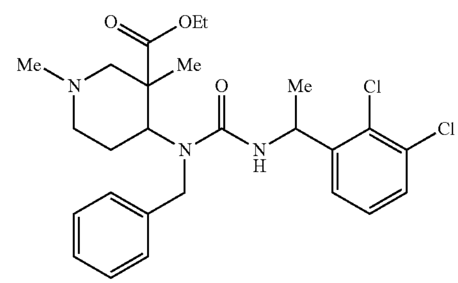 | ethyl 4-(1-benzyl-3-(1-(2,3-dichlorophenyl)ethyl)ureido)-1,3-dimethylpiperidine-3-carboxylate, |
| GA33 | 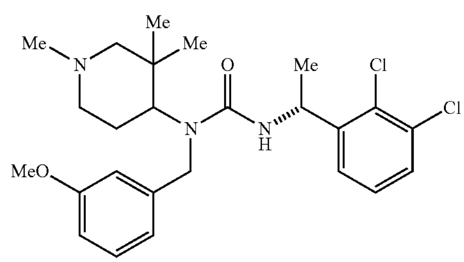 | 3-((R)-1-(2,3-dichlorophenyl)ethyl)-1-(3-methoxybenzyl)-1-(1,3,3-trimethylpiperidin-4-yl)urea, |
| GA34 | 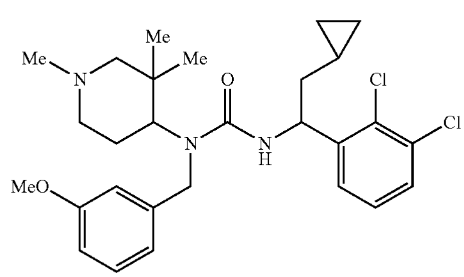 [SMILES: COc1cccc(CN(C(=O)NC(CC2CC2)c2cccc(Cl)c2Cl)C2CCN(C)CC2(C)C)c1] | 3-(2-cyclopropyl-1-(2,3-dichlorophenyl)ethyl)-1-(3-methoxybenzyl)-1-(1,3,3-trimethylpiperidin-4-yl)urea, |

| Compound No. | Chemical Structure | Chemical Name |
|---|---|---|
| GA35 | 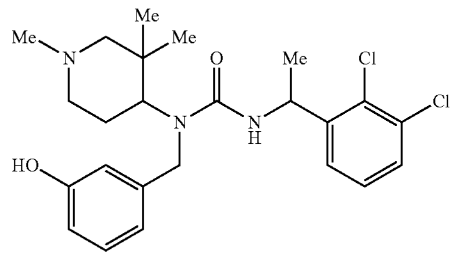 [SMILES: CC(NC(=O)N(Cc1cccc(O)c1)C1CCN(C)CC1(C)C)c1cccc(Cl)c1Cl] | 3-(1-(2,3-dichlorophenyl)ethyl)-1-(3-hydroxybenzyl)-1-(1,3,3-trimethylpiperidin-4-yl)urea, |
| GA36 | 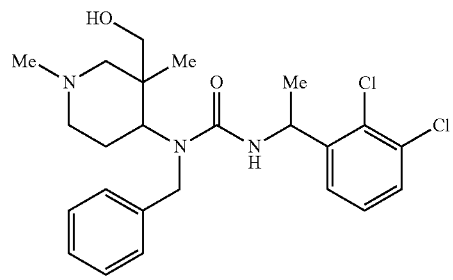 [SMILES: CC(NC(=O)N(Cc1ccccc1)C1CCN(C)CC1(C)CO)c1cccc(Cl)c1Cl] | 1-benzyl-3-(1-(2,3-dichlorophenyl)ethyl)-1-(3-(hydroxymethyl)-1,3-dimethylpiperidin-4-yl)urea, |
| GA37 | 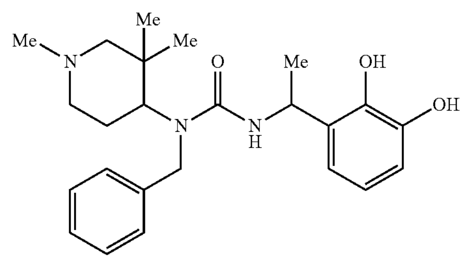 [SMILES: CC(NC(=O)N(Cc1ccccc1)C1CCN(C)CC1(C)C)c1cccc(O)c1O] | 1-benzyl-3-(1-(2,3-dihydroxyphenyl)ethyl)-1-(1,3,3-trimethylpiperidin-4-yl)urea, |
| GA38 | 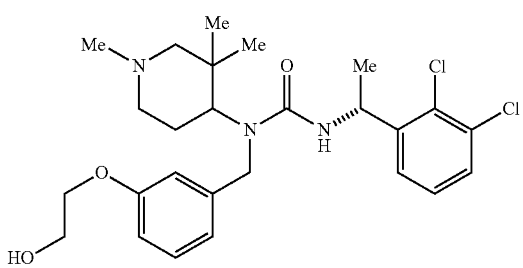 | 3-((R)-1-(2,3-dichlorophenyl)ethyl)-1-(3-(2-hydroxyethoxy)benzyl)-1-(1,3,3-trimethylpiperidin-4-yl)urea, |
| GA39 | 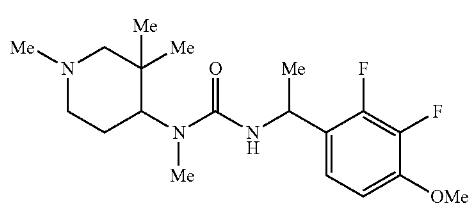 [SMILES: COc1ccc(C(C)NC(=O)N(C)C2CCN(C)CC2(C)C)c(F)c1F] | 3-(1-(2,3-difluoro-4-methoxyphenyl)ethyl)-1-methyl-1-(1,3,3-trimethylpiperidin-4-yl)urea, |
| GA40 | 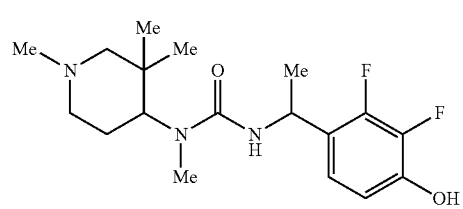 [SMILES: CC(NC(=O)N(C)C1CCN(C)CC1(C)C)c1ccc(O)c(F)c1F] | 3-(1-(2,3-difluoro-4-hydroxyphenyl)ethyl)-1-methyl-1-(1,3,3-trimethylpiperidin-4-yl)urea, |

-continued

| Compound No. | Chemical Structure | Chemical Name |
|---|---|---|
| GA41 | 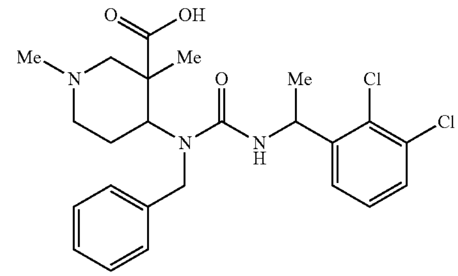 [SMILES: CC(NC(=O)N(Cc1ccccc1)C1CCN(C)CC1(C)C(=O)O)c1cccc(Cl)c1Cl] | 4-(1-benzyl-3-(1-(2,3-dichlorophenyl)ethyl)ureido)-1,3-dimethylpiperidine-3-carboxylic acid, |
| GA42 | 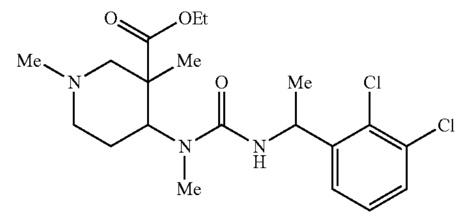 [SMILES: CCOC(=O)C1(C)CN(C)CCC1N(C)C(=O)NC(C)c1cccc(Cl)c1Cl] | ethyl 4-(3-(1-(2,3-dichlorophenyl)ethyl)-1-methylureido)-1,3-dimethylpiperidine-3-carboxylate, |
| GA43 | 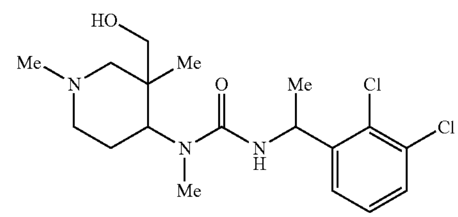 [SMILES: CC(NC(=O)N(C)C1CCN(C)CC1(C)CO)c1cccc(Cl)c1Cl] | 3-(1-(2,3-dichlorophenyl)ethyl)-1-(3-(hydroxymethyl)-1,3-dimethylpiperidin-4-yl)-1-methylurea, |
| GA44 | 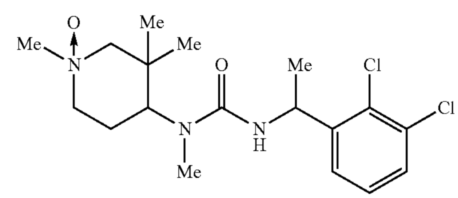 [SMILES: CC(NC(=O)N(C)C1CC[N+](C)([O-])CC1(C)C)c1cccc(Cl)c1Cl] | 4-(3-(1-(2,3-dichlorophenyl)ethyl)-1-methylureido)-1,3,3-trimethylpiperidine 1-oxide, |
| GA45 | 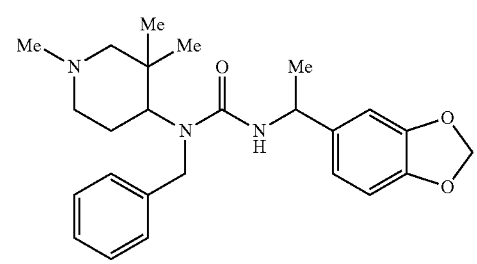 [SMILES: CC(NC(=O)N(Cc1ccccc1)C1CCN(C)CC1(C)C)c1ccc2c(c1)OCO2] | 3-(1-(benzo[d][1,3]dioxol-5-yl)ethyl)-1-benzyl-1-(1,3,3-trimethylpiperidin-4-yl)urea, |
| GA46 | 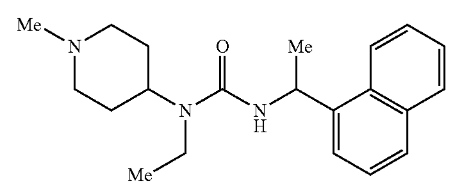 [SMILES: CCN(C(=O)NC(C)c1cccc2ccccc12)C1CCN(C)CC1] | 1-ethyl-1-(1-methylpiperidin-4-yl)-3-(1-(naphthalen-1-yl)ethyl)urea, |
| GA47 | 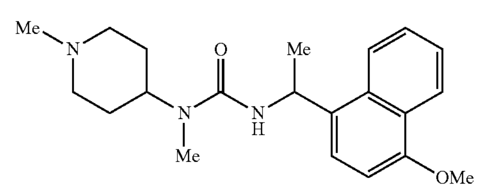 [SMILES: COc1ccc(C(C)NC(=O)N(C)C2CCN(C)CC2)c2ccccc12] | 3-(1-(4-methoxynaphthalen-1-yl)ethyl)-1-methyl-methylpiperidin-4-yl)urea, |

-continued

| Compound No. | Chemical Structure | Chemical Name |
|---|---|---|
| GA48 | 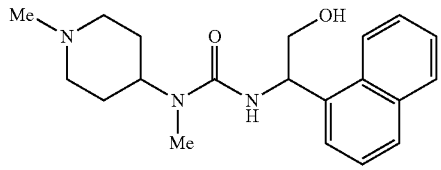 | 3-(2-hydroxy-1-(naphthalen-1-yl)ethyl)-1-methyl-1-(1-methylpiperidin-4-yl)urea, |
| GA49 | 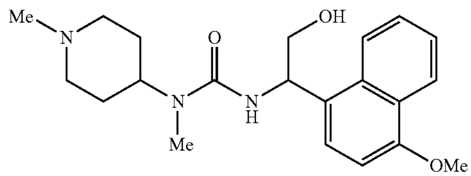 [SMILES: COc1ccc(C(CO)NC(=O)N(C)C2CCN(C)CC2)c2ccccc12] | 3-(2-hydroxy-1-(4-methoxynaphthalen-1-yl)ethyl)-1-methyl-1-(1-methylpiperidin-4-yl)urea, |
| GA50 | 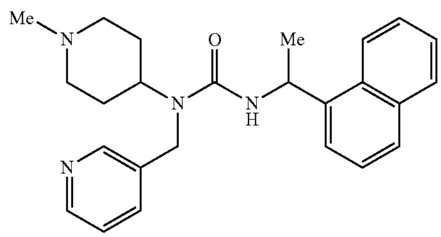 [SMILES: CC(NC(=O)N(Cc1cccnc1)C1CCN(C)CC1)c1cccc2ccccc12] | 1-(1-methylpiperidin-4-yl)-3-(1-(naphthalen-1-yl)ethyl)-1-(pyridin-3-ylmethyl)urea, |
| GA51 | 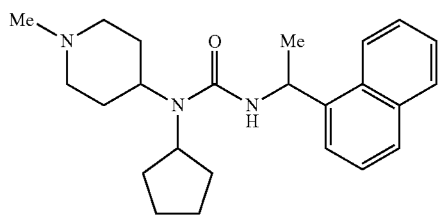 [SMILES: CC(NC(=O)N(C1CCCC1)C1CCN(C)CC1)c1cccc2ccccc12] | 1-cyclopentyl-1-(1-methylpiperidin-4-yl)-3-(1-(naphthalen-1-yl)ethyl)urea, |
| GA52 | 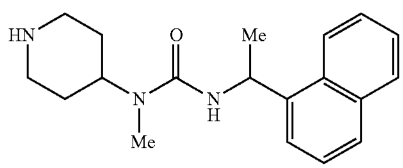 [SMILES: CC(NC(=O)N(C)C1CCNCC1)c1cccc2ccccc12] | 1-methyl-3-(1-(naphthalen-1-yl)ethyl)-1-(piperidin-4-yl)urea, |
| GA53 | 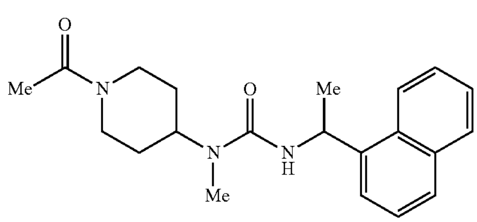 [SMILES: CC(=O)N1CCC(N(C)C(=O)NC(C)c2cccc3ccccc23)CC1] | 1-(1-acetylpiperidin-4-yl)-1-methyl-3-(1-(naphthalen-1-yl)ethyl)urea, |
| GA54 | 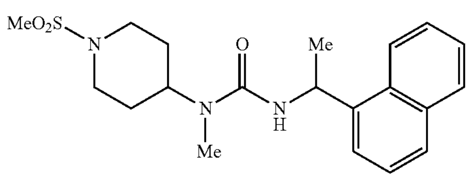 [SMILES: CC(NC(=O)N(C)C1CCN(S(C)(=O)=O)CC1)c1cccc2ccccc12] | 1-methyl-1-(1-(methylsulfonyl)piperidin-4-yl)-3-(1-(naphthalen-1-yl)ethyl)urea, |
| GA55 | 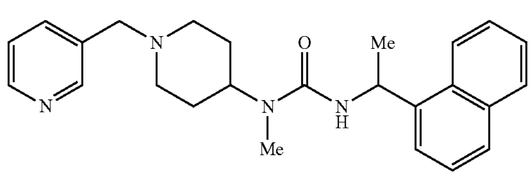 [SMILES: CC(NC(=O)N(C)C1CCN(Cc2cccnc2)CC1)c1cccc2ccccc12] | 1-methyl-3-(1-(naphthalen-1-yl)ethyl)-1-(1-(pyridin-3-ylmethyl)piperidin-4-yl)urea, |

-continued

| Compound No. | Chemical Structure | Chemical Name |
|---|---|---|
| GA56 | 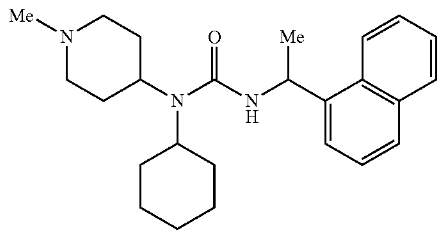 [SMILES: CC(NC(=O)N(C1CCCCC1)C1CCN(C)CC1)c1cccc2ccccc12] | 1-cyclohexyl-1-(1-methylpiperidin-4-yl)-3-(1-(naphthalen-1-yl)ethyl)urea, |
| GA57 | 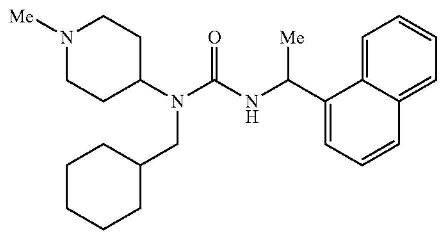 [SMILES: CC(NC(=O)N(CC1CCCCC1)C1CCN(C)CC1)c1cccc2ccccc12] | 1-(cyclohexylmethyl)-1-(1-methylpiperidin-4-yl)-3-(1-(naphthalen-1-yl)ethyl)urea, |
| GA58 | 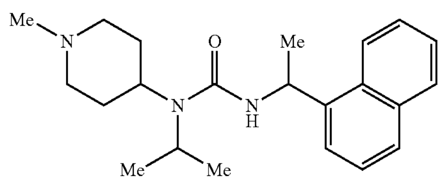 [SMILES: CC(NC(=O)N(C(C)C)C1CCN(C)CC1)c1cccc2ccccc12] | 1-isopropyl-1-(1-methylpiperidin-4-yl)-3-(1-(naphthalen-1-yl)ethyl)urea, |
| GA59 | 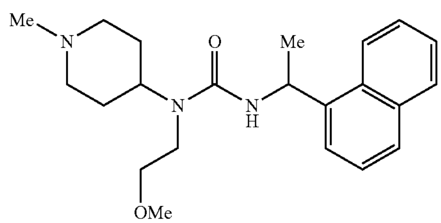 [SMILES: COCCN(C(=O)NC(C)c1cccc2ccccc12)C1CCN(C)CC1] | 1-(2-methoxyethyl)-1-(1-methylpiperidin-4-yl)-3-(1-(naphthalen-1-yl)ethyl)urea, |
| GA60 | 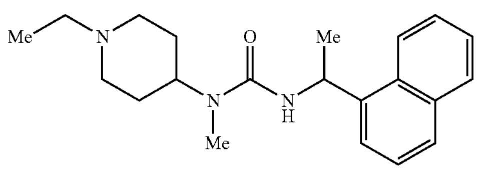 [SMILES: CCN1CCC(N(C)C(=O)NC(C)c2cccc3ccccc23)CC1] | 1-(1-ethylpiperidin-4-yl)-1-methyl-3-(1-(naphthalen-1-yl)ethyl)urea, |
| GA61 | 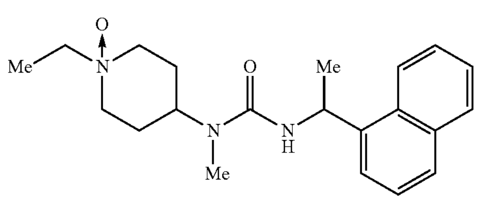 [SMILES: CC[N+]1([O-])CCC(N(C)C(=O)NC(C)c2cccc3ccccc23)CC1] | 1-ethyl-4-(1-methyl-3-(1-(naphthalen-1-yl)ethyl)ureido)piperidine 1-oxide, |
| GA62 | 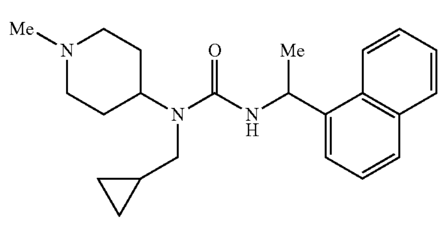 [SMILES: CC(NC(=O)N(CC1CC1)C1CCN(C)CC1)c1cccc2ccccc12] | 1-(cyclopropylmethyl)-1-(1-methylpiperidin-4-yl)-3-(1-(naphthalen-1-yl)ethyl)urea, |

-continued

| Compound No. | Chemical Structure | Chemical Name |
|---|---|---|
| GA63 | 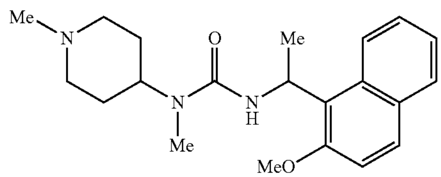 [SMILES: COc1ccc2ccccc2c1C(C)NC(=O)N(C)C1CCN(C)CC1] | 3-(1-(2-methoxynaphthalen-1-yl)ethyl)-1-methyl-1-(1-methylpiperidin-4-yl)urea, |
| GA64 | 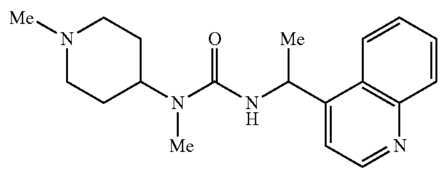 [SMILES: CC(NC(=O)N(C)C1CCN(C)CC1)c1ccnc2ccccc12] | 1-methyl-1-(1-methylpiperidin-4-yl)-3-(1-(quinolin-4-yl)ethyl)urea, |
| GA65 | 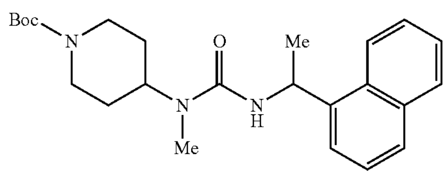 [SMILES: CC(NC(=O)N(C)C1CCN(C(=O)OC(C)(C)C)CC1)c1cccc2ccccc12] | tert-butyl 4-(1-methyl-3-(1-(naphthalen-1-yl)ethyl)ureido)piperidine-1-carboxylate, |
| GA66 | 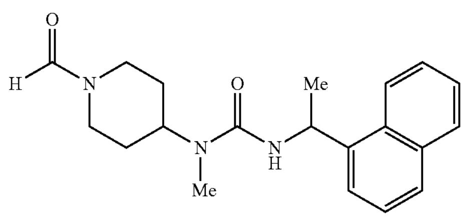 [SMILES: CC(NC(=O)N(C)C1CCN(C=O)CC1)c1cccc2ccccc12] | 1-(1-formylpiperidin-4-yl)-1-methyl-3-(1-(naphthalen-1-yl)ethyl)urea, |
| GA67 | 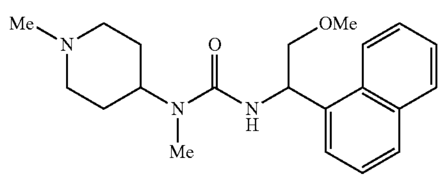 [SMILES: COCC(NC(=O)N(C)C1CCN(C)CC1)c1cccc2ccccc12] | 3-(2-methoxy-1-(naphthalen-1-yl)ethyl)-1-methyl-methylpiperidin-4-yl)urea, |
| GA68 | 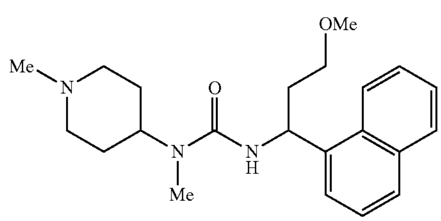 [SMILES: COCCC(NC(=O)N(C)C1CCN(C)CC1)c1cccc2ccccc12] | 3-(3-methoxy-1-(naphthalen-1-yl)propyl)-1-methyl-1-(1-methylpiperidin-4-yl)urea, |
| GA69 | 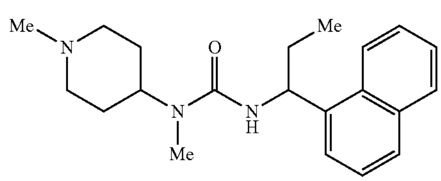 [SMILES: CCC(NC(=O)N(C)C1CCN(C)CC1)c1cccc2ccccc12] | 1-methyl-1-(1-methylpiperidin-4-yl)-3-(1-(naphthalen-1-yl)propyl)urea, |
| GA70 | 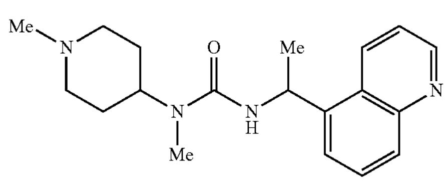 [SMILES: CC(NC(=O)N(C)C1CCN(C)CC1)c1cccc2ncccc12] | 1-methyl-1-(1-methylpiperidin-4-yl)-3-(1-(quinolin-5-yl)ethyl)urea, |

-continued

| Compound No. | Chemical Structure | Chemical Name |
|---|---|---|
| GA71 | 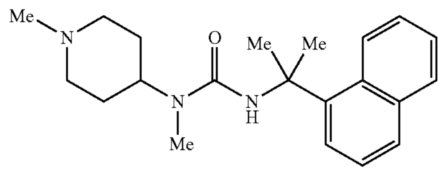 [SMILES: CN1CCC(N(C)C(=O)NC(C)(C)c2cccc3ccccc23)CC1] | 1-methyl-1-(1-methylpiperidin-4-yl)-3-(2-(naphthalen-1-yl)propan-2-yl)urea, |
| GA72 | 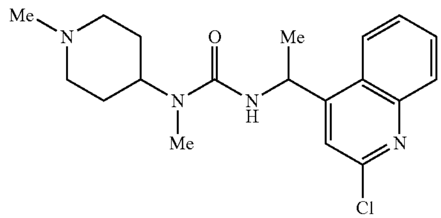 [SMILES: CC(NC(=O)N(C)C1CCN(C)CC1)c1cc(Cl)nc2ccccc12] | 3-(1-(2-chloroquinolin-4-yl)ethyl)-1-methyl-1-(1-methylpiperidin-4-yl)urea, |
| GA73 | 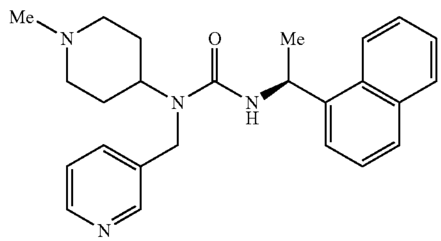 [SMILES: C[C@H](NC(=O)N(Cc1cccnc1)C1CCN(C)CC1)c1cccc2ccccc12] | (S)-1-(1-methylpiperidin-4-yl)-3-(1-(naphthalen-1-yl)ethyl)-1-(pyridin-3-ylmethyl)urea, |
| GA74 | 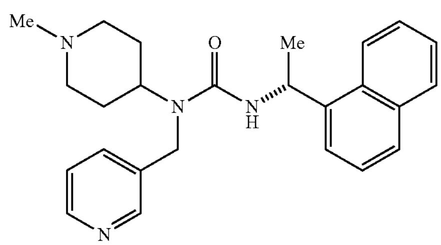 | (R)-1-(1-methylpiperidin-4-yl)-3-(1-(naphthalen-1-yl)ethyl)-1-(pyridin-3-ylmethyl)urea, |
| GA75 | 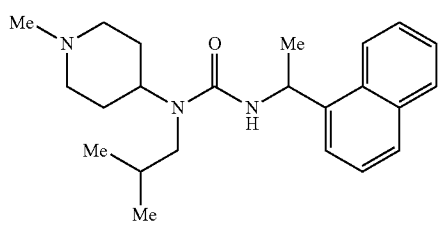 [SMILES: CC(C)CN(C(=O)NC(C)c1cccc2ccccc12)C1CCN(C)CC1] | 1-isobutyl-1-(1-methylpiperidin-4-yl)-3-(1-(naphthalen-1-yl)ethyl)urea, |
| GA76 | 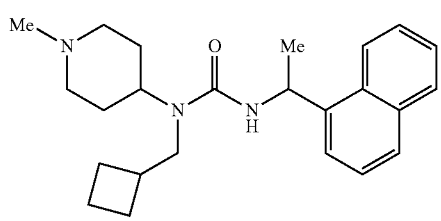 [SMILES: CC(NC(=O)N(CC1CCC1)C1CCN(C)CC1)c1cccc2ccccc12] | 1-(cyclobutylmethyl)-1-(1-methylpiperidin-4-yl)-3-(1-(naphthalen-1-yl)ethyl)urea, |
| GA77 | 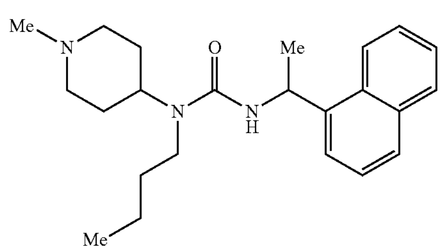 [SMILES: CCCCN(C(=O)NC(C)c1cccc2ccccc12)C1CCN(C)CC1] | 1-butyl-1-(1-methylpiperidin-4-yl)-3-(1-(naphthalen-1-yl)ethyl)urea, |

| Compound No. | Chemical Structure | Chemical Name |
|---|---|---|
| GA78 | 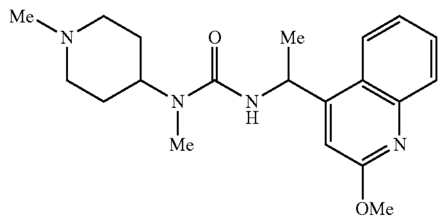 [SMILES: COc1cc(C(C)NC(=O)N(C)C2CCN(C)CC2)c2ccccc2n1] | 3-(1-(2-methoxyquinolin-4-yl)ethyl)-1-methyl-1-(1-methylpiperidin-4-yl)urea, |
| GA79 | 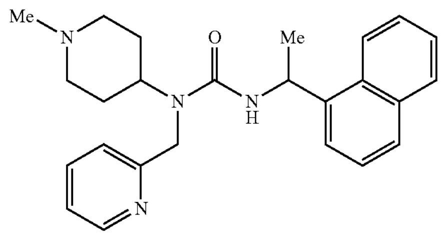 [SMILES: CC(NC(=O)N(Cc1ccccn1)C1CCN(C)CC1)c1cccc2ccccc12] | 1-(1-methylpiperidin-4-yl)-3-(1-(naphthalen-1-yl)ethyl)-1-(pyridin-2-ylmethyl)urea, |
| GA80 | 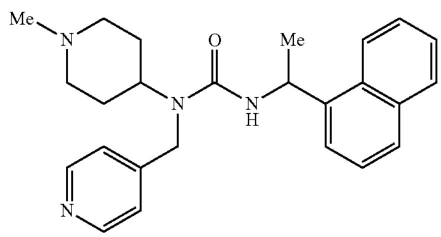 [SMILES: CC(NC(=O)N(Cc1ccncc1)C1CCN(C)CC1)c1cccc2ccccc12] | 1-(1-methylpiperidin-4-yl)-3-(1-(naphthalen-1-yl)ethyl)-1-(pyridin-4-ylmethyl)urea, |
| GA81 | 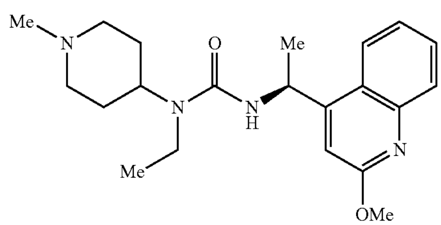 [SMILES: CCN(C(=O)N[C@@H](C)c1cc(OC)nc2ccccc12)C1CCN(C)CC1] | (S)-1-ethyl-3-(1-(2-methoxyquinolin-4-yl)ethyl)-1-(1-methylpiperidin-4-yl)urea, |
| GA82 | 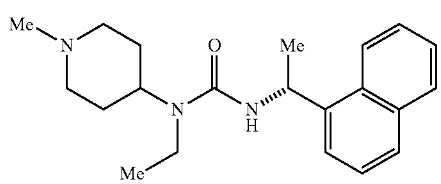 | (R)-1-ethyl-1-(1-methylpiperidin-4-yl)-3-(1-(naphthalen-1-yl)ethyl)urea, |
| GA83 | 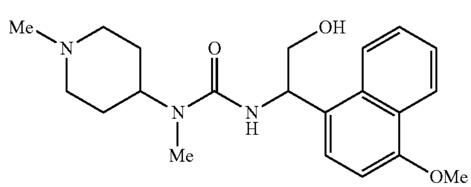 [SMILES: COc1ccc(C(CO)NC(=O)N(C)C2CCN(C)CC2)c2ccccc12] | 3-(2-hydroxy-1-(4-methoxynaphthalen-1-yl)ethyl)-1-methyl-1-(1-methylpiperidin-4-yl)urea, |
| GA84 | 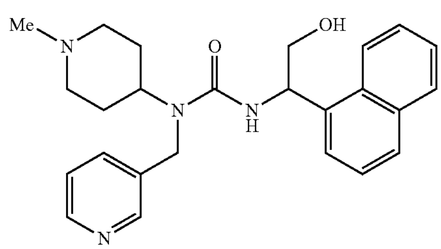 [SMILES: CN1CCC(N(Cc2cccnc2)C(=O)NC(CO)c2cccc3ccccc23)CC1] | 3-(2-hydroxy-1-(naphthalen-1-yl)ethyl)-1-(1-methylpiperidin-4-yl)-1-(pyridin-3-ylmethyl)urea, |

-continued

| Compound No. | Chemical Structure | Chemical Name |
|---|---|---|
| GA85 | 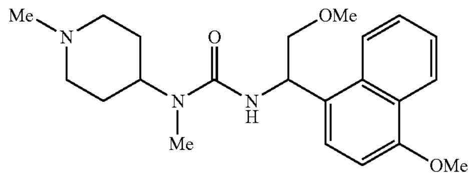 [SMILES: COCC(NC(=O)N(C)C1CCN(C)CC1)c1ccc(OC)c2ccccc12] | 3-(2-methoxy-1-(4-methoxynaphthalen-1-yl)ethyl)-1-methyl-1-(1-methylpiperidin-4-yl)urea, |
| GA86 | 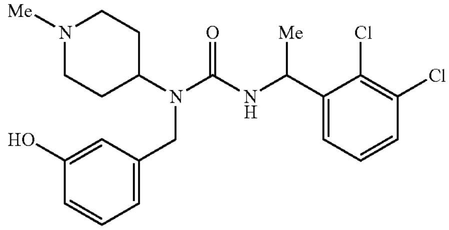 [SMILES: CC(NC(=O)N(Cc1cccc(O)c1)C1CCN(C)CC1)c1cccc(Cl)c1Cl] | 3-(1-(2,3-dichlorophenyl)ethyl)-1-(3-hydroxybenzyl)-1-(1-methylpiperidin-4-yl)urea, |
| GA87 | 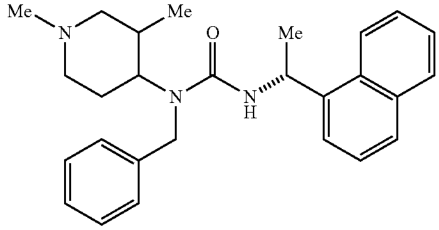 | 1-benzyl-1-(1,3-dimethylpiperidin-4-yl)-3-((R)-1-(naphthalen-1-yl)ethyl)urea, |
| GA88 | 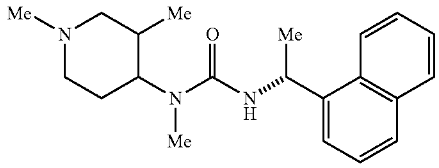 | 1-(1,3-dimethylpiperidin-4-yl)-1-methyl-3-((R)-1-(naphthalen-1-yl)ethyl)urea, |
| GA89 | 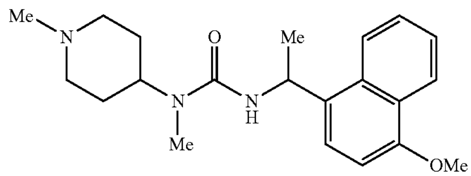 [SMILES: COc1ccc(C(C)NC(=O)N(C)C2CCN(C)CC2)c2ccccc12] | 3-(1-(4-methoxynaphthalen-1-yl)ethyl)-1-methyl-1-(1-methylpiperidin-4-yl)urea, |
| GA90 | 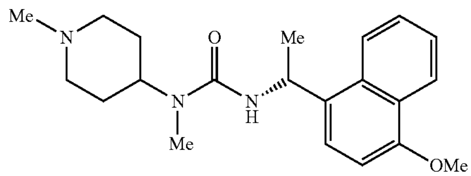 | (R)-3-(1-(4-methoxynaphthalen-1-yl)ethyl)-1-methyl-1-(1-methylpiperidin-4-yl)urea, |
| GA91 | 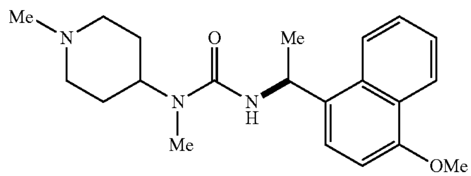 | (S)-3-(1-(4-methoxynaphthalen-1-yl)ethyl)-1-methyl-1-(1-methylpiperidin-4-yl)urea, |
| GA92 | 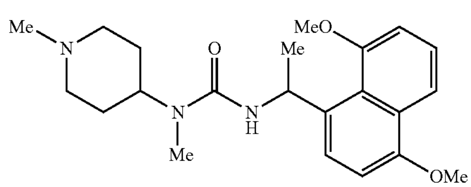 [SMILES: COc1ccc(C(C)NC(=O)N(C)C2CCN(C)CC2)c2c(OC)cccc12] | 3-(1-(4,8-dimethoxynaphthalen-1-yl)ethyl)-1-methyl-methylpiperidin-4-yl)urea, |

-continued

| Compound No. | Chemical Structure | Chemical Name |
|---|---|---|
| GA93 | 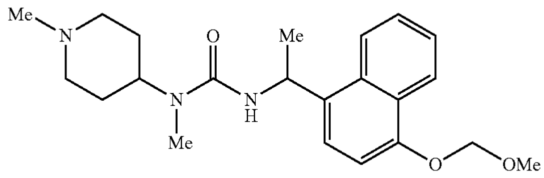 [SMILES: COCOc1ccc(C(C)NC(=O)N(C)C2CCN(C)CC2)c2ccccc12] | 3-(1-(4-(methoxymethoxy)naphthalen-1-yl)ethyl)-1-methyl-1-(1-methylpiperidin-4-yl)urea, |
| GA94 | 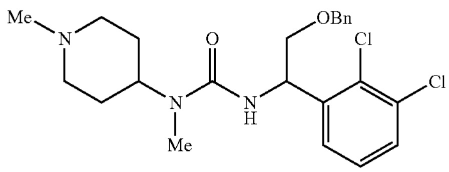 [SMILES: CN1CCC(N(C)C(=O)NC(COCc2ccccc2)c2cccc(Cl)c2Cl)CC1] | 3-(2-(benzyloxy)-1-(2,3-dichlorophenyl)ethyl)-1-methyl-1-(1-methylpiperidin-4-yl)urea, |
| GA95 | 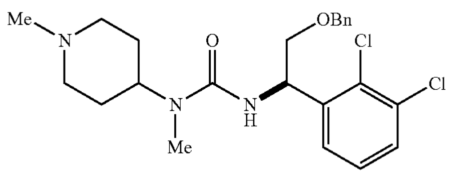 | (R)-3-(2-(benzyloxy)-1-(2,3-dichlorophenyl)ethyl)-1-methyl-1-(1-methylpiperidin-4-yl)urea, |
| GA96 | 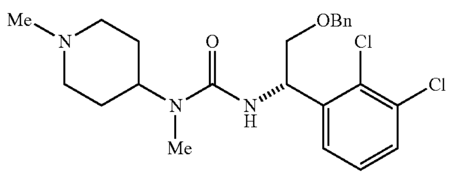 | (S)-3-(2-(benzyloxy)-1-(2,3-dichlorophenyl)ethyl)-1-methyl-1-(1-methylpiperidin-4-yl)urea, |
| GA97 | 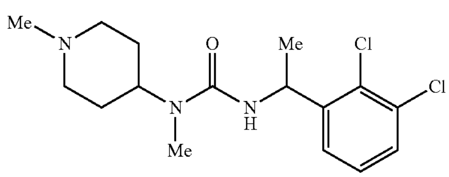 [SMILES: CC(NC(=O)N(C)C1CCN(C)CC1)c1cccc(Cl)c1Cl] | 3-(1-(2,3-dichlorophenyl)ethyl)-1-methyl-1-(1-methylpiperidin-4-yl)urea, |
| GA98 | 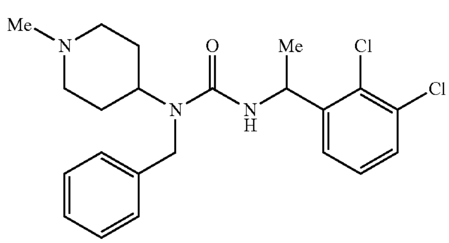 [SMILES: CC(NC(=O)N(Cc1ccccc1)C1CCN(C)CC1)c1cccc(Cl)c1Cl] | 1-benzyl-3-(1-(2,3-dichlorophenyl)ethyl)-1-(1-methylpiperidin-4-yl)urea, |
| GA99 | 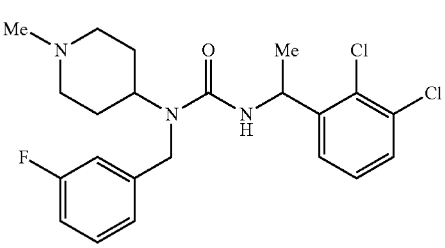 [SMILES: CC(NC(=O)N(Cc1cccc(F)c1)C1CCN(C)CC1)c1cccc(Cl)c1Cl] | 3-(1-(2,3-dichlorophenyl)ethyl)-1-(3-fluorobenzyl)-1-(1-methylpiperidin-4-yl)urea, |

-continued

| Compound No. | Chemical Structure | Chemical Name |
|---|---|---|
| GA100 | 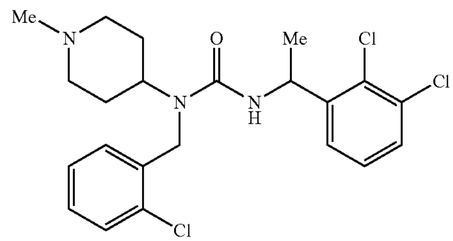 | 1-(2-chlorobenzyl)-3-(1-(2,3-dichlorophenyl)ethyl)-1-(1-methylpiperidin-4-yl)urea, |
| GA101 | 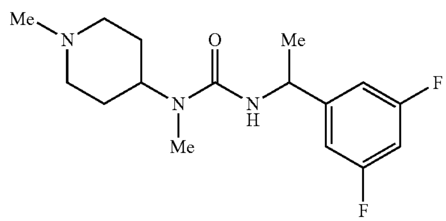 [SMILES: CC(NC(=O)N(C)C1CCN(C)CC1)c1cc(F)cc(F)c1] | 3-(1-(3,5-difluorophenyl)ethyl)-1-methyl-1-(1-methylpiperidin-4-yl)urea, |
| GA102 | 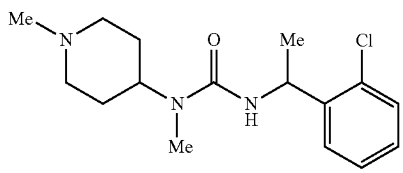 [SMILES: CC(NC(=O)N(C)C1CCN(C)CC1)c1ccccc1Cl] | 3-(1-(2-chlorophenyl)ethyl)-1-methyl-1-(1-methylpiperidin-4-yl)urea, |
| GA103 | 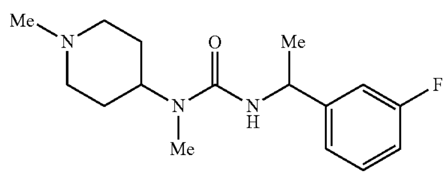 [SMILES: CC(NC(=O)N(C)C1CCN(C)CC1)c1cccc(F)c1] | 3-(1-(3-fluorophenyl)ethyl)-1-methyl-1-(1-methylpiperidin-4-yl)urea, |
| GA104 | 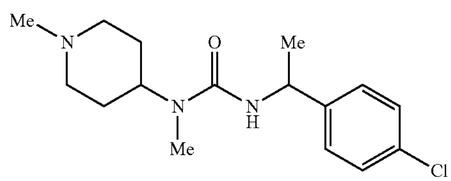 [SMILES: CC(NC(=O)N(C)C1CCN(C)CC1)c1ccc(Cl)cc1] | 3-(1-(4-chlorophenyl)ethyl)-1-methyl-1-(1-methylpiperidin-4-yl)urea, |
| GA105 | 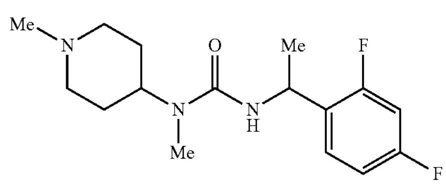 [SMILES: CC(NC(=O)N(C)C1CCN(C)CC1)c1ccc(F)cc1F] | 3-(1-(2,4-difluorophenyl)ethyl)-1-methyl-1-(1-methylpiperidin-4-yl)urea, |
| GA106 | 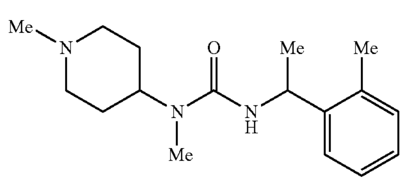 [SMILES: Cc1ccccc1C(C)NC(=O)N(C)C1CCN(C)CC1] | 1-methyl-1-(1-methylpiperidin-4-yl)-3-(1-(o-tolyl)ethyl)urea, |
| GA107 | 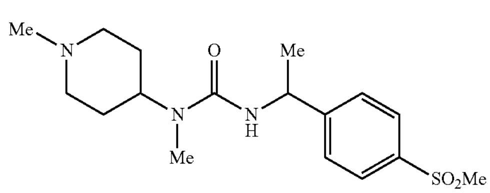 [SMILES: CC(NC(=O)N(C)C1CCN(C)CC1)c1ccc(S(C)(=O)=O)cc1] | 1-methyl-1-(1-methylpiperidin-4-yl)-3-(1-(4-(methylsulfonyl)phenyl)ethyl)urea, |

| Compound No. | Chemical Structure | Chemical Name |
|---|---|---|
| GA108 | 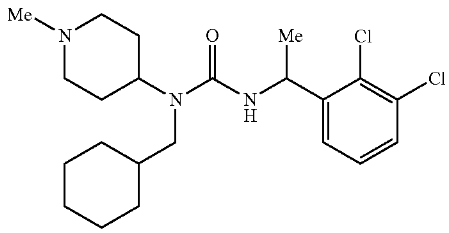 [SMILES: CC(NC(=O)N(CC1CCCCC1)C1CCN(C)CC1)c1cccc(Cl)c1Cl] | 1-(cyclohexylmethyl)-3-(1-(2,3-dichlorophenyl)ethyl)-1-(1-methylpiperidin-4-yl)urea, |
| GA109 | 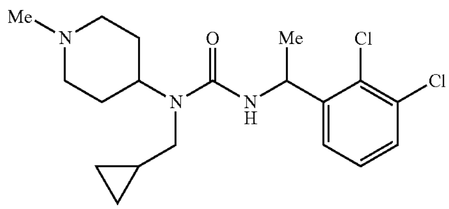 [SMILES: CC(NC(=O)N(CC1CC1)C1CCN(C)CC1)c1cccc(Cl)c1Cl] | 1-(cyclopropylmethyl)-3-(1-(2,3-dichlorophenyl)ethyl)-1-(1-methylpiperidin-4-yl)urea, |
| GA110 | 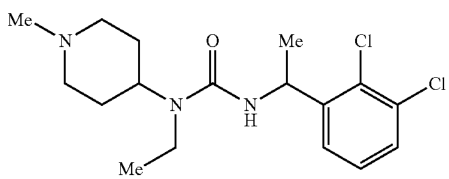 [SMILES: CCN(C(=O)NC(C)c1cccc(Cl)c1Cl)C1CCN(C)CC1] | 3-(1-(2,3-dichlorophenyl)ethyl)-1-ethyl-1-(1-methylpiperidin-4-yl)urea, |
| GA111 | 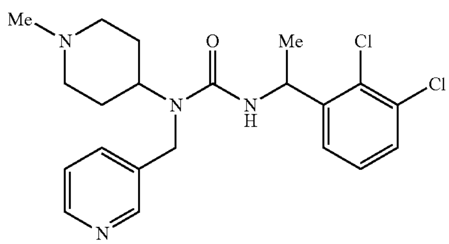 [SMILES: CC(NC(=O)N(Cc1cccnc1)C1CCN(C)CC1)c1cccc(Cl)c1Cl] | 3-(1-(2,3-dichlorophenyl)ethyl)-1-(1-methylpiperidin-4-yl)-1-(pyridin-3-ylmethyl)urea, |
| GA112 | 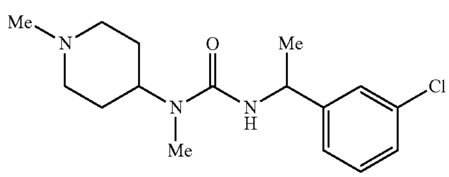 [SMILES: CC(NC(=O)N(C)C1CCN(C)CC1)c1cccc(Cl)c1] | 3-(1-(3-chlorophenyl)ethyl)-1-methyl-1-(1-methylpiperidin-4-yl)urea, |
| GA113 | 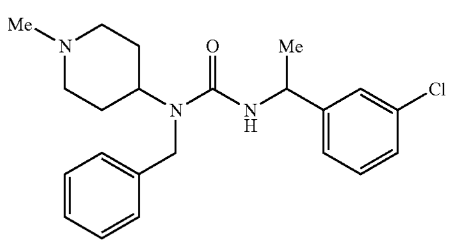 [SMILES: CC(NC(=O)N(Cc1ccccc1)C1CCN(C)CC1)c1cccc(Cl)c1] | 1-benzyl-3-(1-(3-chlorophenyl)ethyl)-1-(1-methylpiperidin-4-yl)urea, |
| GA114 | 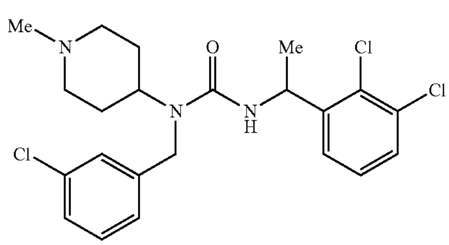 [SMILES: CC(NC(=O)N(Cc1cccc(Cl)c1)C1CCN(C)CC1)c1cccc(Cl)c1Cl] | 1-(3-chlorobenzyl)-3-(1-(2,3-dichlorophenyl)ethyl)-1-(1-methylpiperidin-4-yl)urea, |

-continued

| Compound No. | Chemical Structure | Chemical Name |
|---|---|---|
| GA115 | 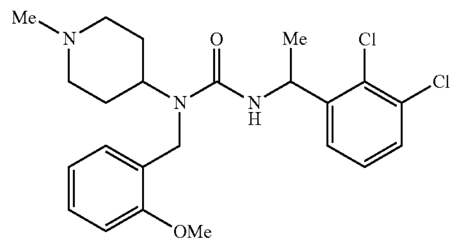 [SMILES: COc1ccccc1CN(C(=O)NC(C)c1cccc(Cl)c1Cl)C1CCN(C)CC1] | 3-(1-(2,3-dichlorophenyl)ethyl)-1-(2-methoxybenzyl)-1-(1-methylpiperidin-4-yl)urea, |
| GA116 | 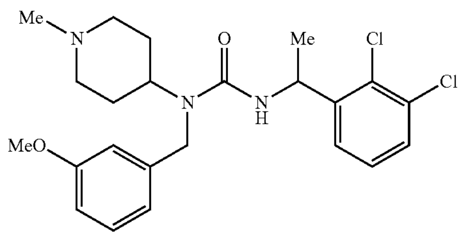 [SMILES: COc1cccc(CN(C(=O)NC(C)c2cccc(Cl)c2Cl)C2CCN(C)CC2)c1] | 3-(1-(2,3-dichlorophenyl)ethyl)-1-(3-methoxybenzyl)-1-(1-methylpiperidin-4-yl)urea, |
| GA117 | 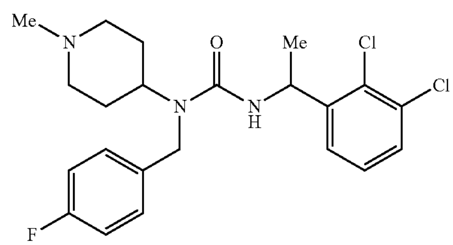 [SMILES: CC(NC(=O)N(Cc1ccc(F)cc1)C1CCN(C)CC1)c1cccc(Cl)c1Cl] | 3-(1-(2,3-dichlorophenyl)ethyl)-1-(4-fluorobenzyl)-1-(1-methylpiperidin-4-yl)urea, |
| GA118 | 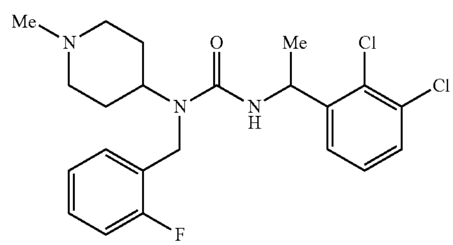 [SMILES: CC(NC(=O)N(Cc1ccccc1F)C1CCN(C)CC1)c1cccc(Cl)c1Cl] | 3-(1-(2,3-dichlorophenyl)ethyl)-1-(2-fluorobenzyl)-1-(1-methylpiperidin-4-yl)urea, |
| GA119 | 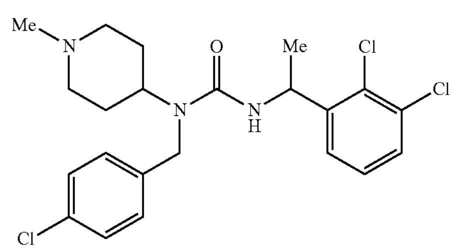 [SMILES: CC(NC(=O)N(Cc1ccc(Cl)cc1)C1CCN(C)CC1)c1cccc(Cl)c1Cl] | 1-(4-chlorobenzyl)-3-(1-(2,3-dichlorophenyl)ethyl)-1-(1-methylpiperidin-4-yl)urea, |
| GA120 | 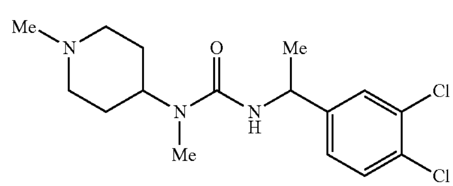 [SMILES: CC(NC(=O)N(C)C1CCN(C)CC1)c1ccc(Cl)c(Cl)c1] | 3-(1-(3,4-dichlorophenyl)ethyl)-1-methyl-1-(1-methylpiperidin-4-yl)urea, |

| Compound No. | Chemical Structure | Chemical Name |
|---|---|---|
| GA121 | 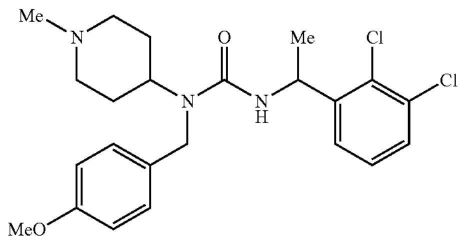 [SMILES: COc1ccc(CN(C(=O)NC(C)c2cccc(Cl)c2Cl)C2CCN(C)CC2)cc1] | 3-(1-(2,3-dichlorophenyl)ethyl)-1-(4-methoxybenzyl)-1-(1-methylpiperidin-4-yl)urea, |
| GA122 | 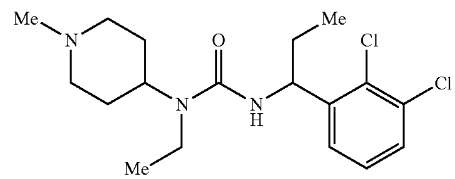 [SMILES: CCC(NC(=O)N(CC)C1CCN(C)CC1)c1cccc(Cl)c1Cl] | 3-(1-(2,3-dichlorophenyl)propyl)-1-ethyl-1-(1-methylpiperidin-4-yl)urea, |
| GA123 | 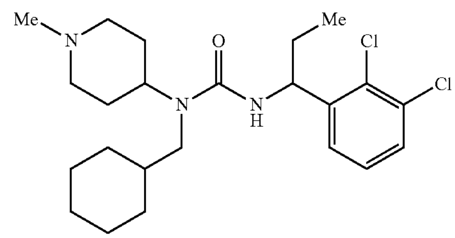 [SMILES: CCC(NC(=O)N(CC1CCCCC1)C1CCN(C)CC1)c1cccc(Cl)c1Cl] | 1-(cyclohexylmethyl)-3-(1-(2,3-dichlorophenyl)propyl)-1-(1-methylpiperidin-4-yl)urea, |
| GA124 | 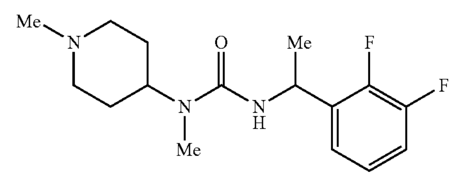 [SMILES: CC(NC(=O)N(C)C1CCN(C)CC1)c1cccc(F)c1F] | 3-(1-(2,3-difluorophenyl)ethyl)-1-methyl-1-(1-methylpiperidin-4-yl)urea, |
| GA125 | 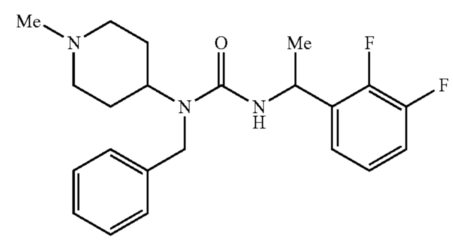 [SMILES: CC(NC(=O)N(Cc1ccccc1)C1CCN(C)CC1)c1cccc(F)c1F] | 1-benzyl-3-(1-(2,3-difluorophenyl)ethyl)-1-(1-methylpiperidin-4-yl)urea, |
| GA126 | 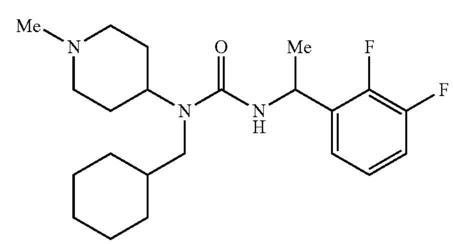 [SMILES: CC(NC(=O)N(CC1CCCCC1)C1CCN(C)CC1)c1cccc(F)c1F] | 1-(cyclohexylmethyl)-3-(1-(2,3-difluorophenyl)ethyl)-1-(1-methylpiperidin-4-yl)urea, |
| GA127 | 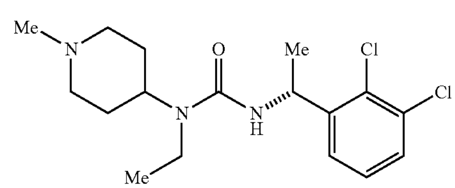 | (R)-3-(1-(2,3-dichlorophenyl)ethyl)-1-ethyl-1-(1-methylpiperidin-4-yl)urea, |

-continued

| Compound No. | Chemical Structure | Chemical Name |
|---|---|---|
| GA128 | 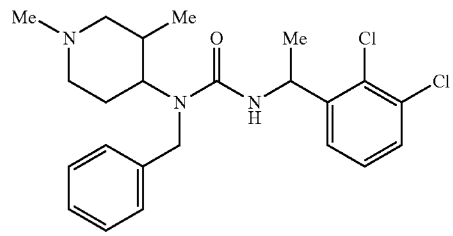 [SMILES: CC(NC(=O)N(Cc1ccccc1)C1CCN(C)CC1C)c1cccc(Cl)c1Cl] | 1-benzyl-3-(1-(2,3-dichlorophenyl)ethyl)-1-(1,3-dimethylpiperidin-4-yl)urea, |
| GA129 | 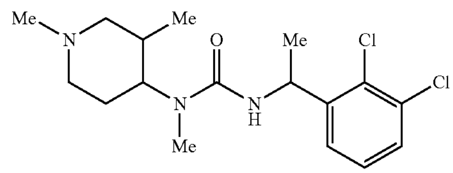 [SMILES: CC(NC(=O)N(C)C1CCN(C)CC1C)c1cccc(Cl)c1Cl] | 3-(1-(2,3-dichlorophenyl)ethyl)-1-(1,3-dimethylpiperidin-4-yl)-1-methylurea, |
| GA130 | 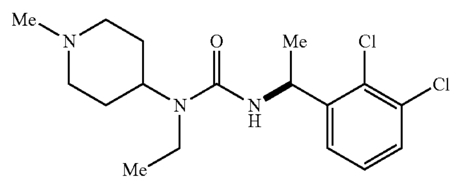 | (S)-3-(1-(2,3-dichlorophenyl)ethyl)-1-ethyl-1-(1-methylpiperidin-4-yl)urea, |
| GA131 | 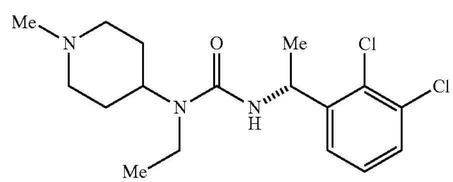 | (R)-3-(1-(2,3-dichlorophenyl)ethyl)-1-ethyl-1-(1-methylpiperidin-4-yl)urea, |
| GA132 | 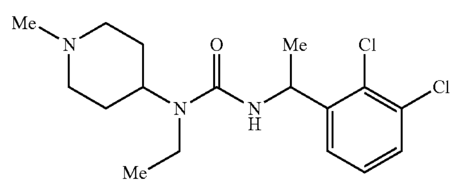 [SMILES: CCN(C(=O)NC(C)c1cccc(Cl)c1Cl)C1CCN(C)CC1] | 3-(1-(2,3-dichlorophenyl)ethyl)-1-ethyl-1-(1-methylpiperidin-4-yl)urea, |
| GA133 | 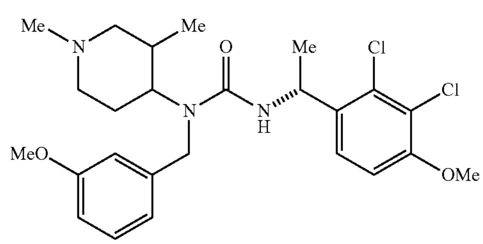 | 3-((R)-1-(2,3-dichloro-4-methoxyphenyl)ethyl)-1-(1,3-dimethylpiperidin-4-yl)-1-(3-methoxybenzyl)urea, |
| GA134 | 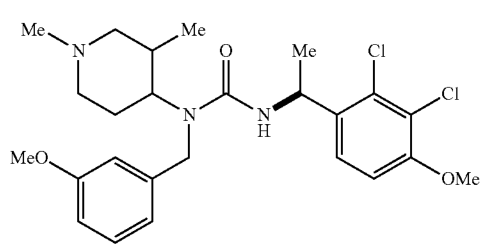 | 3-((S)-1-(2,3-dichloro-4-methoxyphenyl)ethyl)-1-(1,3-dimethylpiperidin-4-yl)-1-(3-methoxybenzyl)urea, |

-continued

| Compound No. | Chemical Structure | Chemical Name |
|---|---|---|
| GA135 | 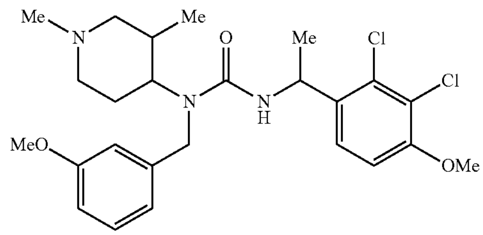 [SMILES: COc1cccc(CN(C(=O)NC(C)c2ccc(OC)c(Cl)c2Cl)C2CCN(C)CC2C)c1] | 3-(1-(2,3-dichloro-4-methoxyphenyl)ethyl)-1-(1,3-dimethylpiperidin-4-yl)-1-(3-methoxybenzyl)urea, |
| GA136 | 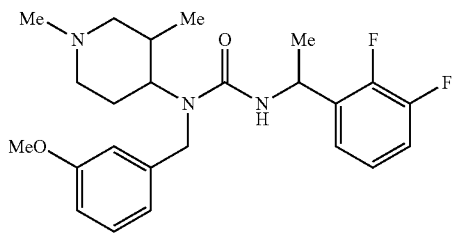 [SMILES: COc1cccc(CN(C(=O)NC(C)c2cccc(F)c2F)C2CCN(C)CC2C)c1] | 3-(1-(2,3-difluorophenyl)ethyl)-1-(1,3-dimethylpiperidin-4-yl)-1-(3-methoxybenzyl)urea, |
| GA137 | 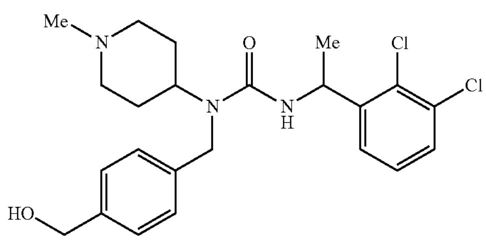 [SMILES: CC(NC(=O)N(Cc1ccc(CO)cc1)C1CCN(C)CC1)c1cccc(Cl)c1Cl] | 3-(1-(2,3-dichlorophenyl)ethyl)-1-(4-(hydroxymethyl)benzyl)-1-(1-methylpiperidin-4-yl)urea, |
| GA138 | 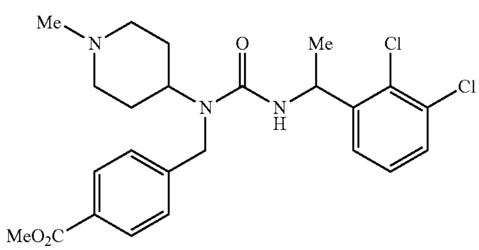 [SMILES: COC(=O)c1ccc(CN(C(=O)NC(C)c2cccc(Cl)c2Cl)C2CCN(C)CC2)cc1] | methyl 4-((3-(1-(2,3-dichlorophenyl)ethyl)-1-(1-methylpiperidin-4-yl)ureido)methyl)benzoate, |
| GA139 | 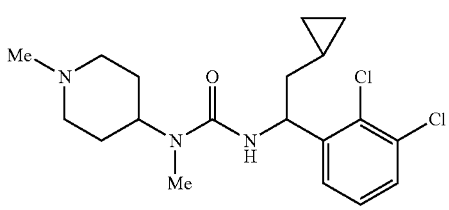 [SMILES: CN1CCC(N(C)C(=O)NC(CC2CC2)c2cccc(Cl)c2Cl)CC1] | 3-(2-cyclopropyl-1-(2,3-dichlorophenyl)ethyl)-1-methyl-1-(1-methylpiperidin-4-yl)urea, |
| GA140 | 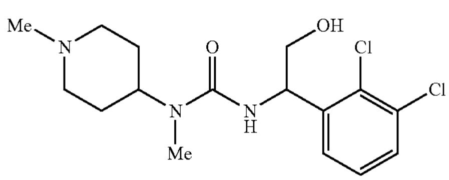 [SMILES: CN1CCC(N(C)C(=O)NC(CO)c2cccc(Cl)c2Cl)CC1] | 3-(1-(2,3-dichlorophenyl)-2-hydroxyethyl)-1-methyl-1-(1-methylpiperidin-4-yl)urea, |
| GA141 | 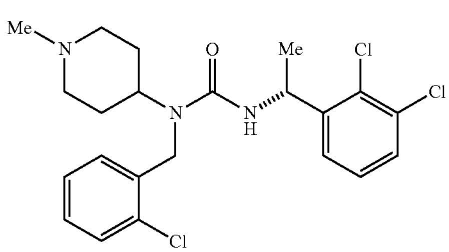 | (R)-1-(2-chlorobenzyl)-3-(1-(2,3-dichlorophenyl)ethyl)-1-(1-methylpiperidin-4-yl)urea, |

-continued

| Compound No. | Chemical Structure | Chemical Name |
|---|---|---|
| GA142 | 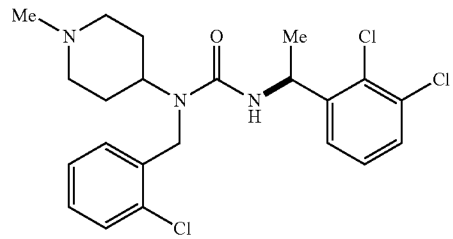 | (S)-1-(2-chlorobenzyl)-3-(1-(2,3-dichlorophenyl)ethyl)-1-(1-methylpiperidin-4-yl)urea, |
| GA143 | 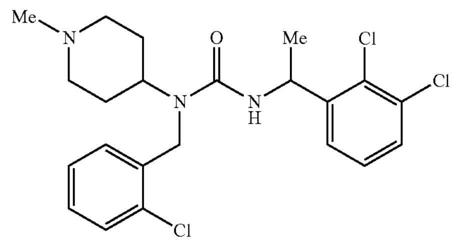 [SMILES: CC(NC(=O)N(Cc1ccccc1Cl)C1CCN(C)CC1)c1cccc(Cl)c1Cl] | 1-(2-chlorobenzyl)-3-(1-(2,3-dichlorophenyl)ethyl)-1-(1-methylpiperidin-4-yl)urea, |
| GA144 | 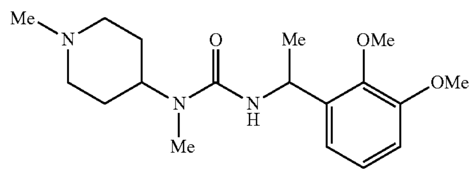 [SMILES: COc1cccc(C(C)NC(=O)N(C)C2CCN(C)CC2)c1OC] | 3-(1-(2,3-dimethoxyphenyl)ethyl)-1-methyl-1-(1-methylpiperidin-4-yl)urea, |
| GA145 | 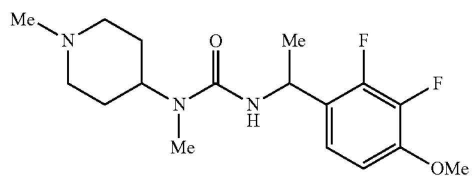 [SMILES: COc1ccc(C(C)NC(=O)N(C)C2CCN(C)CC2)c(F)c1F] | 3-(1-(2,3-difluoro-4-methoxyphenyl)ethyl)-1-methyl-1-(1-methylpiperidin-4-yl)urea, |
| GA146 | 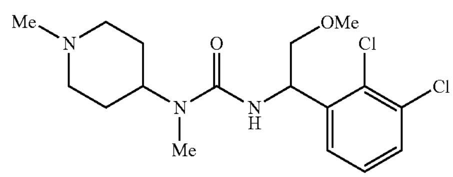 [SMILES: COCC(NC(=O)N(C)C1CCN(C)CC1)c1cccc(Cl)c1Cl] | 3-(1-(2,3-dichlorophenyl)-2-methoxyethyl)-1-methyl-1-(1-methylpiperidin-4-yl)urea, |
| GA147 | 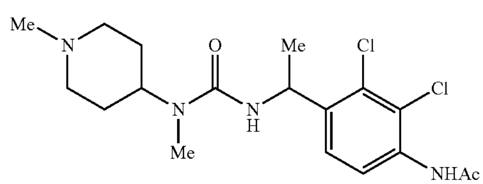 [SMILES: CC(=O)Nc1ccc(C(C)NC(=O)N(C)C2CCN(C)CC2)c(Cl)c1Cl] | N-(2,3-dichloro-4-(1-(3-methyl-3-(1-methylpiperidin-4-yl)ureido)ethyl)phenyl)acetamide, |
| GA148 | 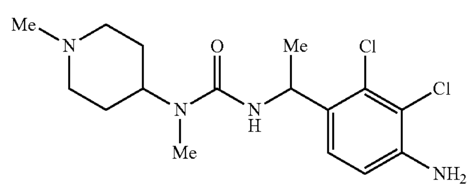 [SMILES: CC(NC(=O)N(C)C1CCN(C)CC1)c1ccc(N)c(Cl)c1Cl] | 3-(1-(4-amino-2,3-dichlorophenyl)ethyl)-1-methyl-1-(1-methylpiperidin-4-yl)urea, |
| GA149 | 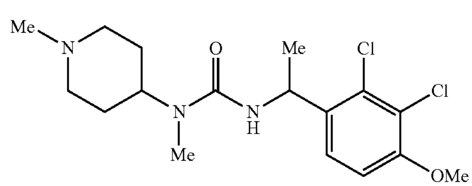 [SMILES: COc1ccc(C(C)NC(=O)N(C)C2CCN(C)CC2)c(Cl)c1Cl] | 3-(1-(2,3-dichloro-4-methoxyphenyl)ethyl)-1-methyl-1-(1-methylpiperidin-4-yl)urea, |

-continued

| Compound No. | Chemical Structure | Chemical Name |
|---|---|---|
| GA150 | 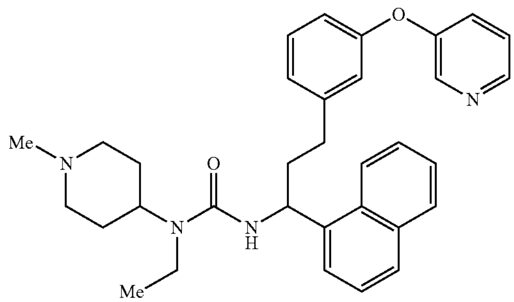 [SMILES: CCN(C(=O)NC(CCc1cccc(Oc2cccnc2)c1)c1cccc2ccccc12)C1CCN(C)CC1] | 1-ethyl-1-(1-methylpiperidin-4-yl)-3-(1-(naphthalen-1-yl)-3-(3-(pyridin-3-yloxy)phenyl)propyl)urea, |
| GA151 | 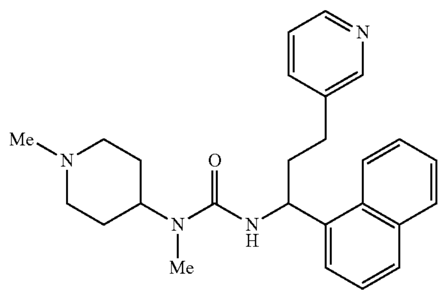 [SMILES: CN1CCC(N(C)C(=O)NC(CCc2cccnc2)c2cccc3ccccc23)CC1] | 1-methyl-1-(1-methylpiperidin-4-yl)-3-(1-(naphthalen-1-yl)-3-(pyridin-3-yl)propyl)urea, |
| GA152 | 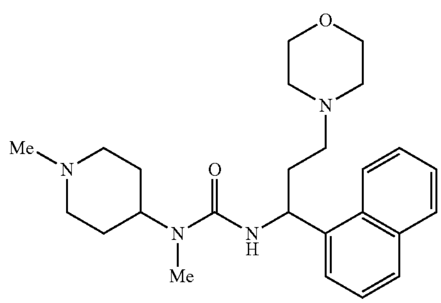 [SMILES: CN1CCC(N(C)C(=O)NC(CCN2CCOCC2)c2cccc3ccccc23)CC1] | 1-methyl-1-(1-methylpiperidin-4-yl)-3-(3-morpholino-1-(naphthalen-1-yl)propyl)urea, |
| GA153 | 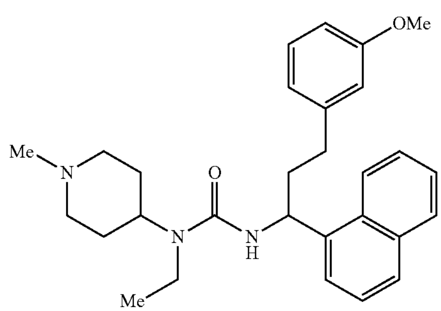 [SMILES: CCN(C(=O)NC(CCc1cccc(OCc2ccccc2)c1)c1cccc2ccccc12)C1CCN(C)CC1] | 1-ethyl-3-(3-(3-methoxyphenyl)-1-(naphthalen-1-yl)propyl)-1-(1-methylpiperidin-4-yl)urea, |
| GA154 | 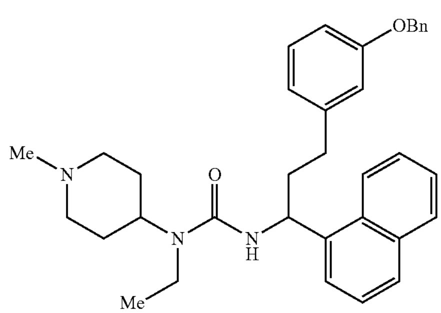 | 3-(3-(3-(benzyloxy)phenyl)-1-(naphthalen-1-yl)propyl)-1-ethyl-1-(1-methylpiperidin-4-yl)urea, |

-continued

| Compound No. | Chemical Structure | Chemical Name |
|---|---|---|
| GA155 | 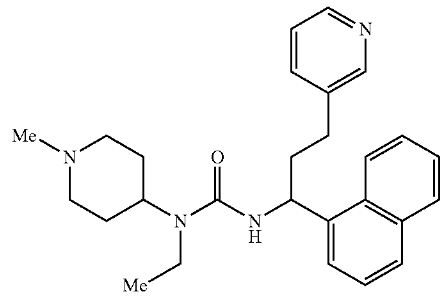 [SMILES: CCN(C(=O)NC(CCc1cccnc1)c1cccc2ccccc12)C1CCN(C)CC1] | 1-ethyl-1-(1-methylpiperidin-4-yl)-3-(1-(naphthalen-1-yl)-3-(pyridin-3-yl)propyl)urea, |
| GA156 | 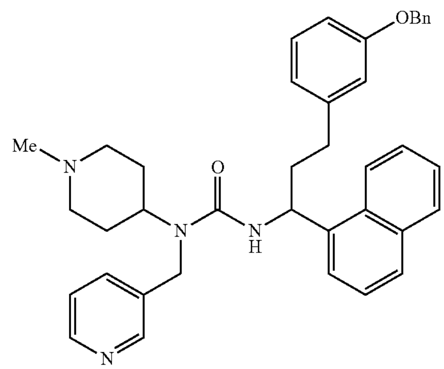 [SMILES: CN1CCC(N(Cc2cccnc2)C(=O)NC(CCc2cccc(OCc3ccccc3)c2)c2cccc3ccccc23)CC1] | 3-(3-(3-(benzyloxy)phenyl)-1-(naphthalen-1-yl)propyl)-1-(1-methylpiperidin-4-yl)-1-(pyridin-3-ylmethyl)urea, |
| GA157 | 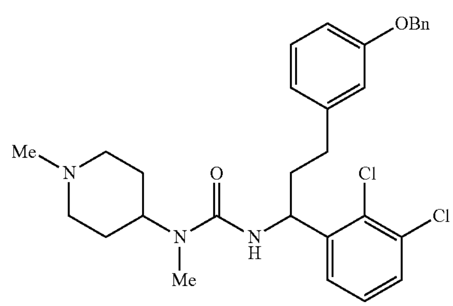 [SMILES: CN1CCC(N(C)C(=O)NC(CCc2cccc(OCc3ccccc3)c2)c2cccc(Cl)c2Cl)CC1] | 3-(3-(3-(benzyloxy)phenyl)-1-(2,3-dichlorophenyl)propyl)-1-methyl-1-(1-methylpiperidin-4-yl)urea, |
| GA158 | 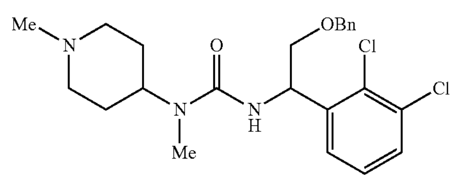 [SMILES: CN1CCC(N(C)C(=O)NC(COCc2ccccc2)c2cccc(Cl)c2Cl)CC1] | 3-(2-(benzyloxy)-1-(2,3-dichlorophenyl)ethyl)-1-methyl-1-(1-methylpiperidin-4-yl)urea, |
| GA159 | 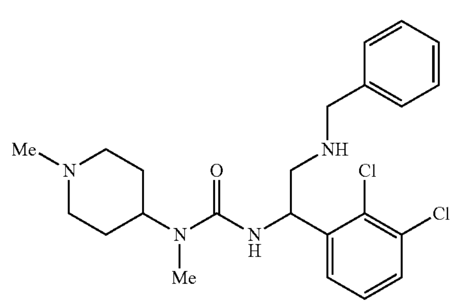 [SMILES: CN1CCC(N(C)C(=O)NC(CNCc2ccccc2)c2cccc(Cl)c2Cl)CC1] | 3-(2-(benzylamino)-1-(2,3-dichlorophenyl)ethyl)-1-methyl-1-(1-methylpiperidin-4-yl)urea, |

| Compound No. | Chemical Structure | Chemical Name |
|---|---|---|
| GA160 | 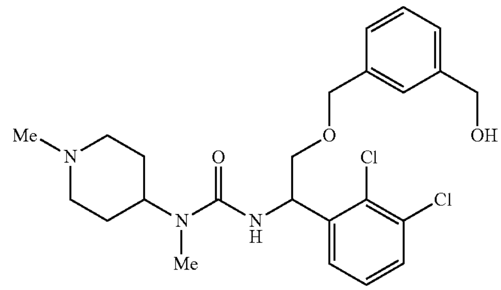 [SMILES: CN1CCC(N(C)C(=O)NC(COCc2cccc(CO)c2)c2cccc(Cl)c2Cl)CC1] | 3-(1-(2,3-dichlorophenyl)-2-((3-(hydroxymethyl)benzyl)oxy)ethyl)-1-methyl-1-(1-methylpiperidin-4-yl)urea, |
| GA161 | 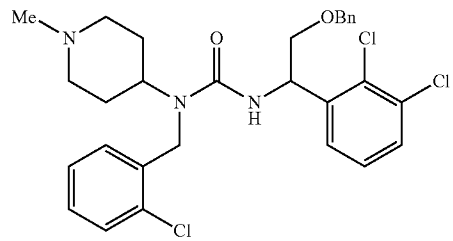 [SMILES: CN1CCC(N(Cc2ccccc2Cl)C(=O)NC(COCc2ccccc2)c2cccc(Cl)c2Cl)CC1] | 3-(2-(benzyloxy)-1-(2,3-dichlorophenyl)ethyl)-1-(2-chlorobenzyl)-1-(1-methylpiperidin-4-yl)urea, |
| GA162 | 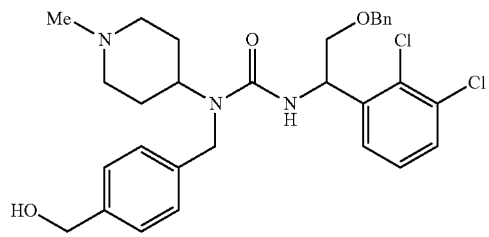 [SMILES: CN1CCC(N(Cc2ccc(CO)cc2)C(=O)NC(COCc2ccccc2)c2cccc(Cl)c2Cl)CC1] | 3-(2-(benzyloxy)-1-(2,3-dichlorophenyl)ethyl)-1-(4-(hydroxymethyl)benzyl)-1-(1-methylpiperidin-4-yl)urea, |
| GA163 | 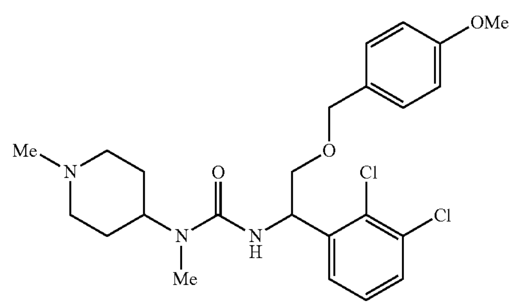 [SMILES: COc1ccc(COCC(NC(=O)N(C)C2CCN(C)CC2)c2cccc(Cl)c2Cl)cc1] | 3-(1-(2,3-dichlorophenyl)-2-((4-methoxybenzyl)oxy)ethyl)-1-methyl-1-(1-methylpiperidin-4-yl)urea, |
| GA164 | 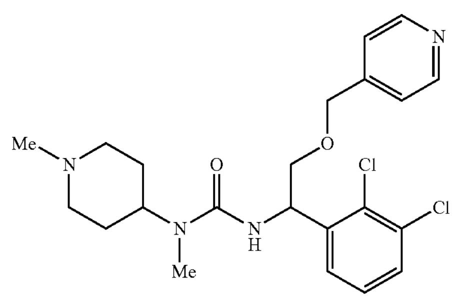 [SMILES: CN1CCC(N(C)C(=O)NC(COCc2ccncc2)c2cccc(Cl)c2Cl)CC1] | 3-(1-(2,3-dichlorophenyl)-2-(pyridin-4-ylmethoxy)ethyl)-1-methyl-1-(1-methylpiperidin-4-yl)urea, |
| GA165 | 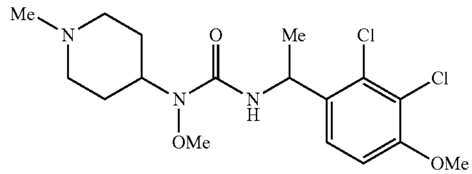 [SMILES: COc1ccc(C(C)NC(=O)N(OC)C2CCN(C)CC2)c(Cl)c1Cl] | 3-(1-(2,3-dichloro-4-methoxyphenyl)ethyl)-1-methoxy-1-(1-methylpiperidin-4-yl)urea, |

-continued

| Compound No. | Chemical Structure | Chemical Name |
|---|---|---|
| GA166 | 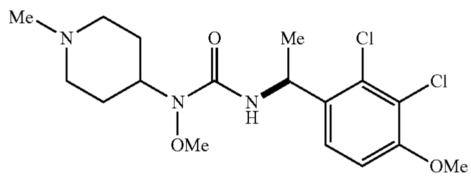 | (S)-3-(1-(2,3-dichloro-4-methoxyphenyl)ethyl)-1-methoxy-1-(1-methylpiperidin-4-yl)urea, |
| GA167 | 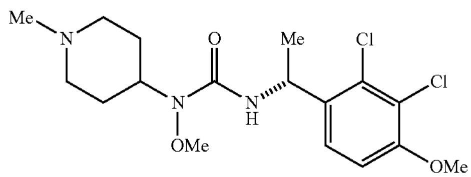 | (R)-3-(1-(2,3-dichloro-4-methoxyphenyl)ethyl)-1-methoxy-1-(1-methylpiperidin-4-yl)urea, |
| GA168 | 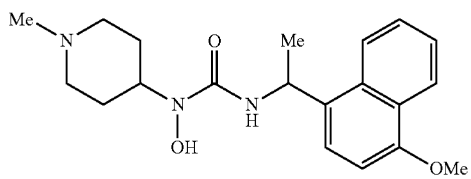 [SMILES: COc1ccc(C(C)NC(=O)N(O)C2CCN(C)CC2)c2ccccc12] | 1-hydroxy-3-(1-(4-methoxynaphthalen-1-yl)ethyl)-1-(1-methylpiperidin-4-yl)urea, |
| GA169 | 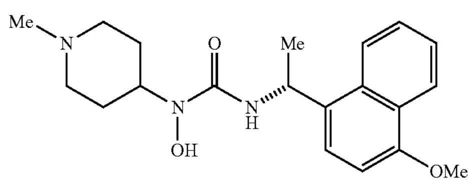 | (R)-1-hydroxy-3-(1-(4-methoxynaphthalen-1-yl)ethyl)-1-(1-methylpiperidin-4-yl)urea, |
| GA170 | 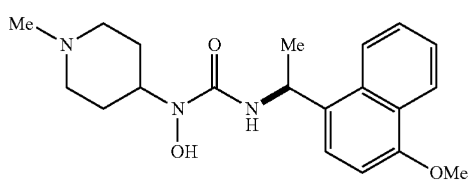 | (S)-1-hydroxy-3-(1-(4-methoxynaphthalen-1-yl)ethyl)-1-(1-methylpiperidin-4-yl)urea, |
| GA171 | 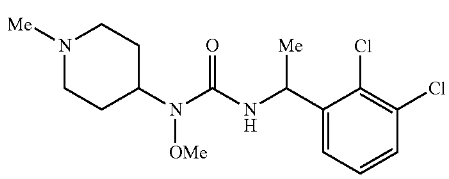 [SMILES: CON(C(=O)NC(C)c1cccc(Cl)c1Cl)C1CCN(C)CC1] | 3-(1-(2,3-dichlorophenyl)ethyl)-1-methoxy-1-(1-methylpiperidin-4-yl)urea, |
| GA172 | 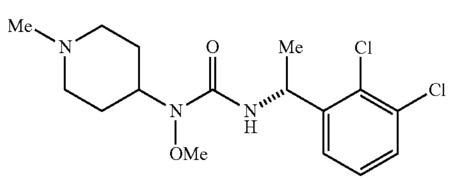 | (R)-3-(1-(2,3-dichlorophenyl)ethyl)-1-methoxy-1-(1-methylpiperidin-4-yl)urea, |
| GA173 | 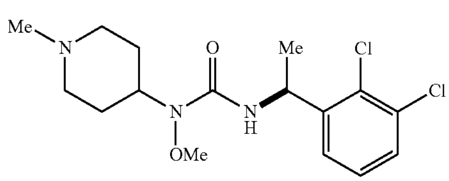 | (S)-3-(1-(2,3-dichlorophenyl)ethyl)-1-methoxy-1-(1-methylpiperidin-4-yl)urea, |

-continued

| Compound No. | Chemical Structure | Chemical Name |
|---|---|---|
| GA174 | 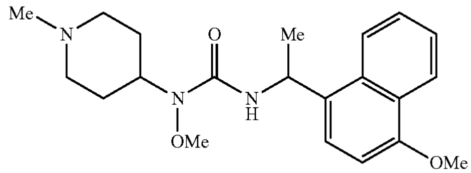 [SMILES: COc1ccc(C(C)NC(=O)N(OC)C2CCN(C)CC2)c2ccccc12] | 1-methoxy-3-(1-(4-methoxynaphthalen-1-yl)ethyl)-1-(1-methylpiperidin-4-yl)urea, |
| GA175 | 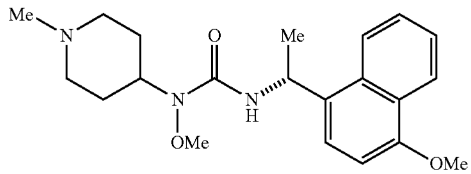 | (R)-1-methoxy-3-(1-(4-methoxynaphthalen-1-yl)ethyl)-1-(1-methylpiperidin-4-yl)urea, |
| GA176 | 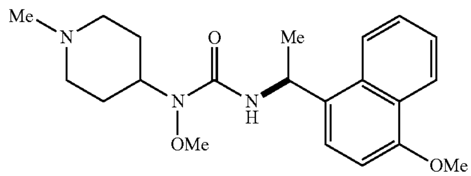 | (S)-1-methoxy-3-(1-(4-methoxynaphthalen-1-yl)ethyl)-1-(1-methylpiperidin-4-yl)urea, |
| GA177 | 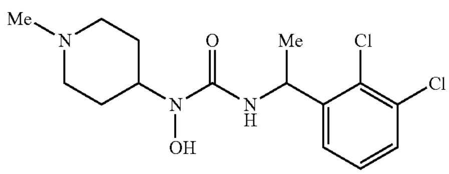 [SMILES: CC(NC(=O)N(O)C1CCN(C)CC1)c1cccc(Cl)c1Cl] | 3-(1-(2,3-dichlorophenyl)ethyl)-1-hydroxy-1-(1-methylpiperidin-4-yl)urea, |
| GA178 | 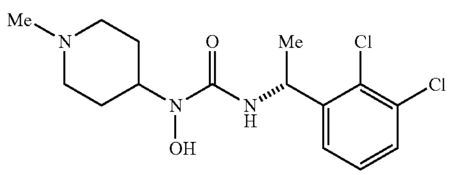 | (R)-3-(1-(2,3-dichlorophenyl)ethyl)-1-hydroxy-1-(1-methylpiperidin-4-yl)urea, |
| GA179 | 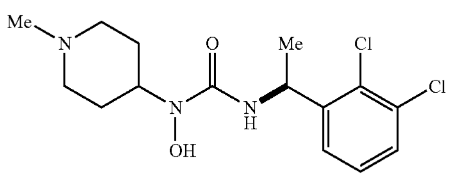 | (S)-3-(1-(2,3-dichlorophenyl)ethyl)-1-hydroxy-1-(1-methylpiperidin-4-yl)urea, |
| GA180 | 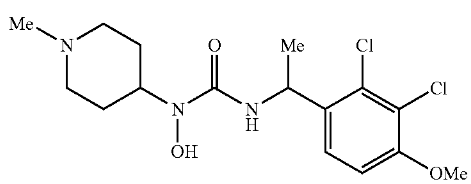 | 3-(1-(2,3-dichloro-4-methoxyphenyl)ethyl)-1-hydroxy-1-(1-methylpiperidin-4-yl)urea, |
| G181 | 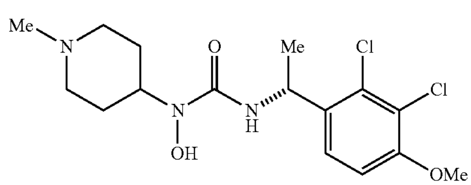 | (R)-3-(1-(2,3-dichloro-4-methoxyphenyl)ethyl)-1-hydroxy-1-(1-methylpiperidin-4-yl)urea, |

-continued

| Compound No. | Chemical Structure | Chemical Name |
|---|---|---|
| GA182 | 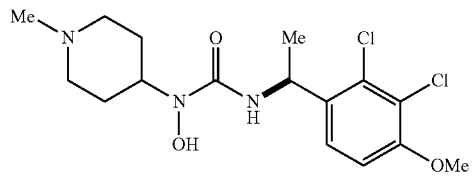 | (S)-3-(1-(2,3-dichloro-4-methoxyphenyl)ethyl)-1-hydroxy-1-(1-methylpiperidin-4-yl)urea, |
| GA183 | 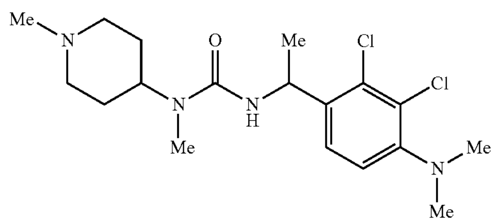 [SMILES: CC(NC(=O)N(C)C1CCN(C)CC1)c1ccc(N(C)C)c(Cl)c1Cl] | 3-(1-(2,3-dichloro-4-(dimethylamino)phenyl)ethyl)-1-methyl-1-(1-methylpiperidin-4-yl)urea, |
| GA184 | 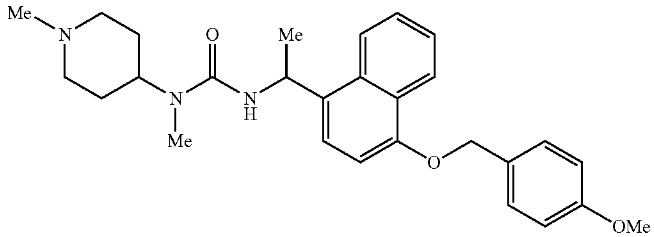 [SMILES: COc1ccc(COc2ccc(C(C)NC(=O)N(C)C3CCN(C)CC3)c3ccccc23)cc1] | 3-(1-(4-((4-methoxybenzyl)oxy)naphthalen-1-yl)ethyl)-1-methyl-1-(1-methylpiperidin-4-yl)urea, |
| G185 | 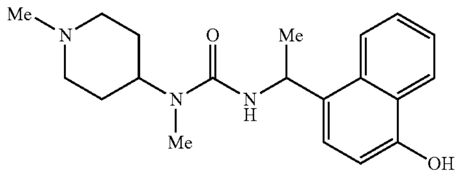 [SMILES: CC(NC(=O)N(C)C1CCN(C)CC1)c1ccc(O)c2ccccc12] | 3-(1-(4-hydroxynaphthalen-1-yl)ethyl)-1-methyl-1-(1-methylpiperidin-4-yl)urea, |
| GA186 | 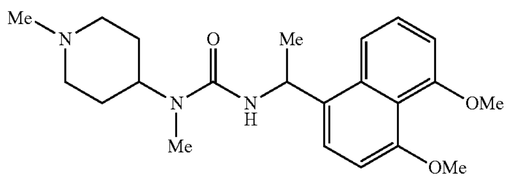 [SMILES: COc1cccc2c(C(C)NC(=O)N(C)C3CCN(C)CC3)ccc(OC)c12] | 3-(1-(4,5-dimethoxynaphthalen-1-yl)ethyl)-1-methyl-1-(1-methylpiperidin-4-yl)urea, |
| GA187 | 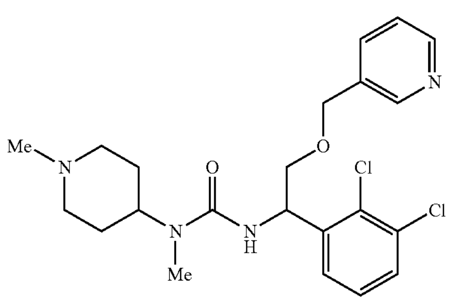 [SMILES: CN1CCC(N(C)C(=O)NC(COCc2cccnc2)c2cccc(Cl)c2Cl)CC1] | 3-(1-(2,3-dichlorophenyl)-2-(pyridin-3-ylmethoxy)ethyl)-1-methyl-1-(1-methylpiperidin-4-yl)urea, |
| GA188 | 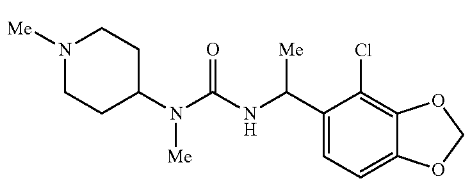 [SMILES: CC(NC(=O)N(C)C1CCN(C)CC1)c1ccc2c(c1Cl)OCO2] | 3-(1-(4-chlorobenzo[d][1,3]dioxol-5-yl)ethyl)-1-methyl-1-(1-methylpiperidin-4-yl)urea, |

-continued

| Compound No. | Chemical Structure | Chemical Name |
| --- | --- | --- |
| GA189 | 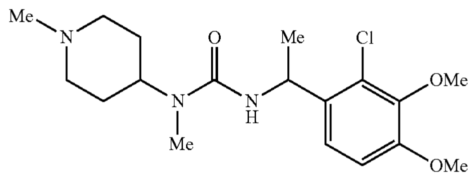 [SMILES: COc1ccc(C(C)NC(=O)N(C)C2CCN(C)CC2)c(Cl)c1OC] | 3-(1-(2-chloro-3,4-dimethoxyphenyl)ethyl)-1-methyl-1-(1-methylpiperidin-4-yl)urea, |
| GA190 | 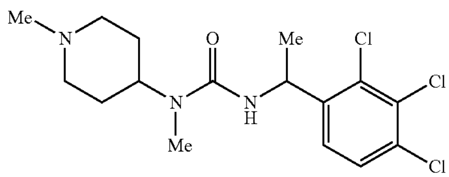 [SMILES: CC(NC(=O)N(C)C1CCN(C)CC1)c1ccc(Cl)c(Cl)c1Cl] | 1-methyl-1-(1-methylpiperidin-4-yl)-3-(1-(2,3,4-trichlorophenyl)ethyl)urea, |
| GA191 | 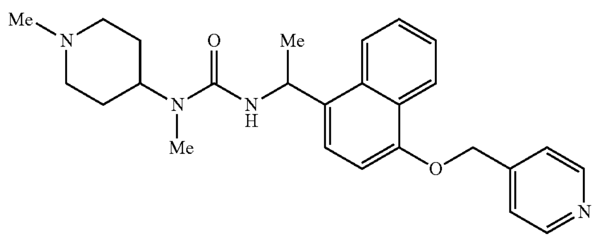 [SMILES: CC(NC(=O)N(C)C1CCN(C)CC1)c1ccc(OCc2ccncc2)c2ccccc12] | 1-methyl-1-(1-methylpiperidin-4-yl)-3-(1-(4-(pyridin-4-ylmethoxy)naphthalen-1-yl)ethyl)urea, |
| GA192 | 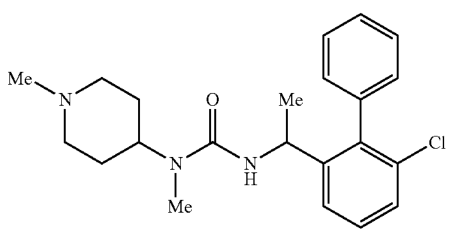 [SMILES: CC(NC(=O)N(C)C1CCN(C)CC1)c1cccc(Cl)c1-c1ccccc1] | 3-(1-(6-chloro-[1,1'-biphenyl]-2-yl)ethyl)-1-methyl-1-(1-methylpiperidin-4-yl)urea, |
| GA193 | 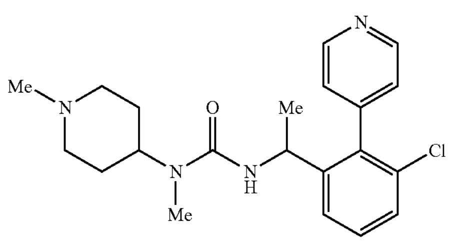 [SMILES: CC(NC(=O)N(C)C1CCN(C)CC1)c1cccc(Cl)c1-c1ccncc1] | 3-(1-(3-chloro-2-(pyridin-4-yl)phenyl)ethyl)-1-methyl-1-(1-methylpiperidin-4-yl)urea, |
| GA194 | 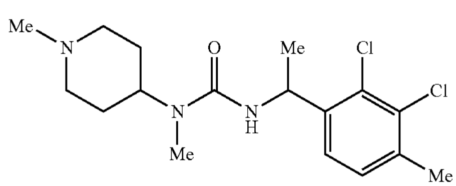 [SMILES: Cc1ccc(C(C)NC(=O)N(C)C2CCN(C)CC2)c(Cl)c1Cl] | 3-(1-(2,3-dichloro-4-methylphenyl)ethyl)-1-methyl-1-(1-methylpiperidin-4-yl)urea, |
| GA195 | 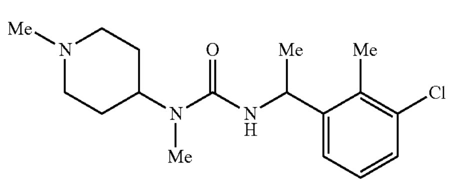 [SMILES: Cc1c(Cl)cccc1C(C)NC(=O)N(C)C1CCN(C)CC1] | 3-(1-(3-chloro-2-methylphenyl)ethyl)-1-methyl-1-(1-methylpiperidin-4-yl)urea, |

| Compound No. | Chemical Structure | Chemical Name |
|---|---|---|
| GA196 | 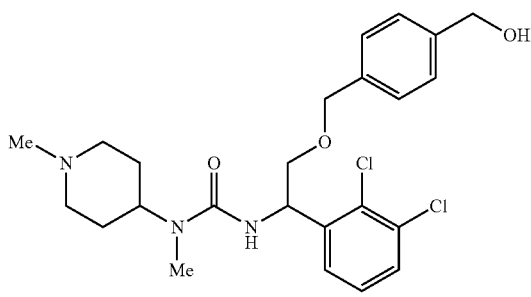 [SMILES: CN1CCC(N(C)C(=O)NC(COCc2ccc(CO)cc2)c2cccc(Cl)c2Cl)CC1] | 3-(1-(2,3-dichlorophenyl)-2-((4-(hydroxymethyl)benzyl)oxy)ethyl)-1-methyl-1-(1-methylpiperidin-4-yl)urea, |
| GA197 | 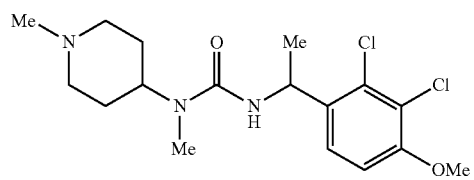 [SMILES: COc1ccc(C(C)NC(=O)N(C)C2CCN(C)CC2)c(Cl)c1Cl] | 3-(1-(2,3-dichloro-4-methoxyphenyl)ethyl)-1-methyl-1-(1-methylpiperidin-4-yl)urea, |
| GA198 | 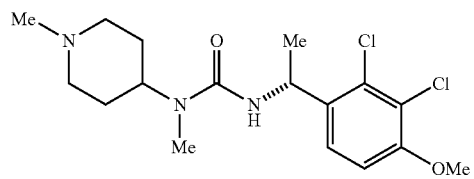 | (R)-3-(1-(2,3-dichloro-4-methoxyphenyl)ethyl)-1-methyl-1-(1-methylpiperidin-4-yl)urea, |
| GA199 | 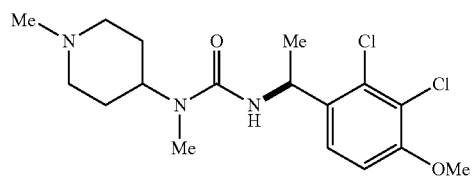 | (S)-3-(1-(2,3-dichloro-4-methoxyphenyl)ethyl)-1-methyl-1-(1-methylpiperidin-4-yl)urea, |
| GA200 | 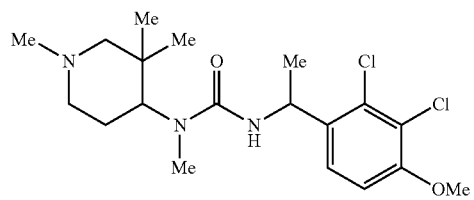 | 3-(1-(2,3-dichloro-4-methoxyphenyl)ethyl)-1-methyl-1-(1,3,3-trimethylpiperidin-4-yl)urea, |
| GA201 | 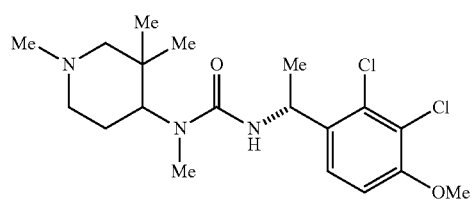 | 3-((R)-1-(2,3-dichloro-4-methoxyphenyl)ethyl)-1-methyl-1-(1,3,3-trimethylpiperidin-4-yl)urea, |
| GA202 | 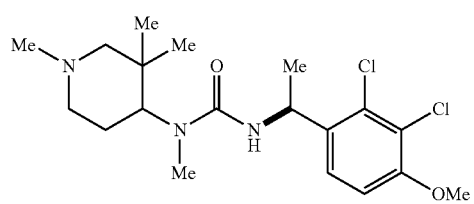 | 3-((S)-1-(2,3-dichloro-4-methoxyphenyl)ethyl)-1-methyl-1-(1,3,3-trimethylpiperidin-4-yl)urea, and |

| Compound No. | Chemical Structure | Chemical Name |
|---|---|---|
| GA203 | 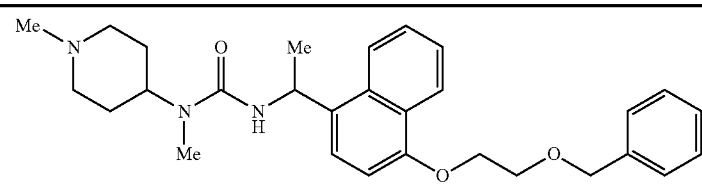 | 3-(1-(4-(2-(benzyloxy)ethoxy)naphthalen-1-yl)ethyl)-1-methyl-1-(1-methylpiperidin-4-yl)urea. |

1. Isomers

When an asymmetric center is present in a compound of formula (I), hereinafter referred to as the disclosed compounds, the compound may exist in the form of optical isomers (enantiomers). In some forms, the disclosed compounds and compositions can comprise enantiomers and mixtures, including racemic mixtures of the compounds of formula (I). In some forms, for compounds of formula (I) that contain more than one asymmetric center, the disclosed compounds and compositions can comprise diastereomeric forms (individual diastereomers and mixtures thereof) of compounds. When a compound of formula (I) contains an alkenyl group or moiety, geometric isomers may arise.

2. Tautomeric Forms

The disclosed compositions and compounds comprise the tautomeric forms of compounds of formula (I). Where structural isomers are interconvertible via a low energy barrier, tautomeric isomerism (tautomerism) can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

3. Salts

The disclosed compositions and compounds can be used in the form of salts derived from inorganic or organic acids. Depending on the particular compound, a salt of the compound can be advantageous due to one or more of the salt's physical properties, such as enhanced pharmaceutical stability in differing temperatures and humidities, or a desirable solubility in water or oil. In some instances, a salt of a compound also can be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound, such as the disclosed compounds, with an acid whose anion, or a base whose cation, is generally considered suitable for human consumption. Pharmaceutically acceptable salts are particularly useful as products of the disclosed methods because of their greater aqueous solubility relative to the parent compound. For use in medicine, the salts of the disclosed compounds are non-toxic "pharmaceutically acceptable salts." Salts encompassed within the term "pharmaceutically acceptable salts" refer to non-toxic salts of the disclosed compounds which are generally prepared by reacting the free base with a suitable organic or inorganic acid.

Suitable pharmaceutically acceptable acid addition salts of the disclosed compounds, when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclylic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Furthermore, where the disclosed compounds carry an acidic moiety, suitable pharmaceutically acceptable salts thereof can include alkali metal salts, e.g., sodium or potassium salts; alkaline earth metal salts, e.g., copper, calcium or magnesium salts; and salts formed with suitable organic ligands, e.g., quaternary ammonium salts. In some forms, base salts are formed from bases which form non-toxic salts, including aluminum, arginine, benzathine, choline, diethylamine, diolamine, glycine, lysine, meglumine, olamine, tromethamine and zinc salts.

Organic salts can be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl (C1-C6) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others. In some forms, hemisalts of acids and bases can also be formed, for example, hemisulphate and hemicalcium salts. The disclosed compounds can exist in both unsolvated and solvated forms. A "solvate" as used herein is a nonaqueous solution or dispersoid in which there is a noncovalent or easily dispersible combination between solvent and solute, or dispersion means and disperse phase.

4. Adducts

Also disclosed are so-called "adducts" of the disclosed compounds. An representive type of adduct can be Lewis acid adduct. Lewis acid is a molecular entity (and the corresponding chemical species) that is an electron-pair acceptor and therefore able to react with a Lewis base to form a Lewis adduct, by sharing the electron pair furnished by the Lewis base. An illustrative example is given by the reaction of trimethylboron and ammonia to give the adduct $Me_3BNH_3$. Typical Lewis acids are boron trihalides, for example, boron trifluoride. Thus, the disclosed compounds encompass boron trihalides adduct, for example, boron trifluoride adduct.

5. Isotopes

Also disclosed are isotopically labeled compounds, which are identical to those compounds recited in formula (I), but for the fact that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Disclosed compounds, prodrugs thereof, and pharmaceutically acceptable salts of said compounds or of said prodrugs which contain the aforementioned isotopes and/or other isotopes of other atoms are contemplated. Certain isotopically labeled disclosed compounds, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of formula (I) (and other disclosed compounds) and prodrugs thereof can generally be prepared by carrying out the procedures disclosed in the Schemes and/or in the Examples and Preparations below, by substituting a readily available isotopically labeled reagent for a non-isotopically labeled reagent.

6. General Synthetic Schemes

The compounds of the formula (I) (and other disclosed compounds), or their pharmaceutically acceptable salts or adducts, can be prepared by the methods as illustrated by examples described in the "Examples" section, together with synthetic methods known in the art of organic chemistry, or modifications and derivatisations that are familiar to those of ordinary skill in the art. The starting materials used herein are commercially available or can be prepared by routine methods known in the art (such as those methods disclosed in standard reference books such as the Compendium of Organic Synthesis Methods, Vol. I-VI (published by Wiley-Interscience)). Preferred methods include, but are not limited to, those described below. During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, T. W. Greene and P. G. M. Wuts, Protective Groups in Organic Chemistry, John Wiley & Sons, 1999, and P. G. M. Wuts and T. W. Greene, Protective Groups in Organic Chemistry, John Wiley & Sons, 2006, which are hereby incorporated by reference.

Isolation and purification of the products is accomplished by standard procedures, which are known to a chemist of ordinary skill.

7. Definition of Terms

The term "alkyl" refers to a linear or branched-chain saturated hydrocarbyl substituent (i.e., a substituent obtained from a hydrocarbon by removal of a hydrogen) containing from one to twenty carbon atoms; in one embodiment from one to twelve carbon atoms; in another embodiment, from one to ten carbon atoms; in another embodiment, from one to six carbon atoms; and in another embodiment, from one to four carbon atoms. Examples of such substituents include methyl, ethyl, propyl (including n-propyl and isopropyl), butyl (including n-butyl, isobutyl, sec-butyl and tert-butyl), pentyl, iso-amyl, hexyl and the like.

The term "alkenyl" refers to a linear or branched-chain hydrocarbyl substituent containing one or more double bonds and from two to twenty carbon atoms; in another embodiment, from two to twelve carbon atoms; in another embodiment, from two to six carbon atoms; and in another embodiment, from two to four carbon atoms. Examples of alkenyl include ethenyl (also known as vinyl), allyl, propenyl (including 1-propenyl and 2-propenyl) and butenyl (including 1-butenyl, 2-butenyl and 3-butenyl). The term "alkenyl" embraces substituents having "cis" and "trans" orientations, or alternatively, "E" and "Z" orientations.

The term "benzyl" refers to methyl radical substituted with phenyl, i.e., the following structure:

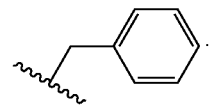 [SMILES: *Cc1ccccc1]

The term "carbocyclic ring" refers to a saturated cyclic, partially saturated cyclic, or aromatic ring containing from 3 to 14 carbon ring atoms ("ring atoms" are the atoms bound together to form the ring). A carbocyclic ring typically contains from 3 to 10 carbon ring atoms. Examples include cyclopropyl, cyclobutyl, cyclopentyl, cyclopentenyl, cyclopentadienyl, cyclohexyl, cyclohexenyl, cyclohexadienyl, and phenyl. A "carbocyclic ring system" alternatively may be 2 or 3 rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluorenyl, and decalinyl.

The term "heterocyclic ring" refers to a saturated cyclic, partially saturated cyclic, or aromatic ring containing from 3 to 14 ring atoms ("ring atoms" are the atoms bound together to form the ring), in which at least one of the ring atoms is a heteroatom that is oxygen, nitrogen, or sulfur, with the remaining ring atoms being independently selected from the group consisting of carbon, oxygen, nitrogen, and sulfur.

The term "cycloalkyl" refers to a saturated carbocyclic substituent having three to fourteen carbon atoms. In one embodiment, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6$-$C_{10}$ aromatic ring or to a 5-10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or to a 5-10-membered heteroaromatic ring may be optionally substituted with halogen, $C_1$-$C_6$ alkyl, $C_3$-$C_{10}$ cycloalkyl, or =O.

The term "cycloalkenyl" refers to a partially unsaturated carbocyclic substituent having three to fourteen carbon atoms, typically three to ten carbon atoms. Examples of cycloalkenyl include cyclobutenyl, cyclopentenyl, and cyclohexenyl.

A cycloalkyl or cycloalkenyl may be a single ring, which typically contains from 3 to 6 ring atoms. Examples include cyclopropyl, cyclobutyl, cyclopentyl, cyclopentenyl, cyclopentadienyl, cyclohexyl, cyclohexenyl, cyclohexadienyl, and phenyl. Alternatively, 2 or 3 rings may be fused together, such as bicyclodecanyl and decalinyl.

The term "aryl" refers to an aromatic substituent containing one ring or two or three fused rings. The aryl substituent may have six to eighteen carbon atoms. As an example, the aryl substituent may have six to fourteen carbon atoms. The term "aryl" may refer to substituents such as phenyl, naphthyl and anthracenyl. The term "aryl" also includes substituents such as phenyl, naphthyl and anthracenyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the aryl group. When such a fused aryl group is substituted with one more substituents, the one or more substituents, unless otherwise specified, are each bound to an aromatic carbon of the fused aryl group. The fused $C_4$-$C_{10}$ carbocyclic or 4-10-membered heterocyclic ring may be optionally substituted with halogen, $C_1$-$C_6$ alkyl, $C_3$-$C_{10}$ cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

In some instances, the number of carbon atoms in a hydrocarbyl substituent (e.g., alkyl, alkenyl, cycloalkyl, cycloalkenyl, aryl, etc.) is indicated by the prefix "$C_x$—$C_y$—," wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl refers to saturated cycloalkyl containing from 3 to 6 carbon ring atoms.

In some instances, the number of atoms in a cyclic substituent containing one or more heteroatoms (e.g., heteroaryl or heterocycloalkyl) is indicated by the prefix "X-Y-membered", wherein x is the minimum and y is the maximum number of atoms forming the cyclic moiety of the substituent. Thus, for example, 5-8-membered heterocycloalkyl refers to a heterocycloalkyl containing from 5 to 8 atoms, including one or more heteroatoms, in the cyclic moiety of the heterocycloalkyl.

The term "hydrogen" refers to hydrogen substituent, and may be depicted as —H.

The term "hydroxy" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "nitro" means —$NO_2$.

The term "cyano" (also referred to as "nitrile")—CN, which also may be depicted:

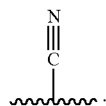

The term "carbonyl" means —C(O)—, which also may be depicted as:

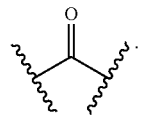

The term "amino" refers to —$NH_2$.

The term "alkylamino" refers to an amino group, wherein at least one alkyl chain is bonded to the amino nitrogen in place of a hydrogen atom. Examples of alkylamino substituents include monoalkylamino such as methylamino (exemplified by the formula —NH($CH_3$)), which may also be depicted:

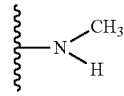

and dialkylamino such as dimethylamino, (exemplified by the formula —N($CH_3$)$_2$), which may also be depicted:

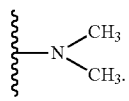

The term "aminocarbonyl" means —C(O)—$NH_2$, which also may be depicted as:

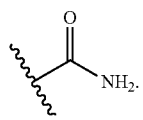

The term "halogen" refers to fluorine (which may be depicted as —F), chlorine (which may be depicted as —Cl), bromine (which may be depicted as —Br), or iodine (which may be depicted as —I). In one embodiment, the halogen is chlorine. In another embodiment, the halogen is a fluorine.

The prefix "halo" indicates that the substituent to which the prefix is attached is substituted with one or more independently selected halogen substituents. For example, haloalkyl refers to an alkyl that is substituted with at least one halogen substituent. Where more than one hydrogen is replaced with halogens, the halogens may be the identical or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 2,2,2-trifluoroethyl, difluoroethyl, pentafluoroethyl, difluoropropyl, dichloropropyl, and heptafluoropropyl. Illustrating further, "haloalkoxy" refers to an alkoxy that is substituted with at least one halogen substituent. Examples of haloalkoxy substituents include chloromethoxy, 1-bromoethoxy, fluoromethoxy, difluoromethoxy, trifluoromethoxy (also known as "perfluoromethyloxy"), and 2,2,2-trifluoroethoxy. It should be recognized that if a substituent is substituted by more than one halogen substituent, those halogen substituents may be identical or different (unless otherwise stated).

The prefix "perhalo" indicates that each hydrogen substituent on the substituent to which the prefix is attached is replaced with an independently selected halogen substituent. If all the halogen substituents are identical, the prefix may identify the halogen substituent. Thus, for example, the term "perfluoro" means that every hydrogen substituent on the substituent to which the prefix is attached is replaced with a fluorine substituent. To illustrate, the term "perfluoroalkyl" refers to an alkyl substituent wherein a fluorine substituent is in the place of each hydrogen substituent. Examples of perfluoroalkyl substituents include trifluoromethyl (—CF$_3$), perfluorobutyl, perfluoroisopropyl, perfluorododecyl, and perfluorodecyl. To illustrate further, the term "perfluoroalkoxy" refers to an alkoxy substituent wherein each hydrogen substituent is replaced with a fluorine substituent. Examples of perfluoroalkoxy substituents include trifluoromethoxy (—O—CF$_3$), perfluorobutoxy, perfluoroisopropoxy, perfluorododecoxy, and perfluorodecoxy.

The term "oxo" refers to =O.

The term "oxy" refers to an ether substituent, and may be depicted as —O—.

The term "alkoxy" refers to an alkyl linked to an oxygen, which may also be represented as —O—R, wherein the R represents the alkyl group. Examples of alkoxy include methoxy, ethoxy, propoxy and butoxy.

The term "alkylthio" means —S-alkyl. For example, "methylthio" is —S—CH$_3$. Other examples of alkylthio include ethylthio, propylthio, butylthio, and hexylthio.

The term "alkylcarbonyl" means —C(O)-alkyl. For example, "ethylcarbonyl" may be depicted as:

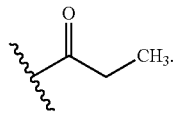

Examples of other alkylcarbonyl include methylcarbonyl, propylcarbonyl, butylcarbonyl, pentylcabonyl, and hexylcarbonyl.

The term "aminoalkylcarbonyl" means —C(O)-alkyl-NH$_2$. For example, "aminomethylcarbonyl" may be depicted as:

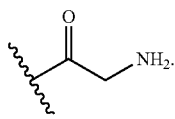 [SMILES: *C(=O)CN]

The term "alkoxycarbonyl" means —C(O)—O-alkyl. For example, "ethoxycarbonyl" may be depicted as:

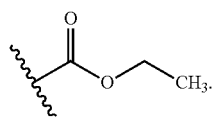 [SMILES: *C(=O)OCC]

Examples of other alkoxycarbonyl include methoxycarbonyl, ethoxycarbonyl, propoxycarbonyl, butoxycarbonyl, pentoxycarbonyl, and hexyloxycarbonyl. In another embodiment, where the carbon atom of the carbonyl is attached to a carbon atom of a second alkyl, the resulting functional group is an ester.

The terms "thio" and "thia" mean a divalent sulfur atom and such a substituent may be depicted as —S—. For example, a thioether is represented as "alkyl-thio-alkyl" or, alternatively, alkyl-S-alkyl.

The term "thiol" refers to a sulfhydryl substituent, and may be depicted as —SH.

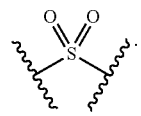

The term "thione" refers to =S.

The term "sulfonyl" refers to —S(O)$_2$—, which also may be depicted as: Thus, for example, "alkyl-sulfonyl-alkyl" refers to alkyl-S(O)$_2$-alkyl. Examples of alkylsulfonyl include methylsulfonyl, ethylsulfonyl, and propylsulfonyl.

The term "aminosulfonyl" means —S(O)$_2$—NH$_2$, which also may be depicted as:

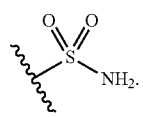

The term "sulfinyl" or "sulfoxido" means —S(O)—, which also may be depicted as:

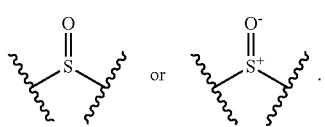

Thus, for example, "alkylsulfinylalkyl" or "alkylsulfoxidoalkyl" refers to alkyl-S(O)-alkyl. Exemplary alkylsulfinyl groups include methylsulfinyl, ethylsulfinyl, butylsulfinyl, and hexylsulfinyl.

The term "heterocycloalkyl" refers to a saturated or partially saturated ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocycloalkyl alternatively may comprise 2 or 3 rings fused together, wherein at least one such ring contains a heteroatom as a ring atom (e.g., nitrogen, oxygen, or sulfur). In a group that has a heterocycloalkyl substituent, the ring atom of the heterocycloalkyl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heterocycloalkyl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom.

The term "heterocycloalkyl" also includes substituents that are fused to a $C_6$-$C_{10}$ aromatic ring or to a 5-10-membered heteroaromatic ring, wherein a group having such a fused heterocycloalkyl group as a substituent is bound to a heteroatom of the heterocyclocalkyl group or to a carbon atom of the heterocycloalkyl group. When such a fused heterocycloalkyl group is substituted with one more substituents, the one or more substituents, unless otherwise specified, are each bound to a heteroatom of the heterocyclocalkyl group or to a carbon atom of the heterocycloalkyl group. The fused $C_6$-$C_{10}$ aromatic ring or to a 5-10-membered heteroaromatic ring may be optionally substituted with halogen, $C_1$-$C_6$ alkyl, $C_3$-$C_{10}$ cycloalkyl, or =O.

The term "heteroaryl" refers to an aromatic ring structure containing from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A heteroaryl may be a single ring or 2 or 3 fused rings. Examples of heteroaryl substituents include 6-membered ring substituents such as pyridyl, pyrazyl, pyrimidinyl, and pyridazinyl; 5-membered ring substituents such as triazolyl, imidazolyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, quinazolinyl, and 1,4-benzoxazinyl. In a group that has a heteroaryl substituent, the ring atom of the heteroaryl substituent that is bound to the group may be the at least one heteroatom, or it may be a ring carbon atom, where the ring carbon atom may be in the same ring as the at least one heteroatom or where the ring carbon atom may be in a different ring from the at least one heteroatom. Similarly, if the heteroaryl substituent is in turn substituted with a group or substituent, the group or substituent may be bound to the at least one heteroatom, or it may be bound to a ring carbon atom, where the ring carbon atom may be in the same ring as the at least one heteroatom or where the ring carbon atom may be in a different ring from the at least one heteroatom. The term "heteroaryl" also includes pyridyl N-oxides and groups containing a pyridine N-oxide ring.

Examples of single-ring heteroaryls include furanyl, dihydrofuranyl, tetradydrofuranyl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaediazolyl, oxathiazolyl, oxadiazolyl (including oxadiazolyl, 1,2,4-oxadiazolyl (also known as "azoximyl"), 1,2,5-oxadiazolyl (also known as "furazanyl"), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl (including 1,2-pyranyl or 1,4-pyranyl), dihydropyranyl, pyridinyl (also known as "azinyl"), piperidinyl, diazinyl (including pyridazinyl (also known as "1,2-diazinyl"), pyrimidinyl (also known as "1,3-diazinyl" or "pyrimidyl"), or pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, or 1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl or 1,3,5,2-oxadiazinyl), morpholinyl, azepinyl, oxepinyl, thiepinyl, and diazepinyl.

Examples of 2-fused-ring heteroaryls include, indolizinyl, pyrindinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

Examples of 3-fused-ring heteroaryls or heterocycloalkyls include 5,6-dihydro-4H-imidazo[4,5,1-ij]quinoline, 4,5-dihydroimidazo[4,5,1-hi]indole, 4,5,6,7-tetrahydroimidazo[4,5,1-jk][1]benzazepine, and dibenzofuranyl.

Other examples of fused-ring heteroaryls include benzo-fused heteroaryls such as indolyl, isoindolyl (also known as "isobenzazolyl" or "pseudoisoindolyl"), indoleninyl (also known as "pseudoindolyl"), isoindazolyl (also known as "benzpyrazolyl"), benzazinyl (including quinolinyl (also known as "1-benzazinyl") or isoquinolinyl (also known as "2-benzazinyl")), phthalazinyl, quinoxalinyl, quinazolinyl, benzodiazinyl (including cinnolinyl (also known as "1,2-benzodiazinyl") or quinazolinyl (also known as "1,3-benzodiazinyl")), benzopyranyl (including "chromanyl" or "isochromanyl"), benzothiopyranyl (also known as "thiochromanyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl," "thionaphthenyl," or "benzothiofuranyl"), isobenzothienyl (also known as "isobenzothiophenyl," "isothionaphthenyl," or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, or 3,1,4-benzoxazinyl), benzisoxazinyl (including 1,2-benzisoxazinyl or 1,4-benzisoxazinyl), tetrahydroisoquinolinyl, carbazolyl, xanthenyl, and acridinyl.

The term "heteroaryl" also includes substituents such as pyridyl and quinolinyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the heteroaryl group or to a heteroatom of the heteroaryl group. When such a fused heteroaryl group is substituted with one more substituents, the one or more substituents, unless otherwise specified, are each bound to an aromatic carbon of the heteroaryl group or to a heteroatom of the heteroaryl group. The fused $C_4$-$C_{10}$ carbocyclic or 4-10-membered heterocyclic ring may be optionally substituted with halogen, $C_1$-$C_6$ alkyl, $C_3$-$C_{10}$ cycloalkyl, or =O.

The term "ethylene" refers to the group —$CH_2$—$CH_2$—. The term "ethynelene" refers to the group —CH=CH—. The term "propylene" refers to the group —$CH_2$—$CH_2$—$CH_2$—. The term "butylene" refers to the group —$CH_2$—$CH_2$—$CH_2$—$CH_2$—. The term "methylenoxy" refers to the group —$CH_2$—O—. The term "methylenethioxy" refers to the group —$CH_2$—S—. The term "methylenamino" refers to the group —$CH_2$—N(H)—. The term "ethylenoxy" refers to the group —$CH_2$—$CH_2$—O—. The term "ethylenethioxy"

refers to the group —CH$_2$—CH$_2$—S—. The term "ethylenamino" refers to the group —CH$_2$—CH$_2$—N(H)—.

A substituent is "substitutable" if it comprises at least one carbon, sulfur, oxygen or nitrogen atom that is bonded to one or more hydrogen atoms. Thus, for example, hydrogen, halogen, and cyano do not fall within this definition. If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may be replaced separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R," wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably. If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents. If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. To illustrate, tetrazolyl (which has only one substitutable position) would be optionally substituted with up to one non-hydrogen substituent. To illustrate further, if an amino nitrogen is described as being optionally substituted with up to 2 non-hydrogen substituents, then the nitrogen will be optionally substituted with up to 2 non-hydrogen substituents if the amino nitrogen is a primary nitrogen, whereas the amino nitrogen will be optionally substituted with up to only 1 non-hydrogen substituent if the amino nitrogen is a secondary nitrogen.

A prefix attached to a multi-moiety substituent only applies to the first moiety. To illustrate, the term "alkylcycloalkyl" contains two moieties: alkyl and cycloalkyl. Thus, a C$_1$-C$_6$— prefix on C$_1$-C$_6$-alkylcycloalkyl means that the alkyl moiety of the alkylcycloalkyl contains from 1 to 6 carbon atoms; the C$_1$-C$_6$— prefix does not describe the cycloalkyl moiety. To illustrate further, the prefix "halo" on haloalkoxyalkyl indicates that only the alkoxy moiety of the alkoxyalkyl substituent is substituted with one or more halogen substituents. If the halogen substitution may only occur on the alkyl moiety, the substituent would be described as "alkoxyhaloalkyl." If the halogen substitution may occur on both the alkyl moiety and the alkoxy moiety, the substituent would be described as "haloalkoxyhaloalkyl."

When a substituent is comprised of multiple moieties, unless otherwise indicated, it is the intention for the final moiety to serve as the point of attachment to the remainder of the molecule. For example, in a substituent A-B-C, moiety C is attached to the remainder of the molecule. In a substituent A-B-C-D, moiety D is attached to the remainder of the molecule. Similarly, in a substituent aminocarbonylmethyl, the methyl moiety is attached to the remainder of the molecule, where the substituent may also be depicted as

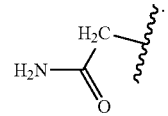

In a substituent trifluoromethylaminocarbonyl, the carbonyl moiety is attached to the remainder of the molecule, where the substituent may also be depicted as

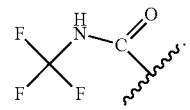

If substituents are described as being "independently selected" from a group, each substituent is selected independent of the other. Each substituent therefore may be identical to or different from the other substituent(s).

B. Pharmaceutical Compositions

Pharmaceutical compositions for preventing and/or treating a subject are further provided comprising a therapeutically effective amount of a compound of formula (I), or a pharmaceutically acceptable salt or adduct thereof, and one or more pharmaceutically acceptable excipients.

A "pharmaceutically acceptable" excipient is one that is not biologically or otherwise undesirable, i.e., the material can be administered to a subject without causing any undesirable biological effects or interacting in a deleterious manner with any of the other components of the pharmaceutical composition in which it is contained. The carrier can be selected to minimize any degradation of the active ingredient and to minimize any adverse side effects in the subject, as would be well known to one of skill in the art. The carrier can be a solid, a liquid, or both.

The disclosed compounds can be administered by any suitable route, preferably in the form of a pharmaceutical composition adapted to such a route, and in a dose effective for the treatment or prevention intended. The active compounds and compositions, for example, can be administered orally, rectally, parenterally, ocularly, inhalationaly, or topically. In particular, administration can be epicutaneous, inhalational, enema, conjunctival, eye drops, ear drops, alveolar, nasal, intranasal, vaginal, intravaginal, transvaginal, ocular, intraocular, transocular, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc.

Suitable carriers and their formulations are described in *Remington: The Science and Practice of Pharmacy* (19th ed.) ed. A.R. Gennaro, Mack Publishing Company, Easton, Pa., 1995. Oral administration of a solid dose form can be, for example, presented in discrete units, such as hard or soft capsules, pills, cachets, lozenges, or tablets, each containing a predetermined amount of at least one of the disclosed compound or compositions. In some forms, the oral administration can be in a powder or granule form. In some forms, the oral dose form is sub-lingual, such as, for example, a lozenge. In such solid dosage forms, the compounds of formula I are ordinarily combined with one or more adjuvants. Such capsules or tablets can contain a controlled-release formulation. In the case of capsules, tablets, and pills, the dosage forms also can comprise buffering agents or can be prepared with enteric coatings.

In some forms, oral administration can be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

In some forms, the disclosed compositions can comprise a parenteral dose form. "Parenteral administration" includes, for example, subcutaneous injections, intravenous injections, intraperitoneally, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Typically, an appropriate amount of a pharmaceutically acceptable carrier is used in the formulation to render the formulation isotonic. Examples of the pharmaceutically acceptable carrier include, but are not limited to, saline, Ringer's solution and dextrose solution. Other acceptable excipients include, but are not limited to, thickeners, diluents, buffers, preservatives, surface active agents and the like.

In some forms, the disclosed compositions can comprise a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation can include a compound which enhances absorption or penetration of the active ingredient through the skin or other affected areas. When the compounds and compositions are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes can also be used. Typical carriers include alcohol, water, mineral oil, liquid petrolatum, white petrolatum, glycerin, polyethylene glycol and propylene glycol. Penetration enhancers can be incorporated—see, for example, J Pharm Sci, 88 (10), 955-958, by Finnin and Morgan (October 1999).

Formulations suitable for topical administration to the eye include, for example, eye drops wherein the disclosed compound or composition is dissolved or suspended in suitable carrier. A typical formulation suitable for ocular or aural administration can be in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, can be incorporated together with a preservative, such as benzalkonium chloride. Such formulations can also be delivered by iontophoresis.

Other carrier materials and modes of administration known in the pharmaceutical art can also be used. The disclosed pharmaceutical compositions can be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

The disclosed compounds can be used, alone or in combination with other therapeutic agents, in the treatment or prevention of various conditions or disease states. The administration of two or more compounds "in combination" means that the two compounds are administered closely enough in time that the presence of one alters the biological effects of the other. The two or more compounds can be administered simultaneously, concurrently or sequentially.

Disclosed are pharmaceutical compositions comprising an effective amount of a compound of the invention or a pharmaceutically accepted salt, solvate, clathrate, or prodrug thereof; and a pharmaceutically acceptable carrier or vehicle. These compositions may further comprise additional agents. These compositions are useful for modulating the activity of ghrelin receptor, thus to improve the prevention and treatment of ghrelin receptor associated human diseases such as obesity and/or metabolic disorders.

Methods

All of the methods of the invention may be practiced with a compound of the invention alone, or in combination with other agents.

A. Treating

The above-described compounds and compositions are useful for the inhibition, reduction, prevention, and/or treatment of diseases which are pathophysiologically modulated by the ghrelin receptor. Accordingly, in some forms, disclosed are methods of preventing and/or treating diseases which are pathophysiologically modulated by the ghrelin receptor, comprising administering to a subject a therapeutically effective amount of a compound of formula (I) as disclosed above, or a pharmaceutically acceptable salt or adduct thereof.

Suitable subjects can include mammalian subjects. Mammals include, but are not limited to, canine, feline, bovine, caprine, equine, ovine, porcine, rodents, lagomorphs, primates, and the like, and encompass mammals in utero. In some forms, humans are the subjects. Human subjects can be of either gender and at any stage of development.

Diseases modulated by the ghrelin receptor, and treatable by the methods disclosed herein, include obesity, overweight, eating disorder, diabetes, metabolic syndrome, cachexia resulting from cancer, congestive heart failure, wasting due to ageing or AIDS, chronic liver failure, chronic obstructive pulmonary disease, gastrointestinal disease, gastric disorder or substance abuse. Metabolic disorders treatable by the instant methods include diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension and peripheral vascular disease. Gastric disorders treatable by the instant methods include post-operative ileus (POI), diabetic gastroparesis, and opioid induced bowel dysfunction. Gastrointestinal diseases treatable by the instant methods include irritable bowel syndrome, gastritis, acid reflux disease, gastroparesis, and functional dyspepsia. Substance abuse treatable by the instant methods includes alcohol and drug abuse, and said drug includes amphetamines, barbiturates, benzodiazepines, cocaine, methaqualone, and opioids.

In some methods the compound of Formula (I) is a ghrelin receptor modulator. In some other methods the compound of Formula (I) is a ghrelin receptor agonist. In some methods the compound of Formula (I) is a ghrelin receptor antagonist. In some methods, the compound of Formula (I) or a pharmaceutically acceptable salt or adduct thereof, is administered by one or more routes selected from the group consisting of rectal, buccal, sublingual, intravenous, subcutaneous, intradermal, transdermal, intraperitoneal, oral, eye drops, parenteral and topical administration. In some other methods, administration is accomplished by administering an oral form of the compound of Formula (I) or a pharmaceutically acceptable salt or adduct thereof A therapeutically effective amount may vary widely depending on the severity of the disease, the age and relative health of the subject, the potency of the compound used and other factors. Therapeutically effective amounts of compounds of Formula (I) may range from approximately 0.01 microgram per Kg (μg/Kg) body weight per day to about 100 mg/Kg body weight per day, or from about 0.1 μg/Kg/day to about 10 mg/Kg/day, or from about 1 μg/Kg/day to about 5 mg/Kg/day, or from about 10 μg/Kg/day to about 5 mg/Kg/day, or from about 100 μg/Kg/day to about 5 mg/Kg/day, or from about 500 μg/Kg/day to about 5 mg/Kg/day.

One of ordinary skill in the art of treating such diseases will be able, without undue experimentation and in reliance upon personal knowledge and the disclosure of this application, to ascertain a therapeutically effective amount of a compound of Formula I for a given disease. In some other forms, disclosed are methods of preventing and/or treating a subject, further comprising one or more therapeutic agents.

B. More Definitions of Terms

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

1. A, an, the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Abbreviations

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, "M" for molar, and like abbreviations).

3. About

The term "about," when used to modify the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

4. Comprise

Throughout the description and claims of this specification, the word "comprise" and variations of the word, such as "comprising" and "comprises," means "including but not limited to," and is not intended to exclude, for example, other additives, components, integers or steps.

5. Ghrelin Receptor Agonist

A ghrelin receptor agonist is any molecule that binds to and activates the Ghrelin receptor in the cells.

6. Ghrelin Receptor Antagonist

A ghrelin receptor antagonist is any molecule that binds to and inhibits the activity of Ghrelin receptor.

7. Pathophysiologically Mediated to Ghrelin Receptor

Something is "pathophysiologically mediated by the ghrelin receptor" if the ghrelin receptor is involved in the functional changes in body associated with or resulting from disease or injury.

8. Obesity

Obesity is a medical condition in which excess body fat has accumulated to the extent that it may have an adverse effect on health, leading to reduced life expectancy and/or increased health problems. Obesity treatment includes inducing weight loss, reducing bodyweight, reducing food intake, reducing appetite, increasing metabolic rate, reducing fat intake, reducing carbohydrate craving; or inducing satiety. The obesity-related disorders herein are associated with, caused by, or result from obesity. Examples of obesity-related disorders include overeating, binge eating, and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer, nicotine addiction, substance addiction and alcoholism. The compositions of the present invention are also useful for reducing the risk of secondary outcomes of obesity, such as reducing the risk of left ventricular hypertrophy.

9. Metabolic Disorder

A metabolic disorder is a disorder of metabolism, such as diabetes, Type I diabetes, Type II diabetes, inadequate glucose tolerance, insulin resistance, hyperglycemia, hyperinsulinemia, hyperlipidemia, hypertriglyceridemia, hypercholesterolemia, dyslipidemia, obesity, aging, Syndrome X, atherosclerosis, heart disease, stroke, hypertension and peripheral vascular disease.

10. Congestive Heart Failure

Congestive heart failure (CHF) is a condition in which the heart's function as a pump to deliver oxygen rich blood to the body is inadequate to meet the body's needs. Congestive heart failure can be caused by diseases that weaken the heart muscle, or diseases that cause stiffening of the heart muscles, or diseases that increase oxygen demand by the body tissue beyond the capability of the heart to deliver. Many diseases can impair the pumping action of the ventricles. For example, the muscles of the ventricles can be weakened by heart attacks or infections (myocarditis). The diminished pumping ability of the ventricles due to muscle weakening is called systolic dysfunction. After each ventricular contraction (systole) the ventricle muscles need to relax to allow blood from the atria to fill the ventricles. This relaxation of the ventricles is called diastole. Diseases such as hemochromatosis or amyloidosis can cause stiffening of the heart muscle and impair the ventricles' capacity to relax and fill; this is referred to as diastolic dysfunction. The most common cause of this is longstanding high blood pressure resulting in a thickened (hypertrophied) heart. Additionally, in some patients, although the pumping action and filling capacity of the heart may be normal, abnormally high oxygen demand by the body's tissues (for example, with hyperthyroidism) may make it difficult for the heart to supply an adequate blood flow (called high output heart failure). In some patients one or more of these factors can be present to cause congestive heart failure. Congestive heart failure can affect many organs of the body. For example, the weakened heart muscles may not be able to supply enough blood to the kidneys, which then begin to lose their normal ability to excrete salt (sodium) and water. This diminished kidney function can cause to body to retain more fluid. The lungs may become congested with fluid (pulmonary edema) and the person's ability to exercise is decreased. Fluid may likewise accumulate in the liver, thereby impairing its ability to rid the body of toxins and produce essential proteins. The intestines may become less efficient in absorbing nutrients and medicines. Over time, untreated, worsening congestive heart failure will affect virtually every organ in the body.

11. Agonism Action

Agonism action refers to the binding of a molecule to a receptor that leads to the activation of the receptor, thus triggering a cellular response similar to the cellular response for a known agonist for the receptor.

12. Antagonism Action

Antagonism action refers to the binding of a molecule to a receptor that leads to the inhibition of the receptor.

13. Modulate

To modulate, or forms thereof, means either increasing, decreasing, or maintaining a cellular activity mediated through a cellular target. It is understood that wherever one of these words is used it is also disclosed that it could be 1%, 5%, 10%, 20%, 50%, 100%, 500%, or 1000% increased from a control, or it could be 1%, 5%, 10%, 20%, 50%, or 100% decreased from a control.

14. Optional

"Optional" or "optionally" means that the subsequently described event or circumstance may or may not occur, and that the description includes instances where said event or circumstance occurs and instances where it does not.

15. Or

The word "or" or like terms as used herein means any one member of a particular list and also includes any combination of members of that list.

16. Publications

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

17. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

18. Treating

By "treating" or "treatment" is meant the medical management of a patient with the intent to cure, ameliorate, stabilize, or prevent a disease, pathological condition, or disorder. These terms include active treatment, that is, treatment directed specifically toward the improvement of a disease, pathological condition, or disorder, and also includes causal treatment, that is, treatment directed toward removal of the cause of the associated disease, pathological condition, or disorder. These terms can mean that the symptoms of the underlying disease are reduced, and/or that one or more of the underlying cellular, physiological, or biochemical causes or mechanisms causing the symptoms are reduced. It is understood that reduced, as used in this context, means relative to the state of the disease, including the molecular state of the disease, not just the physiological state of the disease. In certain situations a treatment can inadvertently cause harm. In addition, these terms include palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. These terms mean both treatment having a curing or alleviating purpose and treatment having a preventive purpose. The treatment can be made either acutely or chronically. It is understood that treatment can mean a reduction or one or more symptoms or characteristics by at least 5% 10%, 20%, 30%, 40%, 50%, 60%, 70%, 80%, 90%, 95%, 99%, 99.9%, 99.99%, 100%, relative to a control. In the context of these terms, preventing refers to the ability of a compound or composition (such as the disclosed compounds and compositions) to prevent a disease identified herein in patients diagnosed as having the disease or who are at risk of developing such disease. In this context, preventing includes the delaying the onset of the disease relative to a control. These terms do not require that the treatment in fact be effective to produce any of the intended results. It is enough that the results are intended.

19. Therapeutically Effective

The term "therapeutically effective" means that the amount of the composition used is of sufficient quantity to treat a subject as defined herein.

20. Toxicity

Toxicity is the degree to which a substance, molecule, is able to damage something, such as a cell, a tissue, an organ, or a whole organism, that has been exposed to the substance or molecule. For example, the liver, or cells in the liver, hepatocytes, can be damaged by certain substances. The methods of the present invention are preferably non-toxic.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1

1. Preparation of Compounds of Formula (I)

The following are examples of preparation of compounds of formula (I). This example is intended to be purely exemplary and is not intended to limit the disclosure.

Synthesis of Compound 1

An Intermediate Compound

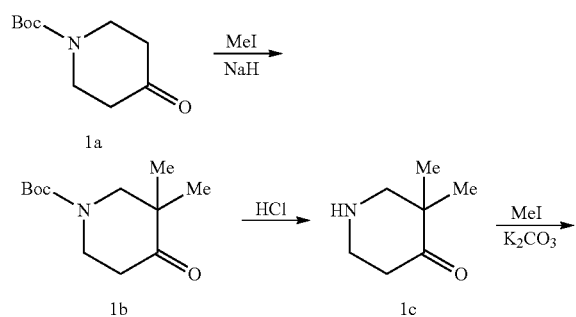

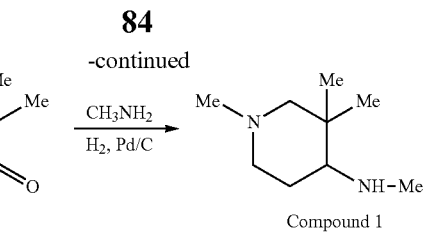

Step 1:

A solution of 1a (5 g, 25 mmol) in dry THF (10 mL) was cooled to 5° C. under nitrogen atmosphere. 60% NaH (2.4 g, 60 mmol) was added and the resulting mixture was stirred for 30 min. CH$_3$I (8.5 g, 60 mmol) was then added to the mixture and stirred at room temperature overnight. The solvent was removed under reduced pressure and the residue was dissolved in ethyl acetate and washed with brine. The organic phase was dried over anhydrous Na$_2$SO$_4$ and concentrated under reduced pressure. The residue was purified by column chromatography (silica, ethyl acetate/petroleum ether 1:15, v:v) to provide compound 1b (2.9 g, 51% yield). $^1$H-NMR (CDCl$_3$, 300 MHz): δ=3.74 (t, 2H), 3.41 (s, 2H), 2.50 (t, 2H), 1.44 (s, 9H), 1.06 (s, 6H). LC-MS: 228 [M+1]$^+$.

Step 2:

A solution of 1b (2.0 g, 8.8 mmol) in THF (30 mL) was treated with 1.5 mL of conc. HCl at room temperature. The resulting mixture was heated at 60° C. for 3 h, then cooled to room temperature. A white precipitate resulted and was collected by filtration and dried to obtain compound 1c (1.1 g, 78% yield) as HCl salt. This product was used in the next step without further purification.

Step 3:

To a mixture of 1c (1.0 g, 6.1 mmol) and K$_2$CO$_3$ (2.5 g, 18.3 mmol) in dry CH$_3$CN (20 mL) was added CH$_3$I (0.95 g, 6.7 mmol) dropwise under N$_2$ atmosphere. The mixture was stirred at room temperature overnight. The solvent was removed under reduced pressure and the residue dissolved in ethyl acetate, washed with brine, dried over anhydrous Na$_2$SO$_4$ and concentrated. The residue was purified by column chromatography (silica, ethyl acetate/petroleum ether 1:10, v:v) to provide compound 1d (0.69 g, 81% yield). $^1$H-NMR (CDCl$_3$, 300 MHz): δ=2.65 (t, 2H), 2.50 (t, 2H), 2.38 (s, 2H), 2.32 (s, 3H), 1.14 (s, 6H). LC-MS: 142 [M+1]$^+$.

Step 4:

A mixture of 1d (0.5 g, 3.5 mmol) and methyl amine (30% in MeOH, 5 mL) was hydrogenated (50 psi, 60° C.) in the presence of 5% Pd/C (50 mg) in MeOH (5 mL). After cooling, the reaction mixture was filtered, the solvent evaporated under reduced pressure and the residue purified by column chromatography (silica, MeOH/CH$_2$Cl$_2$ 1:15, v:v) to provide Compound 1 (0.21 g, 39% yield). $^1$H-NMR (CDCl$_3$, 300 MHz): δ=2.65 (t, 2H), 2.56 (d, 3H), 2.51 (t, 2H), 2.38 (s, 2H), 2.32 (s, 3H), 1.14 (s, 6H). LC-MS: 157 [M+1]$^+$.

Synthesis of Compound 2

An Intermediate Compound

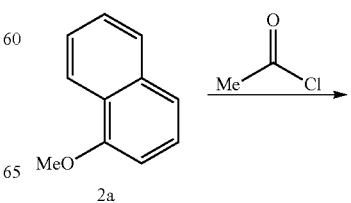

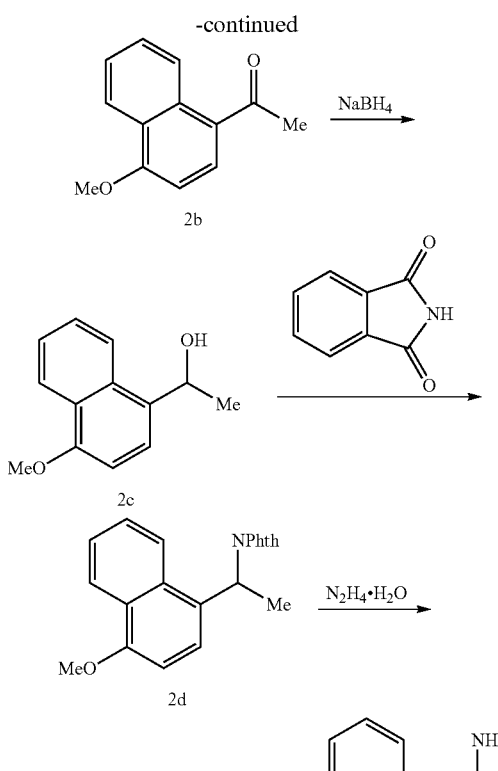

perature overnight and then concentrated. The residue was purified by column chromatography (silica, ethyl acetate/petroleum ether 1:15, v:v) to provide compound 2d (113 mg, 41% yield). $^1$H-NMR (CDCl$_3$, 300 MHz): δ=8.28-8.30 (m, 1H), 8.12 (d, 1H), 7.92 (d, 1H), 7.74-7.76 (m, 2H), 7.65-7.68 (m, 2H), 7.52-7.56 (m, 1H), 7.43-7.45 (m, 1H), 6.87 (d, 1H), 6.24 (q, 1H), 4.01 (s, 3H), 2.01 (d, 3H).

Step 4:

A solution of compound 2d (113 mg, 0.34 mmol) in MeOH (4 mL) was treated with hydrazine hydrate (98%, 68 mg, 1.36 mmol) under reflux for 2 h. The mixture was then cooled and concentrated. The residue was partitioned between CH$_2$Cl$_2$ and water. The organic phase was separated, dried with anhydrous Na$_2$SO$_4$ and concentrated to give Compound 2 (65 mg, 95% yield) as a yellow oil. $^1$H-NMR (CDCl$_3$, 300 MHz): δ=8.32 (d, 1H), 8.08 (d, 1H), 7.46-7.56 (m, 3H), 6.79 (d, 1H), 4.86 (q, 1H), 3.96 (s, 3H), 1.64 (s, 2H), 1.52 (d, 3H). LC-MS: 202 [M+1]$^+$.

Synthesis of Compound 3

An Intermediate Compound

Step 1:

To a solution of AlCl$_3$ (800 mg, 6 mmol) in dry CH$_2$Cl$_2$ (12 mL) was added acyl chloride (236 mg, 3 mmol) at 0° C. under N$_2$. The mixture was stirred for 10 min at room temperature, then compound 2a was added (474 mg, 3 mmol) and the resulting mixture stirred at room temperature overnight. Following water quench, the organic phase was separated, dried with anhydrous Na$_2$SO$_4$ and concentrated. The residue was purified by column chromatography (silica, ethyl acetate/petroleum ether 1:15, v:v) to provide compound 2b (338 mg, 56% yield) as a white solid. $^1$H-NMR (CDCl$_3$, 300 MHz): δ=9.01-9.96 (m, 1H), 8.32-8.35 (m, 1H), 8.03 (d, 1H), 7.63-7.65 (m, 1H), 7.53-7.58 (m, 1H), 6.79 (d, 1H), 4.07 (s, 3H), 2.72 (s, 3H). LC-MS: 201 [M+1]$^+$.

Step 2:

To a solution of compound 2b (167 mg, 0.84 mmol) in MeOH (5 mL) at 0° C. was added NaBH$_4$ (127 mg, 3.34 mmol). The mixture was stirred at room temperature for 2 h then the reaction was quenched with water. The reaction mixture was concentrated and partitioned between ethyl acetate and water. The organic phase was separated, dried with anhydrous Na$_2$SO$_4$ and concentrated under reduce pressure to give 2c (170 mg, 100% yield) which was used in the next step without further purification. $^1$H-NMR (CDCl$_3$, 300 MHz): δ=8.30-8.33 (m, 1H). 8.12-8.16 (m, 1H), 7.52-7.58 (m, 3H), 6.80 (d, 1H), 5.59 (q, 1H), 4.00 (s, 3H), 1.66 (d, 3H). LC-MS: 203 [M+1]$^+$.

Step 3:

To a mixture of 2c (170 mg, 0.84 mmol), phthalimide (186 mg, 1.26 mmol) and PPh$_3$ (441 mg, 1.68 mmol) in dry THF (12 mL) was added DIAD (340 mg, 1.68 mmol) at room temperature under N$_2$. The mixture was stirred at room tem- Compound 3 was prepared using a synthetic procedure analogous to that of Compound 2 to yield the target compound as a light-yellow oil (8.6 g, 55% yield). $^1$H NMR (CDCl$_3$, 300 MHz,): δ=7.42 (d, 1H), 6.87 (d, 1H), 4.52 (q, 1H), 3.90 (s, 3H), 1.66 (s, 2H), 1.36 (d, 3H). LC-MS: 220 [M+1]$^+$.

Synthesis of Compound 4

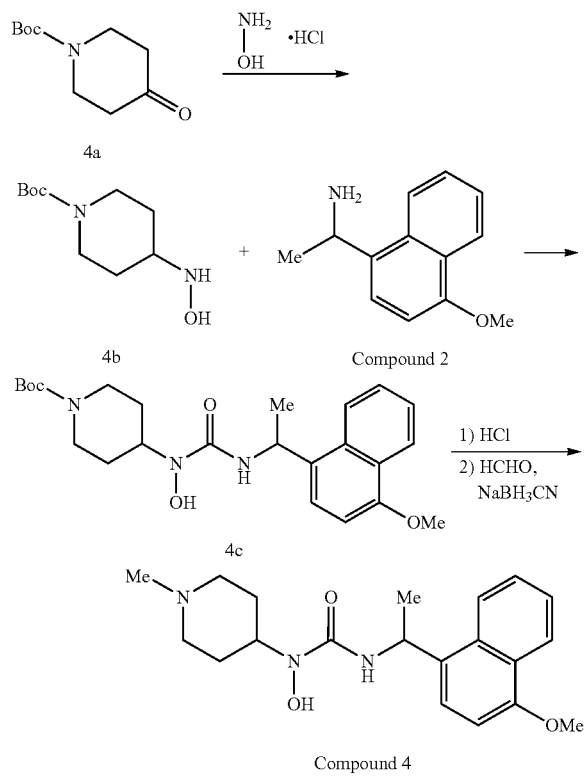

Step 1:

To a solution of 4a (1 g, 5 mmol) in MeOH (50 mL) was added acetic acid (0.5 mL, 8.7 mmol), sodium acetate (0.5 g, 6 mmol) and hydroxylamine hydrochloride (340 mg, 5 mmol), followed by NaBH$_3$CN (640 mg, 10 mmol). The mixture was stirred at room temperature overnight. The solvent was removed under reduced pressure and the residue washed with aqueous NaHCO$_3$ solution and the mixture extracted with CH$_2$Cl$_2$ (3×30). The combined organic phases were dried over anhydrous Na$_2$SO$_4$ and concentrated under reduced pressure. The residue was purified by column chromatography (silica, ethyl acetate/petroleum ether 1:1, v:v) to provide compound 4b (650 mg, 60% yield). $^1$H-NMR (CDCl$_3$, 300 MHz): δ=4.03-4.07 (m, 2H), 2.91-3.01 (m, 1H), 2.76-2.84 (m, 2H), 1.83-1.88 (m, 2H), 1.41 (s, 9H), 1.23-1.35 (m, 2H). LC-MS: 217 [M+1]$^+$.

Step 2:

To a solution of compound 2 (45 mg, 0.72 mmol) in CH$_2$Cl$_2$(30 mL) at 0° C. was added TEA (1.5 mL, 10.4 mmol) and triphosgene (210 mg, 0.72 mmol). The mixture was stirred for 15 min, then 4b (155 mg, 0.72 mmol) was added. The resulting mixture was warmed to room temperature and stirred for 30 min. Following concentration, the residue was washed with an aqueous solution of NaHCO$_3$ and extracted with CH$_2$Cl$_2$. The combined organic phases were dried with Na$_2$SO$_4$ and concentrated to provide crude urea 4c, which was used in the next step without further purification. LC-MS: 444 [M+1]$^+$.

Step 3:

To a solution of 4c (300 mg 0.92 mmol) in MeOH (20 mL) at 0° C. was added anhydrous HCl in MeOH (2N, 10 mL). The mixture was stirred at room temperature for 2 h. After concentration, the residue was dissolved in MeOH (30 mL) and sodium acetate (0.5 g, 6 mmol), acetic acid (0.5 mL, 8.7 mmol) and 38% formaldehyde solution (2 mL, 25 mmol) were added, followed by NaBH$_3$CN (87 mg, 1.3 mmol). The resulting mixture was stirred at room temperature overnight and then concentrated under reduced pressure. The residue was washed with saturated aqueous NaHCO$_3$ (40 mL) solution, and extracted with CH$_2$Cl$_2$ (3×50 mL). The combined organic phases were dried with anhydrous Na$_2$SO$_4$ and concentrated under reduced pressure to yield a residue that was purified by column chromatography (silica, MeOH/CH$_2$Cl$_2$ 1:20, v:v) to provide Compound 4 (130 mg, 50% yield) as a white solid. $^1$H-NMR (300 MHz, CDCl$_3$): δ=8.26-8.29 (m, 1H); 8.03-8.06 (m, 1H), 7.36-7.52 (m, 3H), 6.72-6.74 (d, 1H), 6.26-6.29 (d, 1H), 5.64-5.69 (m, 1H), 4.06-4.08 (m, 1H), 3.98 (s, 3H), 2.89-2.93 (m, 2H), 1.93-2.20 (m, 4H), 2.08 (s, 3H) 1.53-1.68 (m, 2H), 1.57 (d, 3H). LC-MS: 358 [M+1]

Synthesis of Compound 5

Step 1:

To a solution of 5a (5.65 g, 50 mmol) and methoxyamine (5 g, 60 mmol) in MeOH (150 mL) was added acetic acid (5 mL, 87.5 mmol), sodium acetate (5.0 g, 60 mmol), followed by NaBH$_3$CN (640 mg, 10 mmol). The mixture was stirred at room temperature for 48 h, then quenched with aqueous sat. NaHCO$_3$ (add volume). The aqueous layer was extracted with CH$_2$Cl$_2$ (3×160 mL). The combined organic phase was dried over anhydrous Na$_2$SO$_4$ and evaporated to provide product 5b (21% crude yield) as a colorless oil, which was used in the next step without further purification. LC-MS: 145 [M+1]$^+$.

Step 2:

To a solution of Compound 3 (250 mg, 1.14 mmol) in CH$_2$Cl$_2$(60 mL) at 0° C. was added TEA (3.5 ml, 25.21 mmol) and triphosgene (203 mg, 0.68 mmol). The mixture was stirred for 15 min, then crude 5b (329 mg, 2.28 mmol) was added. The resulting mixture was stirred for 30 min and evaporated. The residue was purified by column chromatography (silica, MeOH/CH$_2$Cl$_2$ 1:20, v:v) to afford Compound 5 (100 mg, 22% yield) as a white solid. $^1$H-NMR (CDCl$_3$, 300 MHz): δ=7.17 (d, 1H); 6.84 (d, 1H), 6.21-6.30 (m, 1H), 5.16-5.24 (m, 1H), 4.00-4.16 (m, 1H), 3.89 (s, 3H), 3.72 (s, 3H), 3.18-3.29 (m, 2H), 2.53 (s, 3H), 2.21-2.50 (m, 4H), 1.69-1.90 (m, 2H), 1.50 (d, 3H). LC-MS: 390 [M+1]$^+$.

Synthesis of Compound 6

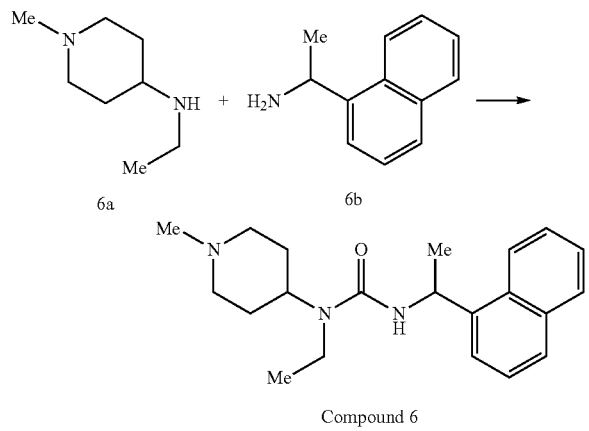

Compound 6

An analogous procedure to the last step of the synthesis of Compound 5 provided the target Compound 6 (120 mg, 61% yield) as a yellow solid. $^1$H-NMR (CDCl$_3$, 300 MHz): δ=8.14 (d, 1H); 7.91 (t, 1H), 7.78 (d, 1H), 7.47-7.56 (m, 4H), 6.57 (d, 1H), 5.63-5.72 (m, 1H), 3.83-3.97 (m, 1H), 3.16 (q, 2H), 2.75 (d, 2H), 2.12 (s, 3H), 1.84-1.91 (m, 2H), 1.55-1.66 (m, 2H), 1.49 (d, 3H), 1.40-1.48 (m, 2H), 0.99 (t, 3H). LC-MS: 340 [M+1]$^+$.

Synthesis of Compound 7

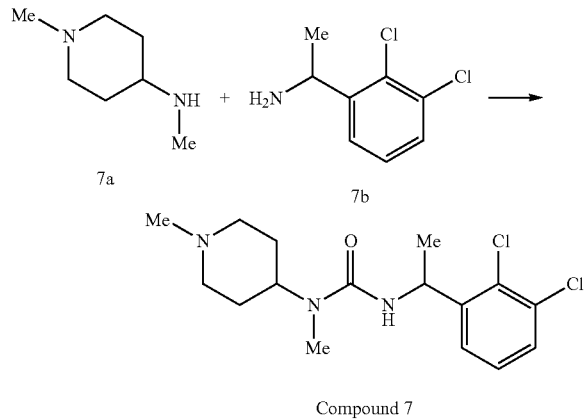

Compound 7

Following an analogous synthetic procedure to the last step in the preparation of Compound 5, compound 7 (140 mg, 91% yield) was obtained as a yellow solid. $^1$H-NMR (300 MHz, CDCl$_3$): δ=7.32-7.35 (m, 1H); 7.16-7.23 (m, 2H), 5.22-5.36 (m, 1H), 4.82 (d, 1H), 4.04-4.17 (m, 1H), 2.82-2.92 (m, 2H), 2.77 (s, 3H), 2.25 (s, 3H), 1.96-2.03 (m, 2H), 1.61-1.74 (m, 4H), 1.46 (d, 3H). LC-MS: 344 [M+1]$^+$.

Synthesis of Compound 8

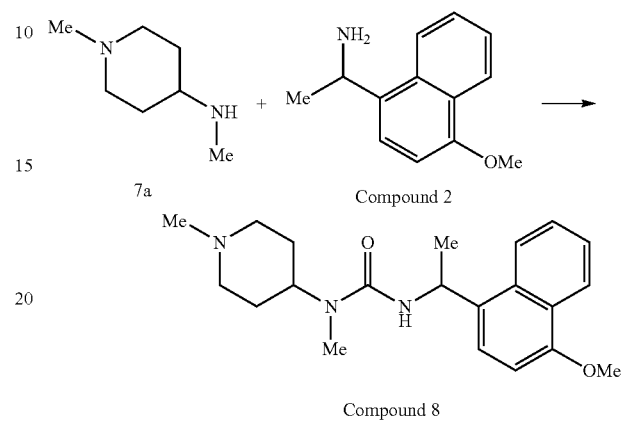

Compound 8

Following an analogous synthetic procedure to the last step in the preparation of Compound 5, compound 8 (101 mg, 28% yield) was obtained as a yellow solid. $^1$H-NMR (CDCl$_3$, 300 MHz): δ=8.30-8.32 (m, 1H), 8.09 (t, 1H), 7.43-7.48 (m, 3H), 6.77 (d, 1H), 5.72-5.76 (m, 1H), 4.56 (t, 1H), 4.36-4.38 (m, 1H), 4.00 (s, 3H), 3.12-3.15 (m, 2H), 2.64 (s, 3H), 2.36-2.39 (m, 5H), 2.00-2.03 (m, 2H), 1.60-1.66 (m, 5H); LC-MS: 356 [M+1]$^+$.

Synthesis of Compound 9

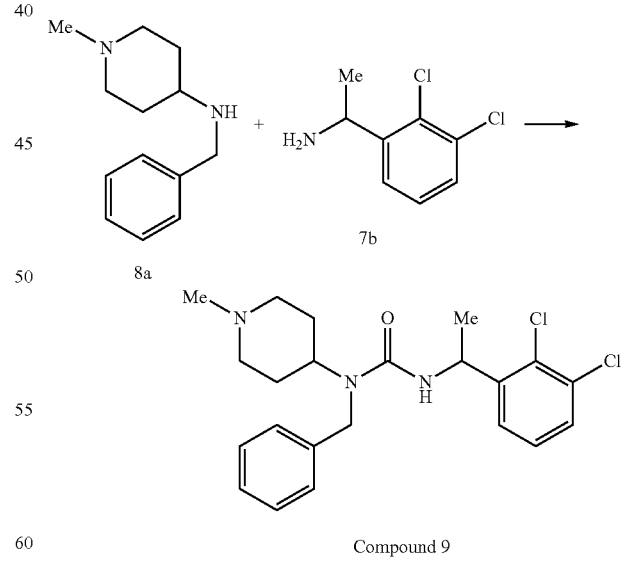

Compound 9

Following an analogous synthetic procedure to the last step in the preparation of Compound 5, compound 9 (100 mg, 64% yield) was obtained as a white solid. $^1$H-NMR (CDCl$_3$, 300 MHz): δ=7.40-7.25 (m, 6H); 7.06-7.01 (t, 1H), 6.75-6.72 (m, 1H), 5.28-5.23 (m, 1H), 4.70-4.68 (d, 1H), 4.40-4.38 (m, 3H), 2.87-2.83 (m, 2H), 2.23 (s, 3H), 2.05-2.01 (m, 2H), 1.74-1.61 (m, 4H), 1.22-1.19 (d, 3H). LC-MS: 420 [M+1]+.

Synthesis of Compound 10

7.27 (m, 3H), 7.05-7.10 (m, 1H), 6.89-6.92 (m, 1H), 5.29-5.20 (m, 1H), 4.64 (d, 1H), 4.37-4.44 (m, 3H), 2.91-3.01 (m, 2H), 2.32 (s, 3H), 2.17-2.23 (m, 2H), 1.65-1.82 (m, 4H), 1.33 (d, 3H). LC-MS: 454 [M+1]+.

Synthesis of Compound 12

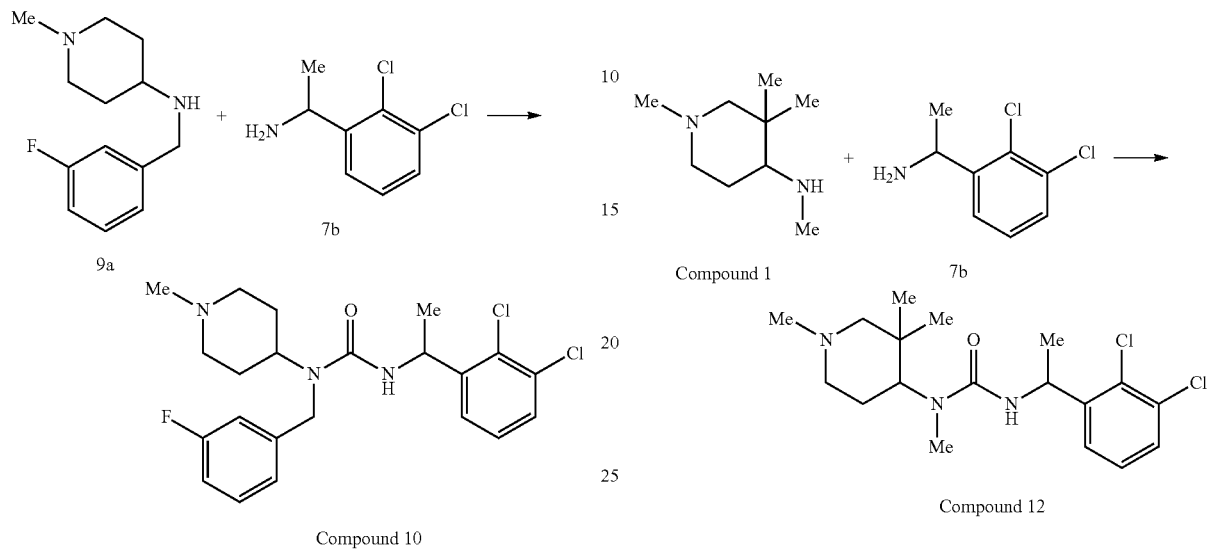

Following an analogous synthetic procedure to the last step in the preparation of Compound 5, compound 10 (176 mg, 76% yield) was obtained as a white solid. $^1$H-NMR (CDCl$_3$, 300 MHz): δ=7.28-7.37 (m, 2H); 6.97-7.11 (m, 4H), 6.81-6.85 (m, 1H), 5.24-5.29 (m, 1H), 4.67-4.70 (m, 1H), 4.30-4.47 (m, 3H), 2.90-2.98 (m, 2H), 2.16 (s, 3H), 2.10-2.21 (m, 2H), 1.31-1.98 (m, 4H), 1.22 (d, 3H). LC-MS: 438 [M+1]+.

Synthesis of Compound 11

Following an analogous synthetic procedure to the last step of the preparation of Compound 5, compound 12 (120 mg, 46% yield) was obtained as a white solid. $^1$H-NMR (CDCl$_3$, 300 MHz): δ=7.32-7.36 (m, 1H); 7.13-7.25 (m, 2H), 5.28-5.35 (m, 1H), 4.82-4.92 (m, 1H), 4.07-4.12 (m, 1H), 2.94-3.00 (m, 1H), 2.85 (s, 3H), 2.40-2.47 (m, 1H), 2.22 (s, 3H), 2.02-2.12 (m, 2H), 1.86-1.91 (m, 1H), 1.41-1.49 (m, 3H), 1.33-1.37 (m, 1H), 1.07 (s, 3H), 0.82 (d, 3H). LC-MS: 372.1 [M+1]+.

Synthesis of Compound 13

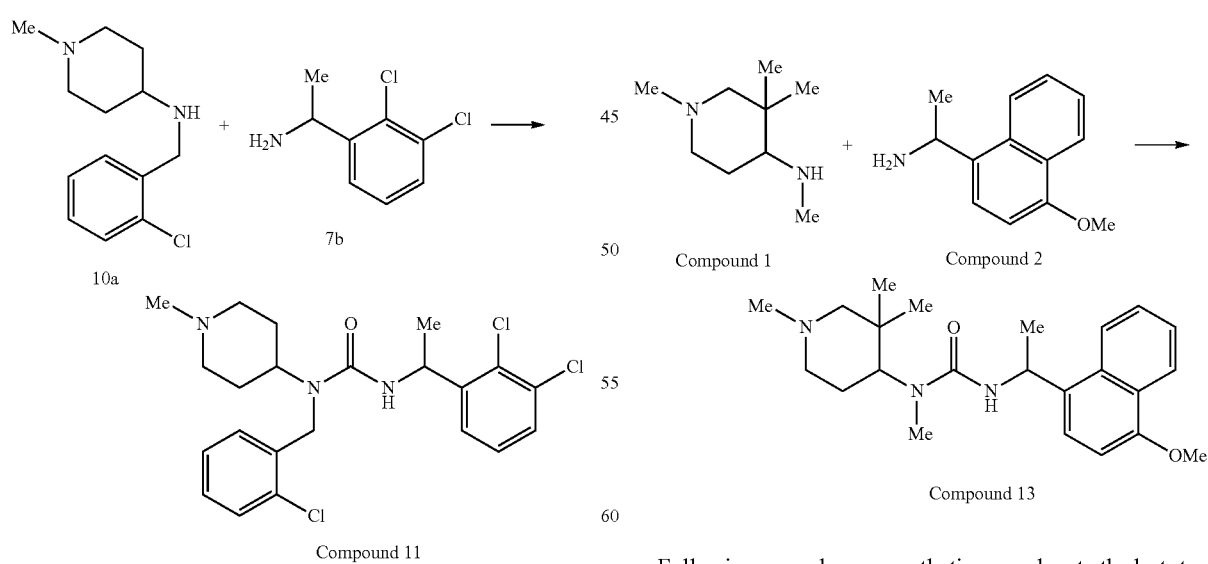

Following an analogous synthetic procedure to the last step in the preparation of Compound 5, compound 11 (105 mg, 35% yield) was obtained as a white solid. $^1$H-NMR (CDCl$_3$, 300 MHz): δ=7.40-7.42 (m, 1H), 7.29-7.31 (m, 1H), 7.25-

Following an analogous synthetic procedure to the last step of the preparation of Compound 5, compound 13 (70 mg, 36% yield) was obtained as a light yellow solid. $^1$H NMR (CDCl$_3$, 300 MHz): δ=8.28-8.31 (m, 1H), 8.09 (d, 1H), 7.26-7.54 (m, 3H), 6.77 (d, 1H), 5.70-5.79 (m, 1H), 4.56 (q, 1H), 4.16-4.28 (m, 1H), 4.00 (d, 3H), 2.96-3.00 (m, 1H), 2.67 (d, 3H), 2.45 (d, 1H), 2.25-2.26 (m, 3H), 1.92-2.11 (m, 3H), 1.63-1.67 (m, 3H), 1.40-1.48 (m, 1H), 1.05 (d, 3H), 0.90 (d, 3H); LC-MS: 384 [M+1]+

Synthesis of Compound 14

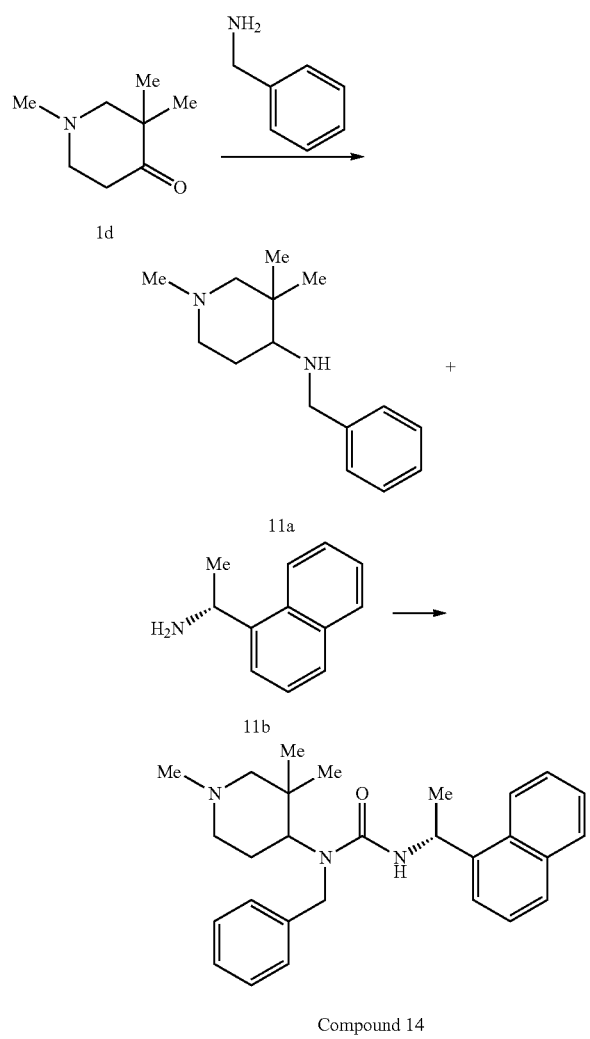

Compound 14

Step 1:

A mixture of 1d (0.5 g, 3.5 mmol) and benzyl amine (0.34 g, 3.19 mmol) in MeOH (30 mL) as stirred at room temperature for 3 h. Then NaBH$_3$CN (0.45 g, 7.0 mmol) was added and the reaction mixture was stirred at room temperature overnight. The solvent was removed under reduce pressure and the residue was dissolved in CH$_2$Cl$_2$ (50 mL). The mixture was washed with 100 mL of brine (100 mL) and the organic phases dried over Na$_2$SO$_4$ and concentrated. The residue was purified by column chromatograph (silica, MeOH:CH$_2$Cl$_2$ 1:20 to 1:10) to provide intermediate 11a (0.2 g, 27% yield) as a light yellow oil. LC-MS: 234 [M+1]+.

Step 2:

This procedure is analogous to the final step of the synthesis of Compound 5 and provided Compound 14 (80 mg, 20% yield) as a white solid. $^1$H-NMR (CDCl$_3$, 300 MHz,): δ=8.05-8.10 (m, 1H); 7.76-7.85 (m, 2H), 7.64-7.66 (m, 2H), 6.33-7.79 (m, 7H), 5.73-5.79 (m, 1H), 4.31-4.67 (m, 4H), 3.00-3.05 (m, 1H), 2.51-2.55 (m, 1H), 1.97-2.30 (m, 6H), 1.59-1.69 (m, 1H), 1.29-1.33 (m, 3H), 0.95-1.15 (m, 6H). LC-MS: 430 [M+1]+.

Synthesis of Compound 15

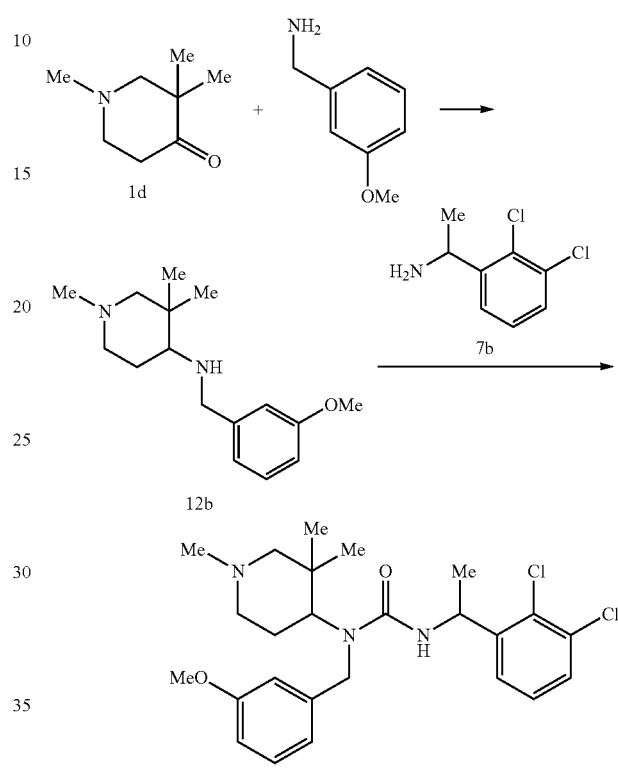

Compound 15

Step 1:

Analogous to the preparation of 11a, compound 12b was obtained (2.1 g, 63% yield) and used without further purification in the following step. LC-MS: 263 [M+1]+.

Step 2:

This step is analogous to the final step in the synthesis of Compound 5 and provided Compound 15 (140 mg, 57% yield) as a white solid. $^1$H-NMR (CDCl$_3$, 300 MHz): δ=7.22-7.31 (m, 2H); 7.09 (t, 1H), 6.79-6.95 (m, 4H), 5.15-5.30 (m, 1H), 4.64-4.78 (m, 1H), 4.36-4.46 (m, 3H), 3.76-3.79 (d, 3H), 3.94-3.96 (m, 1H), 2.39-2.42 (m, 1H), 2.19 (s, 3H), 1.98-2.05 (m, 2H), 1.20-1.25 (m, 2H), 1.07-1.09 (m, 6H), 0.86-0.97 (m, 3H). LC-MS: 378 [M+1]+.

Synthesis of Compound 16

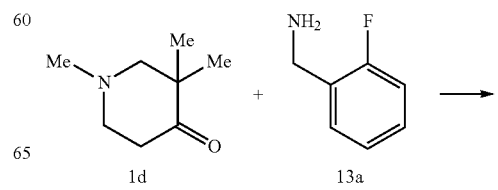

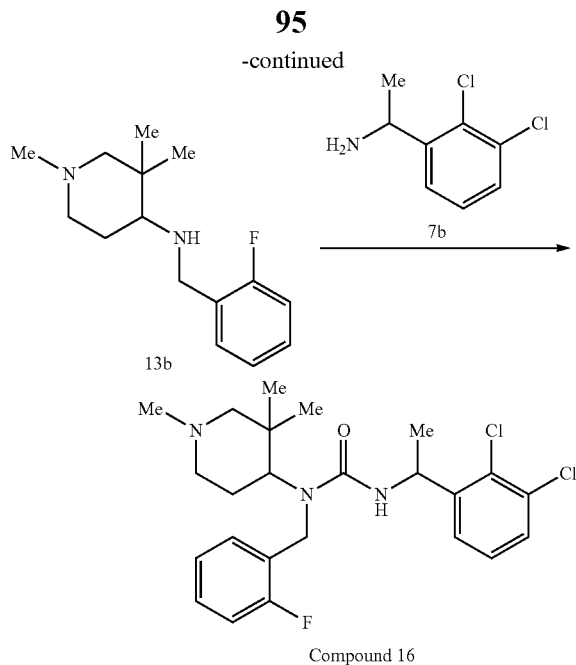

Compound 16

Step 1:
The synthesis is similar to that of 11b and provided 13b (1.0 g, 46% yield) which was used in the following step without further purification. LC-MS: 251 [M+1]⁺.

Step 2:
Compound 16 was synthesized using a procedure similar to the final step in the preparation of Compound 5. Compound 16 was obtained as a white solid (195 mg, 49% yield). ¹H NMR (CDCl₃, 300 MHz): δ=7.25-7.40 (m, 6H); 7.01-7.06 (m, 3H), 6.72-6.75 (m, 1H), 5.25-5.28 (m, 1H), 4.70 (d, 1H), 4.38-4.40 (m, 3H), 2.83-2.87 (m, 2H), 2.24 (s, 3H), 2.01-2.05 (m, 2H), 1.67-1.74 (m, 4H), 1.21 (d, 3H). LC-MS: 466 [M+1]⁺.

Synthesis of Compound 17

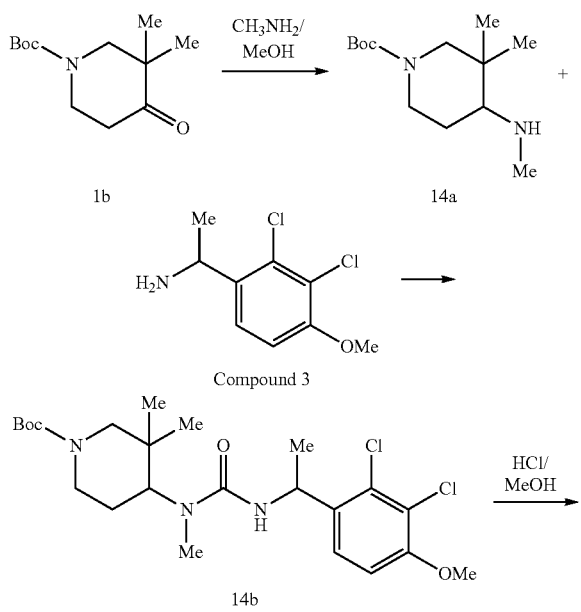

Compound 17

Step 1:
A mixture of 1b (2 g, 8.8 mmol) and methyl amine (30% in MeOH, 4 mL) was hydrogenated (50 psi, 60° C.) in the presence of 5% Pd/C (2000 mg) in MeOH (25 mL) overnight. After cooling the mixture was filtered and the filtrate was concentrated under reduced pressure. The residue was purified by column chromatography (silica, ethyl acetate/petroleum ether 1:10, v:v) to provide compound 14a (1.0 g, 48% yield) as a light yellow oil. ¹H-NMR (CDCl₃, 300 MHz): δ=4.07-4.09 (m, 1H), 2.65 (t, 2H), 2.51 (t, 2H), 2.43 (s, 3H), 2.38 (s, 2H), 1.41 (s, 9H), 1.14 (s, 6H). LC-MS: 243 [M+1]⁺.

Step 2:
To a solution of Compound 3 (382 mg, 1.74 mmol) in CH₂Cl₂ (50 mL) was added TEA (351 mg) and triphosgene (309 mg, 1.04 mmol). The mixture was stirred for 15 min at 0° C., then 14a (407 mg, 1.92 mmol) was added. The resulting mixture was stirred for 30 min at 0° C. and then concentrated under reduced pressure. The residue was purified by column chromatography (silica, MeOH/CH₂Cl₂ 1:20, v:v) to afford 14b (701 mg, 82% yield). LC-MS: 488 [M+1]⁺.

Step 3:
To a solution of 14b (701 mg, 1.44 mmol) in THF (20 mL) was added conc. HCl (2 mL). The mixture was heated at 75° C. for 2 h, then the solvent was evaporated to obtain crude 14c (580 mg), which was used in next step without further purification.

Step 4:
To the solution of crude 14c (580 mg) in MeOH (15 mL) was added aqueous formaldehyde (38%, 4 mL, 24 mmol,), sodium acetate (200 mg, 2.4 mmol) and acetic acid (2 mL, 26 mmol), followed by NaBH₃CN (135 mg, 2.9 mmol). The mixture was stirred at room temperature overnight, then concentrated under reduced pressure. The residue was purified by column chromatography (silica, MeOH/CH₂Cl₂ 1:20, v:v) to afford Compound 17 (262 mg, 38% yield) as a white solid. ¹H-NMR (CDCl₃, 300 MHz): δ=7.17-7.22 (m, 1H); 6.81-6.84 (m, 1H), 5.21-5.26 (m, 1H), 4.81-4.92 (m, 1H), 4.07-4.10 (m, 1H), 3.88-3.91 (m, 3H), 2.90-2.93 (m, 1H), 2.81-2.82 (m, 3H), 2.38-2.42 (m, 1H), 2.21-2.22 (m, 3H), 1.85-2.05 (m, 4H), 1.42-1.50 (m, 3H), 1.06-1.07 (m, 3H), 0.77-0.87 (m, 3H). LC-MS: 402 [M+1]⁺.

Synthesis of Compound 18

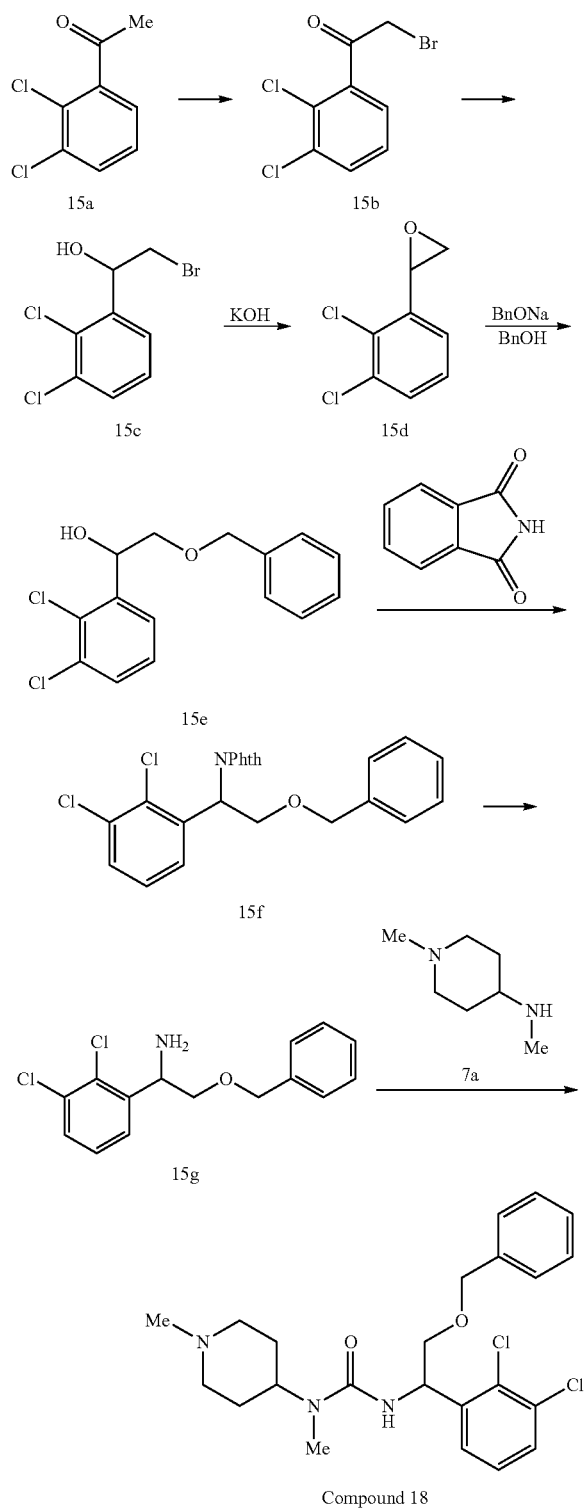

Compound 18

Step 1:

To a solution of 15a (5.04 g, 26.8 mmol) in CH$_2$Cl$_2$ (80 mL) at 0° C. was added dropwise a solution of Br$_2$ (3.81 g, 24.1 mmol) in CH$_2$Cl$_2$. The solution was stirred at room temperature overnight. The reaction mixture was washed with aqueous Na$_2$SO$_3$ solution, NaHCO$_3$ solution and water successively. The organic phase was dried with anhydrous Na$_2$SO$_4$ and concentrated under reduced pressure. The residue was purified by silica column chromatography (silica, ethyl acetate/petroleum ether 1:60, v:v) to provide compound 15b (7.1 g, quantitative yield).

Step 2:

To a solution of compound 15b (3 g, 11.2 mmol) in MeOH (90 mL) at −20° C. to −10° C. was added NaBH$_4$ (936 mg, 24.5 mmol). The reaction mixture was warmed up to room temperature and stirred for 1.5 h, then the solvent was evaporated and the residue was partitioned between ethyl acetate and water. The organic phase was separated, dried with anhydrous Na$_2$SO$_4$, and concentrated under reduced pressure. The residue was purified by column chromatography (silica, ethyl acetate/petroleum ether 1:30, v:v) to provide compound 15c (2.2 g, 73% yield). $^1$H-NMR (CDCl$_3$, 300 MHz): δ=7.54-7.57 (m, 1H), 7.42-7.46 (m, 1H), 7.24-7.29 (m, 1H), 5.29-5.34 (m, 1H), 3.81 (dd, 1H), 3.43 (dd, 1H), 2.84 (d, 1H).

Step 3:

To a solution of compound 15c (1.0 g, 3.72 mmol) in THF (100 mL) was added 1N KOH (5.6 mL, 5.58 mmol). The reaction was stirred at room temperature overnight. Ethyl acetate (100 mL) was added and the organic phase was washed with brine, dried with anhydrous Na$_2$SO$_4$ and concentrated under reduced pressure. The residue was purified by column chromatography (silica, petroleum ether) to provide compound 15d (432 mg, 62% yield). $^1$H-NMR (CDCl$_3$, 300 MHz): δ=7.38-7.42 (m, 1H), 7.16-7.23 (m, 2H), 4.19-5.21 (m, 1H), 3.20 (dd, 1H), 2.63 (dd, 1H).

Step 4:

Metallic sodium (11 mg, 0.53 mmol) was added to benzyl alcohol (2 mL) at room temperature under N$_2$ and the mixture was stirred until sodium was completely dissolved. Compound 15d (100 mg, 0.53 mmol) was then added to the solution, which was then stirred at 70° C. overnight. The reaction was concentrated under reduced pressure and the residue was purified by column chromatography (silica, ethyl acetate/petroleum ether 1:4, v:v) to provide compound 15e (44 mg, 28% yield). $^1$H-NMR (CDCl$_3$, 300 MHz): δ=7.53-7.56 (m, 1H), 7.30-7.35 (m, 6H), 7.24-7.26 (m, 1H), 5.35 (q, 1H), 4.61 (q, 2H), 3.78 (q, 1H), 3.38 (q, 1H), 3.00 (s, 1H).

Step 5:

To a solution of compound 15e (480 mg, 1.6 mmol), phthalimide (286 mg, 1.9 mmol) and PPh$_3$ (629 mg, 2.4 mmol) in dry THF (20 mL) at room temperature under N$_2$, was added DIAD (485 mg, 2.4 mmol). The mixture was stirred at room temperature overnight and then concentrated under reduced pressure. The residue was purified by column chromatography (silica, ethyl acetate/petroleum ether 1:30, v:v) to provide 15f (570 mg, 83% yield). $^1$H-NMR (CDCl$_3$, 300 MHz): δ=7.79-7.85 (m, 2H), 7.70-7.74 (m, 2H), 7.58 (dd, 1H), 7.40 (dd, 1H), 7.24-7.27 (m, 5H), 7.19 (t, 1H), 6.07 (dd, 1H), 4.59 (d, 2H), 4.46 (t, 1H), 4.00 (dd, 1H).

Step 6:

A solution of compound 15h (570 mg, 1.34 mmol) and hydrazine hydrate (98%) (270 mg, 5.36 mmol) in MeOH (10 mL) was heated under reflux for 2 h. The mixture was then concentrated under reduced pressure, the residue was dissolved in CH$_2$Cl$_2$ and washed with water. The aqueous phase was back extracted with CH$_2$Cl$_2$ (3×30 mL) and the combined organic phases were dried with anhydrous Na$_2$SO$_4$ and concentrated to give 15g (350 mg, 88% yield). LC-MS: 296 [M+1]$^+$.

Step 7:

To a solution of 15g (350 mg, 1.19 mmol) in dry CH$_2$Cl$_2$ (10 mL) at room temperature under nitrogen was added triphosgene (353 mg, 1.19 mmol). The reaction was stirred at room temperature for 10 min, followed by the addition of 7a (235 mg, 1.43 mmol). The reaction mixture was stirred at room temperature for 1 h, then concentrated under reduced pressure. The residue was purified by column chromatography (silica, MeOH/CH$_2$Cl$_2$ 1:20, v:v) to provide compound Compound 18 (450 mg, 84% yield) as a white solid. $^1$H-NMR (CDCl$_3$, 300 MHz): δ=7.28-7.36 (m, 8H), 5.43-5.48 (m, 2H), 4.50 (q, 2H), 4.26-4.30 (m, 1H), 3.79 (q, 1H), 3.62 (q, 1H), 3.10 (t, 2H), 2.81 (s, 3H), 2.43 (s, 3H), 2.30-2.36 (m, 2H), 2.10-2.17 (m, 2H), 1.65-1.70 (m, 2H). LC-MS: 450 [M+1]$^1$.

Synthesis of Compound 19

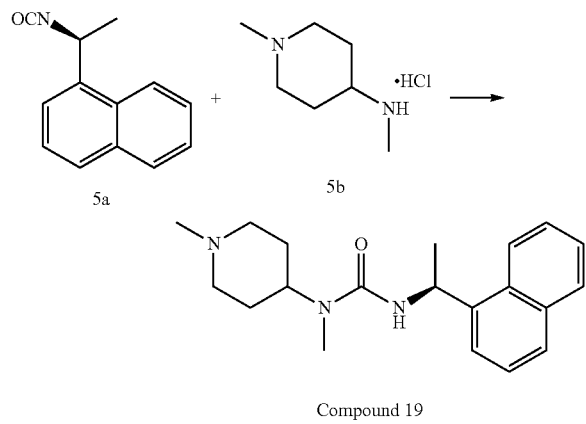

A solution of 5a (115 mg, 0.584 mmol), 5b (98 mg, 0.596 mmol) and TEA (0.5 mL) in dry DCM (20 mL) was stirred at room temperature under N$_2$ for 30 min. After the reaction was complete, water (10 mL) was added. The organic phase was separated, dried with Na$_2$SO$_4$ and concentrated. The residue was purified by column chromatography (silica, MeOH: DCM=1:20) to afford Compound 19 (108 mg, 57% yield). $^1$H NMR (300 MHz, DMSO-d$_6$): δ=8.14 (d, 1H), 7.92 (t, 1H), 7.78 (d, 1H), 7.57-7.45 (m, 4H), 6.71 (d, 1H), 5.71-5.60 (m, 1H), 4.16-4.08 (m, 1H), 3.17 (br, 2H); 2.72-2.61 (m, 5H), 2.50 (s, 3H), 1.93-1.87 (m, 2H), 1.58-1.51 (m, 5H). LC-MS: 326 [M+1]$^+$ Synthesis of Compound 20

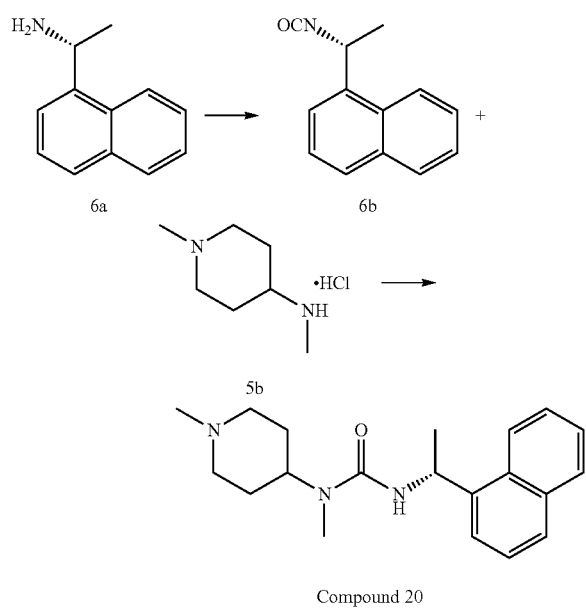

To a solution of 6a (100 mg, 0.584 mmol), TEA (1.5 mL) in dry DCM (20 mL) was added triphosgene (104 mg, 0.350 mmol) at room temperature under N$_2$. The mixture was stirred at room temperature for 30 min, then 5b (98 mg, 0.596 mmol) was added. The resulted mixture was stirred at room temperature for 30 min. Water (10 mL) was added and the organic phase was separated, dried with Na$_2$SO$_4$ and concentrated. The residue was purified by column chromatography (silica, MeOH:DCM=1:20) to provide Compound 20 (109 mg, 57% yield). $^1$H NMR (300 MHz, DMSO-d$_6$): δ=8.13 (d, 1H), 7.95 (t, 1H), 7.78 (d, 1H), 7.56-7.45 (m, 4H), 6.70-6.68 (d, 1H), 5.70-5.61 (m, 1H), 4.02-3.94 (m, 1H), 2.93 (br, 2H), 2.70 (s, 3H), 2.27 (s, 3H), 2.16 (br, 2H), 1.76-1.63 (m, 2H), 1.50-1.35 (m, 5H). LC-MS: 326 [M+1]$^+$.

2. Materials and Methods i. Calcium FLIPR Assay

The intracellular calcium assay was carried out in a 384-well format FLIPR™ (Molecular Device) HEK293/GHSR1a cell line. Cells were seeded 24 hr prior to the experiments at an optimal density per well. Preincubation with selected calcium dye lasted for 30-60 min at room temperature or 37° C. Test compounds, dissolved in DMSO, were added at the appropriate time and incubated for 15 min followed by the addition of ghrelin with FlexStation or FLIPR. Relative fluorescence was monitored by the FLIPR™ Molecular Device. EC$_{50}$ and IC$_{50}$ values were estimated from dose-response data using GraphPad Prism software. To check for GHSR-1a agonism the compound was added at t=20 sec. and the calcium response was followed for 2 minutes. To check for GHSR-1a antagonism the compound and Ghrelin (10 nM) were added to the cells at t=20 sec. and the calcium response was measured for 2 minutes. The potency of the antagonist was calculated by its ability to reduce the ghrelin response. Dose-response curves were made for relevant antagonists.

ii. Evaluation of GHSR1a Antagonists on Food Intake Test in Mouse

Male C57BL/6J mice, 18-22 g body weight, were fasted overnight (16 h before compound administration) and placed in a regular light dark cycle (6:00-18:00 light/18:00-6:00 dark). After 1 wk acclimation, animals were sorted into two groups (n=6 each, 2 per cage) based on body weight. Animals in group one were be treated with vehicle and animals in group 2 were treated with the test agent (n=6 for each group). The cumulative food intake was evaluated at 1, 2, 4, 8 and 24 hrs after drug or vehicle treatment. Food intake was measured by subtracting uneaten food from the initial premeasured food.

3. Results

The following table presents representative compounds of formula (I) with biological data including the ghrelin antagonist/agonist activity in vitro and mouse food intake results. The data clearly demonstrates that compounds of formula (I) are ghrelin receptor modulators and are useful in preventing and/or treating diseases associated with ghrelin receptor, for example, obesity.

TABLE 1

| Structure | IC₅₀ FLIPR antagonist Activity (μM) | EC₅₀ FLIPR against Activity (μM/Emax) | Mouse Food Intake (% inhibition. Doses as mg/kg i.p. |
|---|---|---|---|
| (1-methyl-3,3-dimethylpiperidin-4-yl)-N-methyl-N'-[(1-naphthalen-1-yl)ethyl]urea | 0.021 | 0.009/1081 | 47% inhib. at 4 h, activity up to 8 hrs (30 mg/kg) |
| (1-methyl-3,3-dimethylpiperidin-4-yl)-N-benzyl-N'-[(1-naphthalen-1-yl)ethyl]urea | 0.005 | 0.006/1268 | NSE (30 mg/kg) |
| (1-methylpiperidin-4-yl)-N-ethyl-N'-[(1-naphthalen-1-yl)ethyl]urea | 0.320 | 30/124 | 28% inhibition at 1 hr, activity up to 24 hrs (30 mg/kg) |
| (1-methylpiperidin-4-yl)-N-methyl-N'-[(1-(2,3-dichlorophenyl))ethyl]urea | 0.120 | 0.009/138 | NSE (10 mg/kg) |
| (1-methylpiperidin-4-yl)-N-methyl-N'-[(1-(4-methoxynaphthalen-1-yl))ethyl]urea | 0.040 | 0.030/2316 | NSE (10 mg/kg), 70% increase food intake at 1 hr, activity up to 24 hrs (30 mg/kg). |
| (1-methylpiperidin-4-yl)-N-methyl-N'-[(2-hydroxy-1-naphthalen-1-yl)ethyl]urea | 0.910 | 0.49/689 | 27% inhibition at to 24 hrs (10 mg/kg) |
| (1-methylpiperidin-4-yl)-N-benzyl-N'-[(1-(2,3-dichlorophenyl))ethyl]urea | 0.022 | 16.76/497 | 47% inhibition at 1 hr (10 mg/kg) |

TABLE 1-continued

| Structure | IC$_{50}$ FLIPR antagonist Activity (μM) | EC$_{50}$ FLIPR against Activity (μM/Emax) | Mouse Food Intake (% inhibition. Doses as mg/kg i.p. |
|---|---|---|---|
| 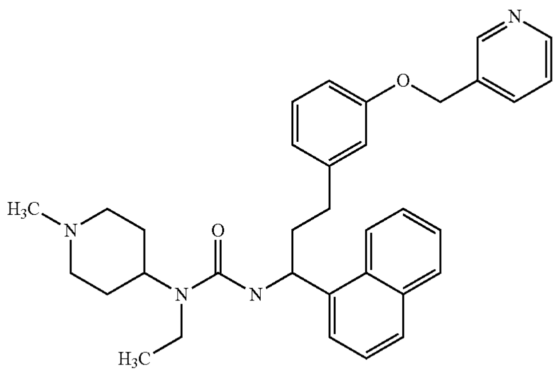 [SMILES: CCN(C(=O)NC(CCc1cccc(OCc2cccnc2)c1)c1cccc2ccccc12)C1CCN(C)CC1] | 0.075 | 18.70/118.5 | 74% inhibition at 1 hr, activity up to 24 hrs (10 mg/kg) |
| 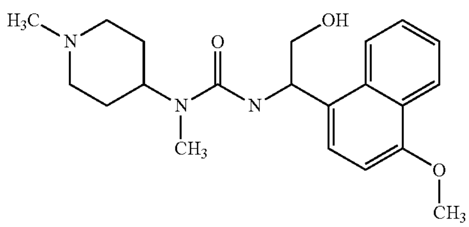 | 0.066 | 0.020/3945 | 47% inhibition at 1 hr (10 mg/kg) |
| 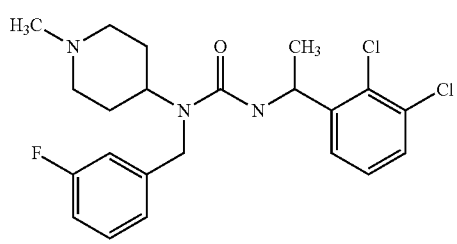 [SMILES: CC(NC(=O)N(Cc1cccc(F)c1)C1CCN(C)CC1)c1cccc(Cl)c1Cl] | 0.065 | 30/NA | 44% inhibition at 1 hr (10 mg/kg) |
| 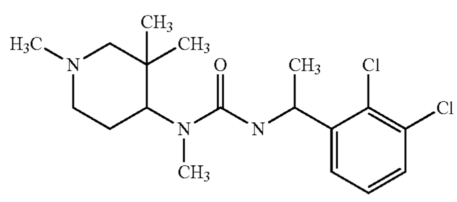 [SMILES: CC(NC(=O)N(C)C1CCN(C)CC1(C)C)c1cccc(Cl)c1Cl] | 0.012 | 30/260 | 26% inhibition at 1 hr (10 mg/kg) |
| 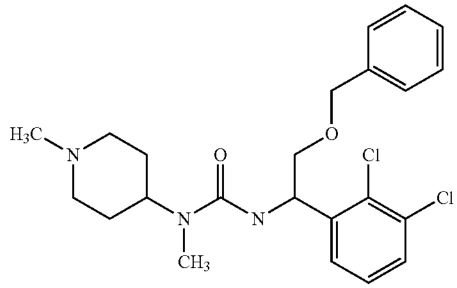 [SMILES: CN1CCC(N(C)C(=O)NC(COCc2ccccc2)c2cccc(Cl)c2Cl)CC1] | 0.070 | 30/1573 | NSE (3 mg/kg), 40% inhibition at 1 hr, activity up to 4 hrs (10 mg/kg), 50% inhibition at 1 hrs, activity up to 2 hrs (30 mg/kg) |

TABLE 1-continued

| Structure | IC$_{50}$ FLIPR antagonist Activity (μM) | EC$_{50}$ FLIPR against Activity (μM/Emax) | Mouse Food Intake (% inhibition. Doses as mg/kg i.p. |
|---|---|---|---|
| (structure) | 0.038 | 30/NA | 39% inhibition at 1 hr, no activity up to follow hrs. (3 mg/kg), 95% inhibition at 1 hr, activity up to 24 hrs (10 mg/kg), 70% inhibition at 2 hr, activity up to 24 hrs (30 mg/kg) |
| (structure) | 0.005 | 30/NA | NSE (10 mg/kg) |
| (structure) | 0.012 | 0.010/3208 | NSE (10 mg/kg) |
| (structure) | 0.003 | 0.010/2921 | NSE (10 mg/kg) |
| (structure) | 0.007 | 30/NA | NSE (10 mg/kg) |
| (structure) | 0.005 | 30/NA | NSE (10 mpk) |

TABLE 1-continued

| Structure | IC$_{50}$ FLIPR antagonist Activity (μM) | EC$_{50}$ FLIPR against Activity (μM/Emax) | Mouse Food Intake (% inhibition. Doses as mg/kg i.p.) |
|---|---|---|---|
| 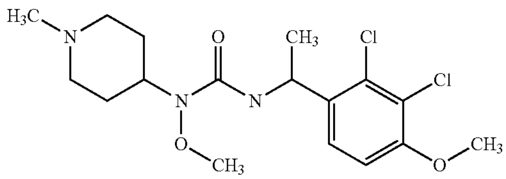 | 0.004 | 0.0082/4239 | N/A |
| 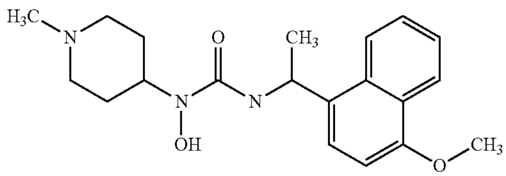 | n/a | 0.0021/4203 | N/A |

* NSE: not significant effect.

We claim:

1. A compound of formula (I), or a pharmaceutically acceptable salt thereof,

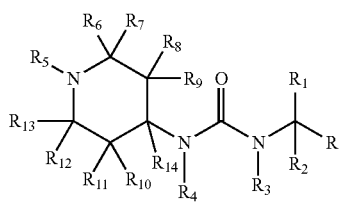

Formula (I)

wherein:
R is selected from the group consisting of aryl, arylalkyl, optionally substituted with one or more independent R$^{103}$ substituents;
R$_1$ is selected from the group consisting of hydroxy, amino, alkyl, alkenyl, cycloalkyl, halogen, alkoxy, alkoxyalkyl, aryl, arylalkyl, heterocycloalkyl, heterocycloalkylalkyl, heteroaryl and heteroarylalkyl, each optionally independently substituted with one or more independent R$^{103}$ substituents;
R$_2$ is hydrogen;
R$_3$ is selected from the group consisting of hydrogen, alkyl, alkenyl, cycloalkyl, aryl, arylalkyl, heterocycloalkyl, heterocycloalkylalkyl, heteroaryl, heteroarylalkyl, —C(O)R$^{101}$, —C(O)OR$^{101}$, —C(O)NR$^{101}$R$^{102}$, —S(O)$_2$R$^{102}$, —SR$^{101}$ and —S(O)$_2$NR$^{101}$R$^{102}$, optionally substituted with one or more independent R$^{103}$ substituents;
R$_4$ is selected from the group consisting of alkyl, alkenyl, cycloalkyl, aryl, arylalkyl, heterocycloalkyl, heterocycloalkylalkyl, heteroaryl, heteroarylalkyl, —OR$^{103}$, NR$^{101}$R$^{102}$, —C(O)R$^{101}$, —C(O)R$^{101}$, —C(O)NR$^{101}$R$^{102}$, -alkylNR$^{101}$R$^{102}$, —S(O)$_2$R$^{102}$, —S(O)$_2$R$^{102}$, —SR$^{101}$, and —S(O)$_2$NR$^{101}$R$^{102}$, optionally substituted with one or more independent R$^{103}$ substituents;
R$_5$ is selected from the group consisting of alkyl, alkenyl, cycloalkyl, aryl, heterocycloalkyl, heteroaryl, heteroarylalkyl, oxide (=O), —C(O)R$^{101}$, —C(O)OR$^{101}$, —C(O)NR$^{101}$R$^{102}$, —S(O)$_2$R$^{102}$, —SR$^{101}$ and —S(O)$_2$NR$^{101}$R$^{102}$;
R$_6$, R$_7$, R$_8$, R$_9$, R$_{10}$, R$_{11}$, R$_{12}$, R$_{13}$ and R$_{14}$ are each independently selected from the group consisting of hydrogen, cyano, —NO$_2$, —OR$^{101}$, hydroxy, amino, alkyl, alkenyl, cycloalkyl, halogen, alkoxy, alkoxyalkyl, aryl, arylalkyl, heterocycloalkyl, heterocycloalkylalkyl, heteroaryl, heteroarylalkyl, —C(O)R$^{101}$, —C(O)OR$^{101}$, —C(O)NR$^{101}$R$^{102}$, —NR$^{101}$R$^{102}$, —NR$^{101}$S(O)$_2$R$^{102}$, —NR$^{101}$C(O)R$^{102}$, —S(O)$_2$R$^{102}$, —SR$^{101}$ and —S(O)$_2$NR$^{101}$R$^{102}$, each optionally independently substituted with one or more independent R$^{103}$ substituents; and R$^{101}$, R$^{102}$, and R$^{103}$ are each independently selected from the group consisting of hydrogen, cyano, —NO$_2$, —OR$^{104}$, hydroxy, amino, alkyl, alkenyl, cycloalkyl, halogen, alkoxy, alkoxyalkyl, aryl, arylalkyl, heterocycloalkyl, heterocycloalkylalkyl, heteroaryl, heteroarylalkyl, —C(O)R$^{104}$, —C(O)OR$^{104}$, —C(O)NR$^{104}$R$^{105}$, —NR$^{104}$R$^{105}$, —NR$^{104}$S(O)$_2$R$^{105}$, —NR$^{104}$C(O)R$^{105}$, —S(O)$_2$R$^{104}$, —SR$^{104}$ and —S(O)$_2$NR$^{104}$R$^{105}$, each optionally independently substituted with one or more independent R$^{103}$ substituents; or R$^{101}$, R$^{102}$, together with the atoms connecting the same, form a fused or non-fused mono, bicyclic or tricyclic heterocyclic or carbocyclic ring which is optionally independently substituted with one or more R$^{103}$ substituents; and
R$^{104}$ and R$^{105}$ are each independently selected from the group consisting of hydrogen, cyano, —NO$_2$, hydroxy, hydroxyalkyl, amino, alkyl, alkenyl, cycloalkyl, halogen, alkoxy, alkoxyalkyl, aryl, arylalkyl, heterocycloalkyl, heterocycloalkylalkyl, heteroaryl and heteroarylalkyl.

2. The compound of claim 1, or a pharmaceutically acceptable salt thereof, wherein R is aryl.

3. The compound of claim 1, or a pharmaceutically acceptable salt thereof, wherein R is phenyl or naphthalene which is optionally independently substituted with from one to six substituents independently selected from the group consisting of hydrogen, chloro, fluoro, bromo, trifluoromethyl, cyano, methoxy, ethoxy, methyl and ethyl.

4. The compound of claim 1, or a pharmaceutically acceptable salt thereof, wherein R$_1$ is selected from the group consisting of alkoxy, alkoxyalkyl, —OR$^{101}$, hydroxy, hydroxyalkyl, amino, alkyl, alkenyl, cycloalkyl, aryl, arylalkyl, heterocycloalkyl, heterocycloalkylalkyl, heteroaryl and heteroarylalkyl.

5. The compound of claim 1, or a pharmaceutically acceptable salt thereof, wherein $R_1$ is selected from the group consisting of alkyl, cycloalkyl, hydroxyalkyl, alkoxyalkyl, arylalkyl and heteroarylalkyl.

6. The compound of claim 1, or a pharmaceutically acceptable salt thereof, wherein $R_1$ is selected from the group consisting of methyl, —$CH_2OH$, and —$CH_2$—O—$CH_2$-phenyl.

7. The compound of claim 1, or a pharmaceutically acceptable salt thereof, wherein $R_3$ is hydrogen, alkyl or cycloalkyl.

8. The compound of claim 1, or a pharmaceutically acceptable salt thereof, wherein $R_4$ is selected from the group consisting of alkyl, cycloalkyl, hydroxy, amino, alkoxy, alkylamino, aryl, arylalkyl, heterocycloalkyl, heterocycloalkylalkyl, heteroaryl, heteroarylalkyl and aminoalkyl.

9. The compound of claim 1, or a pharmaceutically acceptable salt thereof, wherein $R_4$ is methyl, ethyl, benzyl, or benzyl substituted with from one to five substituents independently selected from the group consisting of methyl, fluoro, chloro, trifluoromethyl, methoxy, cyano and hydroxy.

10. The compound of claim 1, or a pharmaceutically acceptable salt thereof, wherein $R_5$ is selected from the group consisting of alkyl, cycloalkyl, oxide (=O), aryl, heterocycloalkyl, heterocycloalkylalkyl, heteroaryl, heteroarylalkyl, —$C(O)R^{101}$, —$C(O)OR^{101}$ and —$C(O)NR^{101}R^{102}$.

11. The compound of claim 1, or a pharmaceutically acceptable salt thereof, wherein $R_5$ is methyl.

12. The compound of claim 1, or a pharmaceutically acceptable salt thereof, wherein $R_6$, $R_7$, $R_8$, $R_9$, $R_{10}$, $R_{11}$, $R_{12}$, $R_{13}$ and $R_{14}$ are each independently selected from the group consisting of hydrogen, alkyl, cycloalkyl, —$C(O)OR^{101}$, and -alkyl$OR^{103}$.

13. The compound of claim 1, or a pharmaceutically acceptable salt thereof, wherein $R_8$ and $R_9$ are each independently hydrogen, alkyl, cycloalkyl, —$C(O)OR^{101}$, or -alkyl$OR^{103}$.

14. The compound of claim 1, or a pharmaceutically acceptable salt thereof, wherein $R_8$ and $R_9$ are each independently hydrogen, methyl, ethyl, —C(=O)OEt, or —$CH_2OH$.

15. A compound selected from the group consisting of one of the following compounds, or a pharmaceutically acceptable salt thereof:

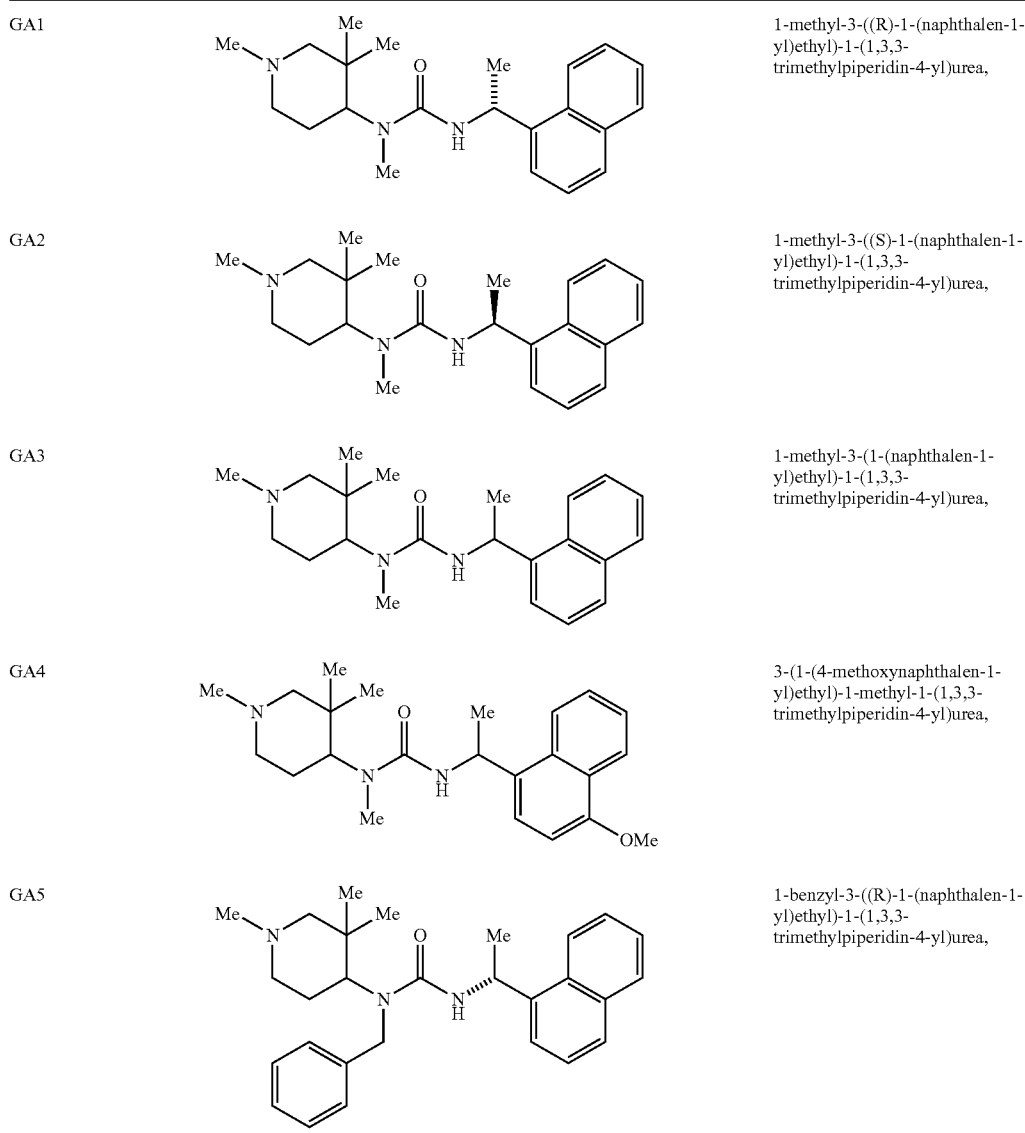

| | | |
|---|---|---|
| GA6 | 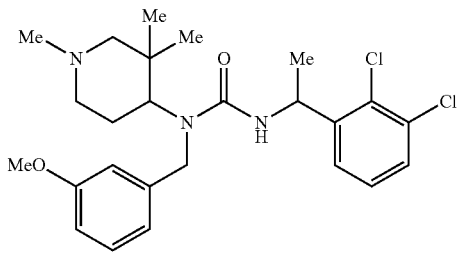 | 3-(1-(2,3-dichlorophenyl)ethyl)-1-(3-methoxybenzyl)-1-(1,3,3-trimethylpiperidin-4-yl)urea, |
| GA7 | 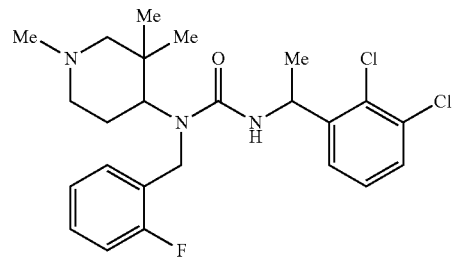 [SMILES: CC(NC(=O)N(Cc1ccccc1F)C1CCN(C)CC1(C)C)c1cccc(Cl)c1Cl] | 3-(1-(2,3-dichlorophenyl)ethyl)-1-(2-fluorobenzyl)-1-(1,3,3-trimethylpiperidin-4-yl)urea, |
| GA8 | 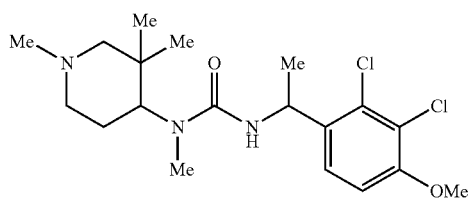 | 3-(1-(2,3-dichloro-4-methoxyphenyl)ethyl)-1-methyl-1-(1,3,3-trimethylpiperidin-4-yl)urea, |
| GA9 | 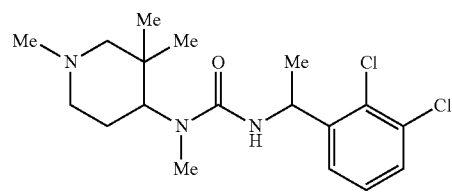 | 3-(1-(2,3-dichlorophenyl)ethyl)-1-methyl-1-(1,3,3-trimethylpiperidin-4-yl)urea, |
| GA10 | 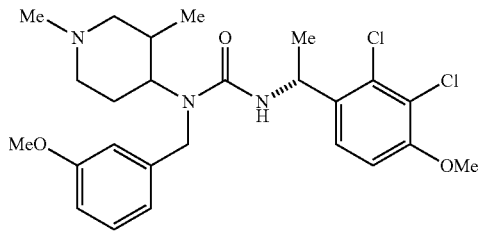 | 3-((R)-1-(2,3-dichloro-4-methoxyphenyl)ethyl)-1-(1,3-dimethylpiperidin-4-yl)-1-(3-methoxybenzyl)urea, |
| GA11 | 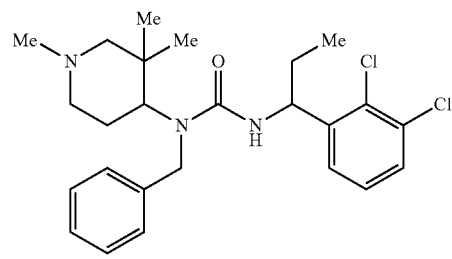 [SMILES: CCC(NC(=O)N(Cc1ccccc1)C1CCN(C)CC1(C)C)c1cccc(Cl)c1Cl] | 1-benzyl-3-(1-(2,3-dichlorophenyl)propyl)-1-(1,3,3-trimethylpiperidin-4-yl)urea, |
| GA12 | 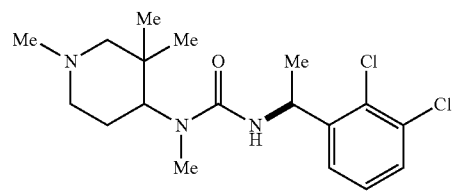 | 3-((S)-1-(2,3-dichlorophenyl)ethyl)-1-methyl-1-(1,3,3-trimethylpiperidin-4-yl)urea, |

-continued

| | | |
|---|---|---|
| GA13 | 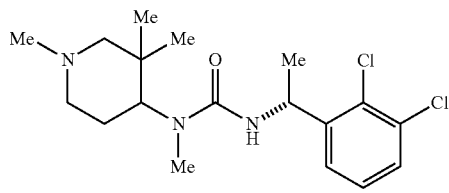 | 3-((R)-1-(2,3-dichlorophenyl)ethyl)-1-methyl-1-(1,3,3-trimethylpiperidin-4-yl)urea, |
| GA14 | 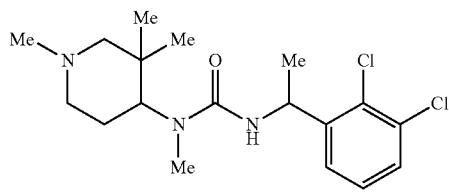 [SMILES: CC(NC(=O)N(C)C1CCN(C)CC1(C)C)c1cccc(Cl)c1Cl] | 3-(1-(2,3-dichlorophenyl)ethyl)-1-methyl-1-(1,3,3-trimethylpiperidin-4-yl)urea, |
| GA15 | 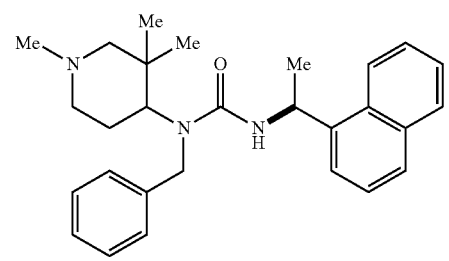 | 1-benzyl-3-((S)-1-(naphthalen-1-yl)ethyl)-1-(1,3,3-trimethylpiperidin-4-yl)urea, |
| GA16 | 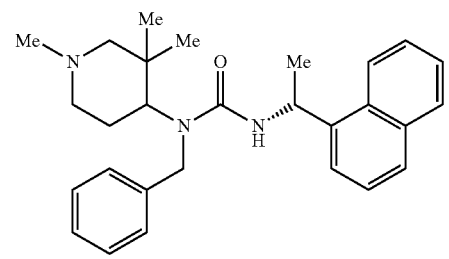 | 1-benzyl-3-((R)-1-(naphthalen-1-yl)ethyl)-1-(1,3,3-trimethylpiperidin-4-yl)urea, |
| GA17 | 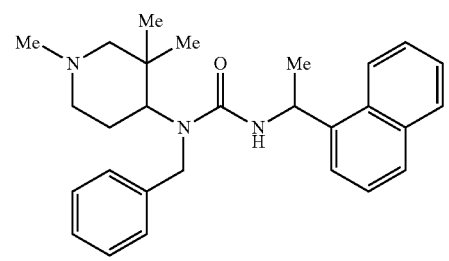 | 1-benzyl-3-(1-(naphthalen-1-yl)ethyl)-1-(1,3,3-trimethylpiperidin-4-yl)urea, |
| GA18 | 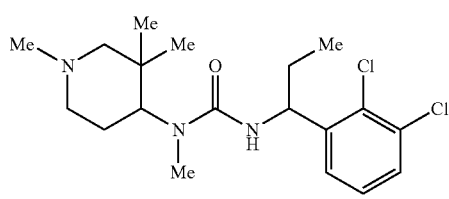 | 3-(1-(2,3-dichlorophenyl)propyl)-1-methyl-1-(1,3,3-trimethylpiperidin-4-yl)urea, |
| GA19 | 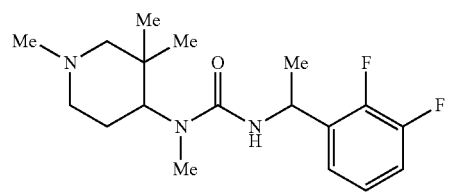 [SMILES: CC(NC(=O)N(C)C1CCN(C)CC1(C)C)c1cccc(F)c1F] | 3-(1-(2,3-difluorophenyl)ethyl)-1-methyl-1-(1,3,3-trimethylpiperidin-4-yl)urea, |

-continued

| | | |
|---|---|---|
| GA20 | 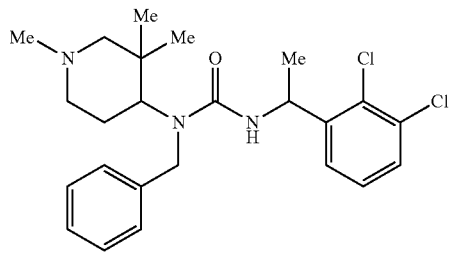 [SMILES: CC(NC(=O)N(Cc1ccccc1)C1CCN(C)CC1(C)C)c1cccc(Cl)c1Cl] | 1-benzyl-3-(1-(2,3-dichlorophenyl)ethyl)-1-(1,3,3-trimethylpiperidin-4-yl)urea, |
| GA21 | 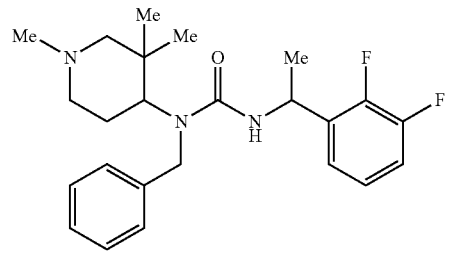 [SMILES: CC(NC(=O)N(Cc1ccccc1)C1CCN(C)CC1(C)C)c1cccc(F)c1F] | 1-benzyl-3-(1-(2,3-difluorophenyl)ethyl)-1-(1,3,3-trimethylpiperidin-4-yl)urea, |
| GA22 | 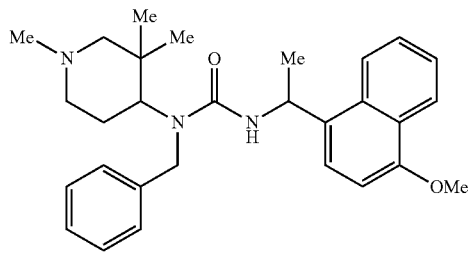 | 1-benzyl-3-(1-(4-methoxynaphthalen-1-yl)ethyl)-1-(1,3,3-trimethylpiperidin-4-yl)urea, |
| GA23 | 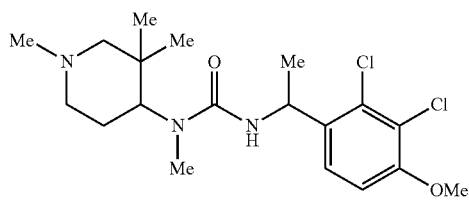 | 3-(1-(2,3-dichloro-4-methoxyphenyl)ethyl)-1-methyl-1-(1,3,3-trimethylpiperidin-4-yl)urea, |
| GA24 | 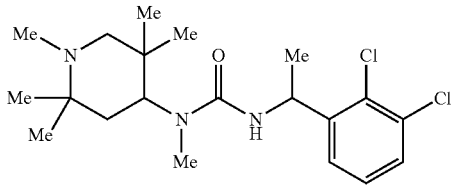 | 3-(1-(2,3-dichlorophenyl)ethyl)-1-methyl-1-(1,2,2,5,5-pentamethylpiperidin-4-yl)urea, |
| GA25 | 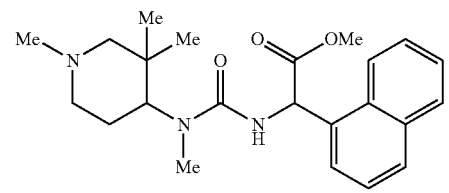 [SMILES: COC(=O)C(NC(=O)N(C)C1CCN(C)CC1(C)C)c1cccc2ccccc12] | methyl 2-(3-methyl-3-(1,3,3-trimethylpiperidin-4-yl)ureido)-2-(naphthalen-1-yl)acetate, |
| GA26 | 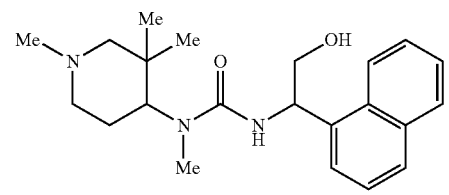 [SMILES: CN1CCC(N(C)C(=O)NC(CO)c2cccc3ccccc23)C(C)(C)C1] | 3-(2-hydroxy-1-(naphthalen-1-yl)ethyl)-1-methyl-1-(1,3,3-trimethylpiperidin-4-yl)urea, |

| | | |
|---|---|---|
| GA27 | 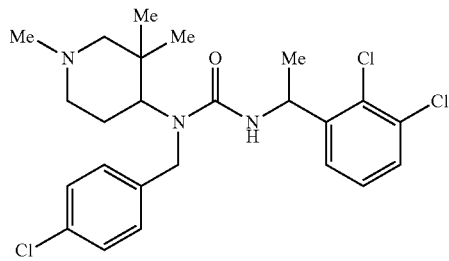 [SMILES: CC(NC(=O)N(Cc1ccc(Cl)cc1)C1CCN(C)CC1(C)C)c1cccc(Cl)c1Cl] | 1-(4-chlorobenzyl)-3-(1-(2,3-dichlorophenyl)ethyl)-1-(1,3,3-trimethylpiperidin-4-yl)urea, |
| GA28 | 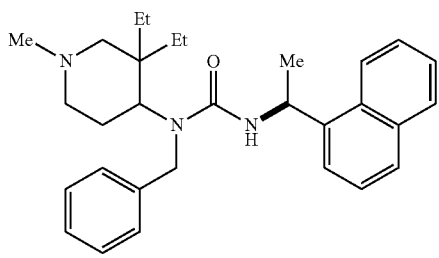 | 1-benzyl-1-(3,3-diethyl-1-methylpiperidin-4-yl)-3-((S)-1-(naphthalen-1-yl)ethyl)urea, |
| GA29 | 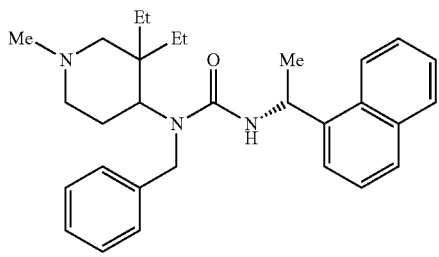 | 1-benzyl-1-(3,3-diethyl-1-methylpiperidin-4-yl)-3-((R)-1-(naphthalen-1-yl)ethyl)urea, |
| GA30 | 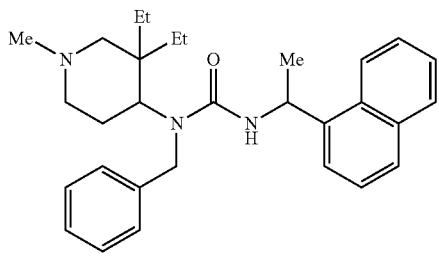 | 1-benzyl-1-(3,3-diethyl-1-methylpiperidin-4-yl)-3-(1-(naphthalen-1-yl)ethyl)urea, |
| GA31 | 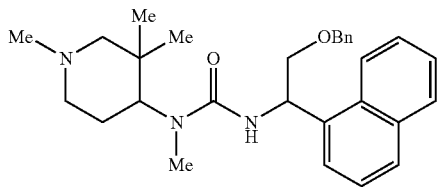 [SMILES: CN1CCC(N(C)C(=O)NC(COCc2ccccc2)c2cccc3ccccc23)C(C)(C)C1] | 3-(2-(benzyloxy)-1-(naphthalen-1-yl)ethyl)-1-methyl-1-(1,3,3-trimethylpiperidin-4-yl)urea, |
| GA32 | 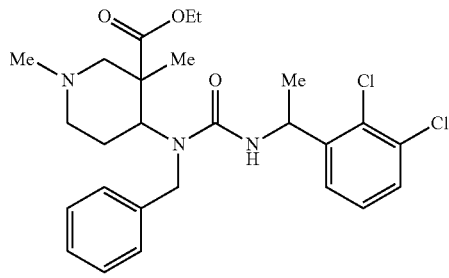 | ethyl 4-(1-benzyl-3-(1-(2,3-dichlorophenyl)ethyl)ureido)-1,3-dimethylpiperidine-3-carboxylate, |

-continued

GA33 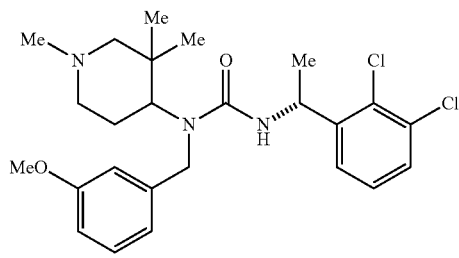 3-((R)-1-(2,3-dichlorophenyl)ethyl)-1-(3-methoxybenzyl)-1-(1,3,3-trimethylpiperidin-4-yl)urea, GA34 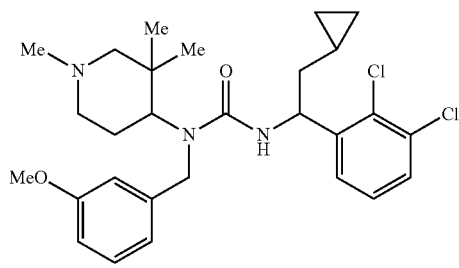 [SMILES: COc1cccc(CN(C(=O)NC(CC2CC2)c2cccc(Cl)c2Cl)C2CCN(C)CC2(C)C)c1] 3-(2-cyclopropyl-1-(2,3-dichlorophenyl)ethyl)-1-(3-methoxybenzyl)-1-(1,3,3-trimethylpiperidin-4-yl)urea, GA35 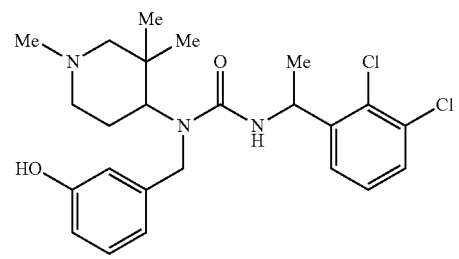 [SMILES: CC(NC(=O)N(Cc1cccc(O)c1)C1CCN(C)CC1(C)C)c1cccc(Cl)c1Cl] 3-(1-(2,3-dichlorophenyl)ethyl)-1-(3-hydroxybenzyl)-1-(1,3,3-trimethylpiperidin-4-yl)urea, GA36 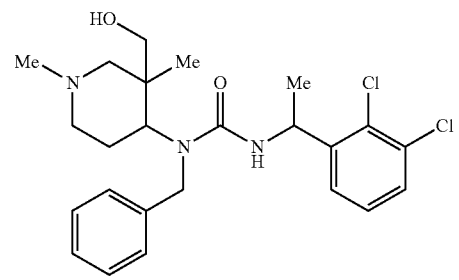 [SMILES: CC(NC(=O)N(Cc1ccccc1)C1CCN(C)CC1(C)CO)c1cccc(Cl)c1Cl] 1-benzyl-3-(1-(2,3-dichlorophenyl)ethyl)-1-(3-(hydroxymethyl)-1,3-dimethylpiperidin-4-yl)urea, GA37 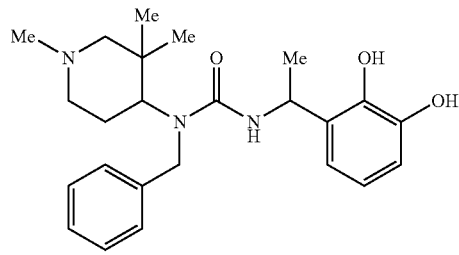 1-benzyl-3-(1-(2,3-dihydroxyphenyl)ethyl)-1-(1,3,3-trimethylpiperidin-4-yl)urea, GA38 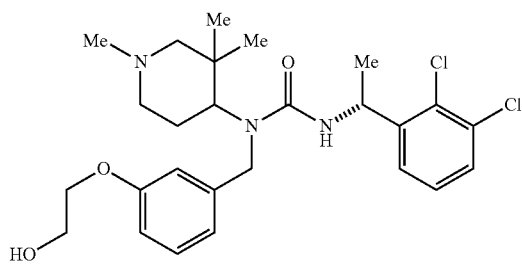 3-((R)-1-(2,3-dichlorophenyl)ethyl)-1-(3-(2-hydroxyethoxy)benzyl)-1-(1,3,3-trimethylpiperidin-4-yl)urea,

| | | |
|---|---|---|
| GA39 | 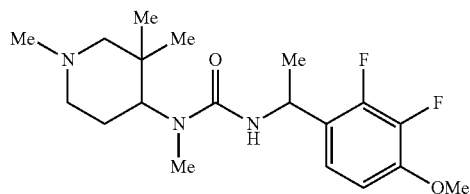 [SMILES: COc1ccc(C(C)NC(=O)N(C)C2CCN(C)CC2(C)C)c(F)c1F] | 3-(1-(2,3-difluoro-4-methoxyphenyl)ethyl)-1-methyl-1-(1,3,3-trimethylpiperidin-4-yl)urea, |
| GA40 | 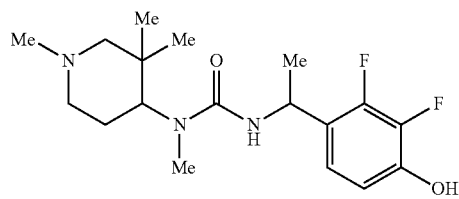 [SMILES: CC(NC(=O)N(C)C1CCN(C)CC1(C)C)c1ccc(O)c(F)c1F] | 3-(1-(2,3-difluoro-4-hydroxyphenyl)ethyl)-1-methyl-1-(1,3,3-trimethylpiperidin-4-yl)urea, |
| GA41 | 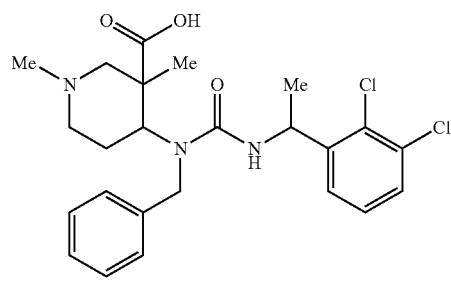 | 4-(1-benzyl-3-(1-(2,3-dichlorophenyl)ethyl)ureido)-1,3-dimethylpiperidine-3-carboxylic acid, |
| GA42 | 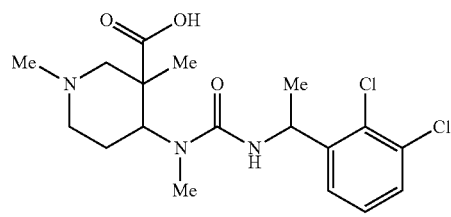 | ethyl 4-(3-(1-(2,3-dichlorophenyl)ethyl)-1-methylureido)-1,3-dimethylpiperidine-3-carboxylate, |
| GA43 | 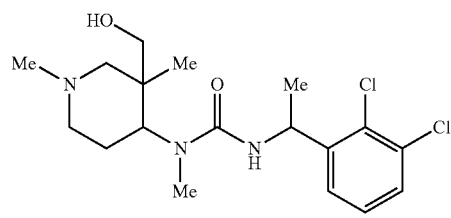 [SMILES: CC(NC(=O)N(C)C1CCN(C)CC1(C)CO)c1cccc(Cl)c1Cl] | 3-(1-(2,3-dichlorophenyl)ethyl)-1-(3-(hydroxymethyl)-1,3-dimethylpiperidin-4-yl)-1-methylurea, |
| GA44 | 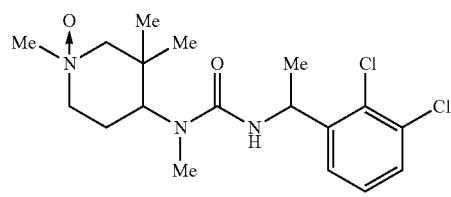 [SMILES: CC(NC(=O)N(C)C1CC[N+](C)([O-])CC1(C)C)c1cccc(Cl)c1Cl] | 4-(3-(1-(2,3-dichlorophenyl)ethyl)-1-methylureido)-1,3,3-trimethylpiperidine 1-oxide, |
| GA45 | 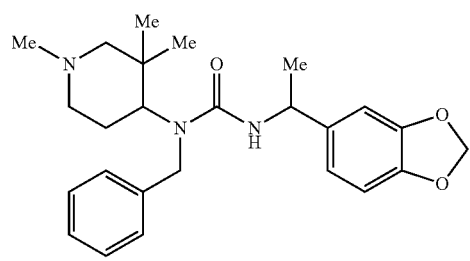 [SMILES: CC(NC(=O)N(Cc1ccccc1)C1CCN(C)CC1(C)C)c1ccc2c(c1)OCO2] | 3-(1-(benzo[d][1,3]dioxol-5-yl)ethyl)-1-benzyl-1-(1,3,3-trimethylpiperidin-4-yl)urea, |

-continued

| | | |
|---|---|---|
| GA46 | 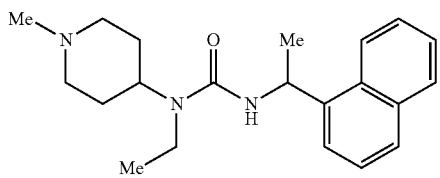 | 1-ethyl-1-(1-methylpiperidin-4-yl)-3-(1-(naphthalen-1-yl)ethyl)urea, |
| GA47 | 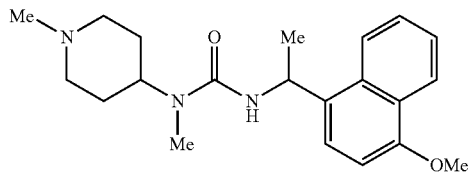 | 3-(1-(4-methoxynaphthalen-1-yl)ethyl)-1-methyl-1-(1-methylpiperidin-4-yl)urea, |
| GA48 | 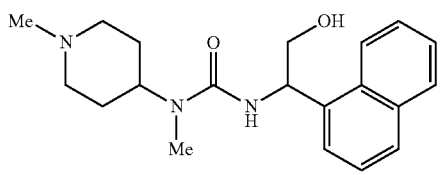 | 3-(2-hydroxy-1-(naphthalen-1-yl)ethyl)-1-methyl-1-(1-methylpiperidin-4-yl)urea, |
| GA49 | 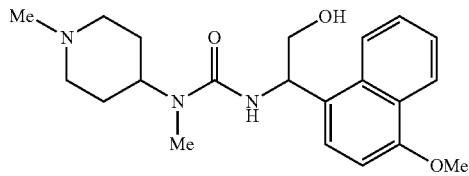 [SMILES: COc1ccc(C(CO)NC(=O)N(C)C2CCN(C)CC2)c2ccccc12] | 3-(2-hydroxy-1-(4-methoxynaphthalen-1-yl)ethyl)-1-methyl-1-(1-methylpiperidin-4-yl)urea, |
| GA50 | 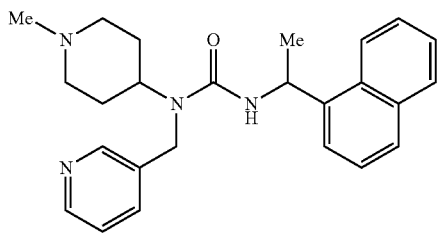 | 1-(1-methylpiperidin-4-yl)-3-(1-(naphthalen-1-yl)ethyl)-1-(pyridin-3-ylmethyl)urea, |
| GA51 | 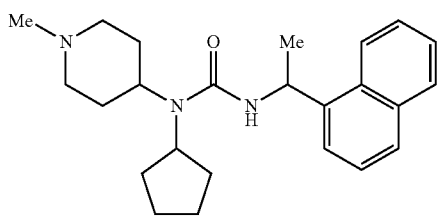 [SMILES: CC(NC(=O)N(C1CCCC1)C1CCN(C)CC1)c1cccc2ccccc12] | 1-cyclopentyl-1-(1-methylpiperidin-4-yl)-3-(1-(naphthalen-1-yl)ethyl)urea, |
| GA52 | 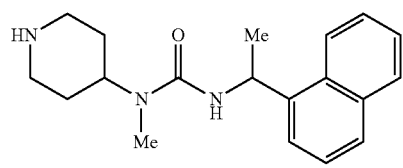 | 1-methyl-3-(1-(naphthalen-1-yl)ethyl)-1-(piperidin-4-yl)urea, |
| GA53 | 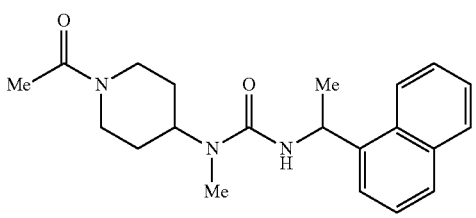 [SMILES: CC(=O)N1CCC(N(C)C(=O)NC(C)c2cccc3ccccc23)CC1] | 1-(1-acetylpiperidin-4-yl)-1-methyl-3-(1-(naphthalen-1-yl)ethyl)urea, |

-continued

| | | |
|---|---|---|
| GA54 | 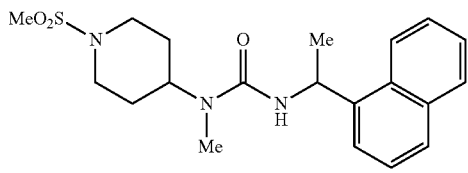 [SMILES: CC(NC(=O)N(C)C1CCN(S(C)(=O)=O)CC1)c1cccc2ccccc12] | 1-methyl-1-(1-(methylsulfonyl)piperidin-4-yl)-3-(1-(naphthalen-1-yl)ethyl)urea, |
| GA55 | 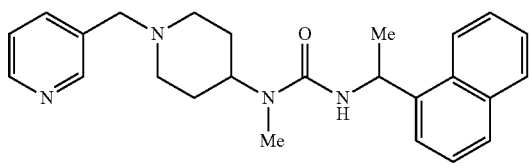 [SMILES: CC(NC(=O)N(C)C1CCN(Cc2cccnc2)CC1)c1cccc2ccccc12] | 1-methyl-3-(1-(naphthalen-1-yl)ethyl)-1-(1-(pyridin-3-ylmethyl)piperidin-4-yl)urea, |
| GA56 | 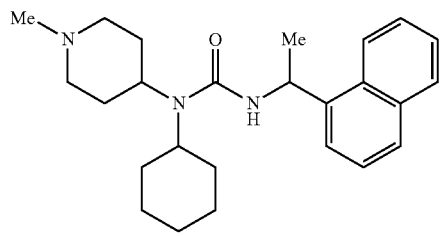 | 1-cyclohexyl-1-(1-methylpiperidin-4-yl)-3-(1-(naphthalen-1-yl)ethyl)urea, |
| GA57 | 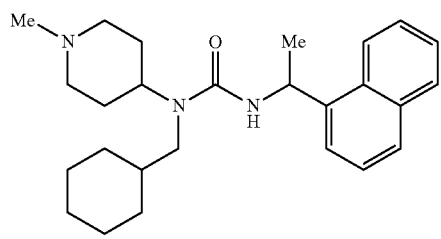 | 1-(cyclohexylmethyl)-1-(1-methylpiperidin-4-yl)-3-(1-(naphthalen-1-yl)ethyl)urea, |
| GA58 | 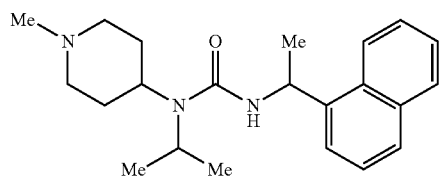 | 1-isopropyl-1-(1-methylpiperidin-4-yl)-3-(1-(naphthalen-1-yl)ethyl)urea, |
| GA59 | 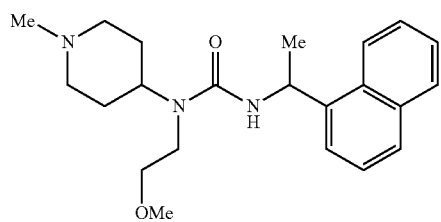 | 1-(2-methoxyethyl)-1-(1-methylpiperidin-4-yl)-3-(1-(naphthalen-1-yl)ethyl)urea, |
| GA60 | 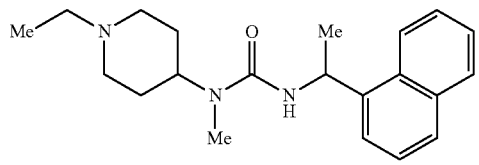 [SMILES: CCN1CCC(N(C)C(=O)NC(C)c2cccc3ccccc23)CC1] | 1-(1-ethylpiperidin-4-yl)-1-methyl-3-(1-(naphthalen-1-yl)ethyl)urea, |
| GA61 | 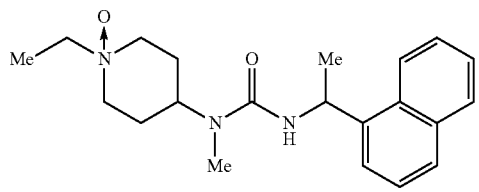 [SMILES: CC[N+]1([O-])CCC(N(C)C(=O)NC(C)c2cccc3ccccc23)CC1] | 1-ethyl-4-(1-methyl-3-(1-(naphthalen-1-yl)ethyl)ureido)piperidine 1-oxide, |

-continued

| | | |
|---|---|---|
| GA62 | 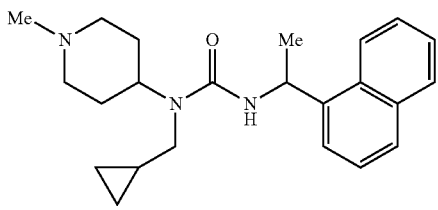 | 1-(cyclopropylmethyl)-1-(1-methylpiperidin-4-yl)-3-(1-(naphthalen-1-yl)ethyl)urea, |
| GA63 | 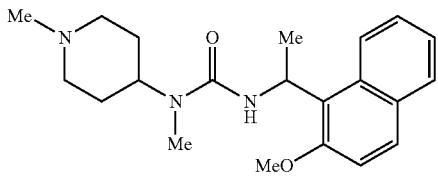 [SMILES: COc1ccc2ccccc2c1C(C)NC(=O)N(C)C1CCN(C)CC1] | 3-(1-(2-methoxynaphthalen-1-yl)ethyl)-1-methyl-1-(1-methylpiperidin-4-yl)urea, |
| GA64 | 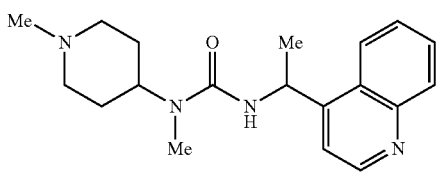 | 1-methyl-1-(1-methylpiperidin-4-yl)-3-(1-(quinolin-4-yl)ethyl)urea, |
| GA65 | 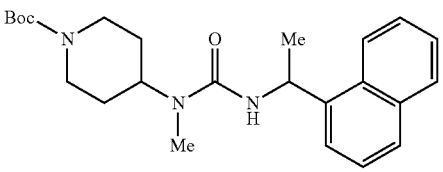 [SMILES: CC(NC(=O)N(C)C1CCN(C(=O)OC(C)(C)C)CC1)c1cccc2ccccc12] | tert-butyl 4-(1-methyl-3-(1-(naphthalen-1-yl)ethyl)ureido)piperidine-1-carboxylate, |
| GA66 | 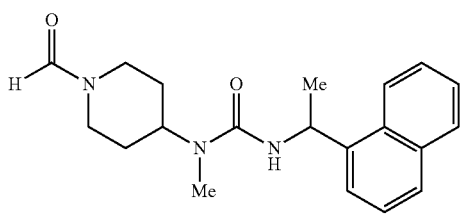 | 1-(1-formylpiperidin-4-yl)-1-methyl-3-(1-(naphthalen-1-yl)ethyl)urea, |
| GA67 | 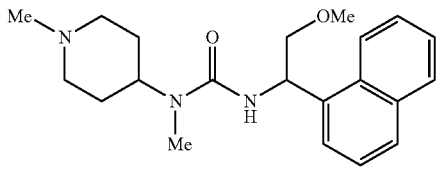 | 3-(2-methoxy-1-(naphthalen-1-yl)ethyl)-1-methyl-1-(1-methylpiperidin-4-yl)urea, |
| GA68 | 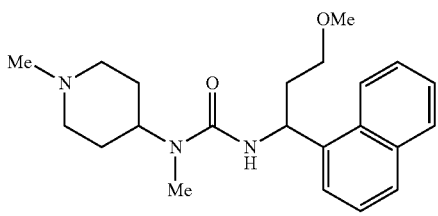 [SMILES: COCCC(NC(=O)N(C)C1CCN(C)CC1)c1cccc2ccccc12] | 3-(3-methoxy-1-(naphthalen-1-yl)propyl)-1-methyl-1-(1-methylpiperidin-4-yl)urea, |
| GA69 | 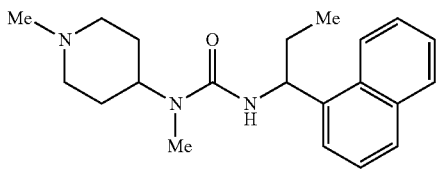 [SMILES: CCC(NC(=O)N(C)C1CCN(C)CC1)c1cccc2ccccc12] | 1-methyl-1-(1-methylpiperidin-4-yl)-3-(1-(naphthalen-1-yl)propyl)urea, |

-continued

| | | |
|---|---|---|
| GA70 | 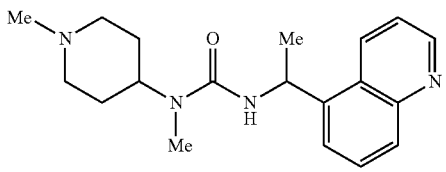 [SMILES: CC(NC(=O)N(C)C1CCN(C)CC1)c1cccc2ncccc12] | 1-methyl-1-(1-methylpiperidin-4-yl)-3-(1-(quinolin-5-yl)ethyl)urea, |
| GA71 | 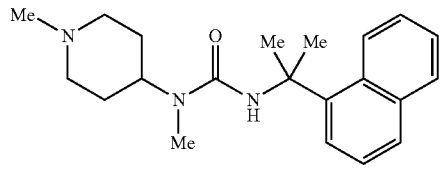 [SMILES: CN1CCC(N(C)C(=O)NC(C)(C)c2cccc3ccccc23)CC1] | 1-methyl-1-(1-methylpiperidin-4-yl)-3-(2-(naphthalen-1-yl)propan-2-yl)urea, |
| GA72 | 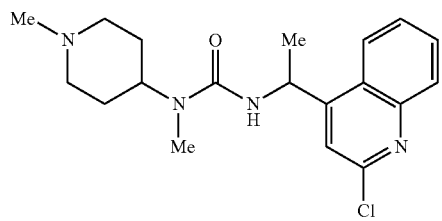 [SMILES: CC(NC(=O)N(C)C1CCN(C)CC1)c1cc(Cl)nc2ccccc12] | 3-(1-(2-chloroquinolin-4-yl)ethyl)-1-methyl-1-(1-methylpiperidin-4-yl)urea, |
| GA73 | 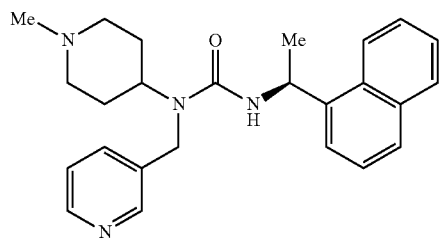 | (S)-1-(1-methylpiperidin-4-yl)-3-(1-(naphthalen-1-yl)ethyl)-1-(pyridin-3-ylmethyl)urea, |
| GA74 | 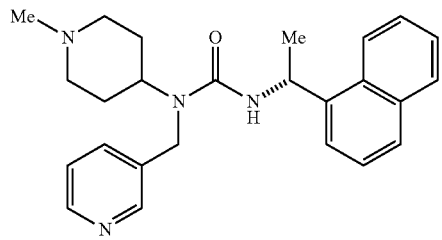 | (R)-1-(1-methylpiperidin-4-yl)-3-(1-(naphthalen-1-yl)ethyl)-1-(pyridin-3-ylmethyl)urea, |
| GA75 | 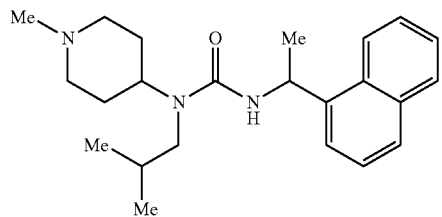 | 1-isobutyl-1-(1-methylpiperidin-4-yl)-3-(1-(naphthalen-1-yl)ethyl)urea, |
| GA76 | 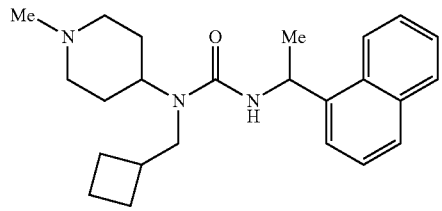 | 1-(cyclobutylmethyl)-1-(1-methylpiperidin-4-yl)-3-(1-(naphthalen-1-yl)ethyl)urea, |

-continued

| | | |
|---|---|---|
| GA77 | 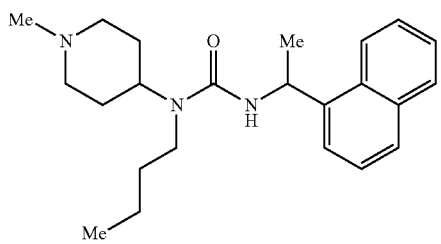 [SMILES: CCCCN(C(=O)NC(C)c1cccc2ccccc12)C1CCN(C)CC1] | 1-butyl-1-(1-methylpiperidin-4-yl)-3-(1-(naphthalen-1-yl)ethyl)urea, |
| GA78 | 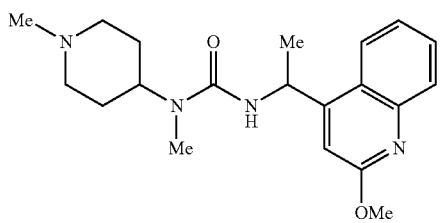 | 3-(1-(2-methoxyquinolin-4-yl)ethyl)-1-methyl-1-(1-methylpiperidin-4-yl)urea, |
| GA79 | 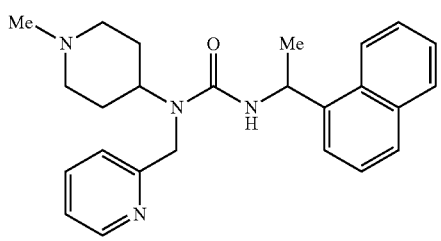 | 1-(1-methylpiperidin-4-yl)-3-(1-(naphthalen-1-yl)ethyl)-1-(pyridin-2-ylmethyl)urea, |
| GA80 | 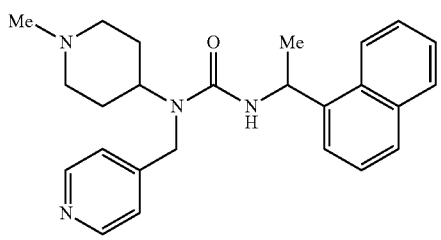 | 1-(1-methylpiperidin-4-yl)-3-(1-(naphthalen-1-yl)ethyl)-1-(pyridin-4-ylmethyl)urea, |
| GA81 | 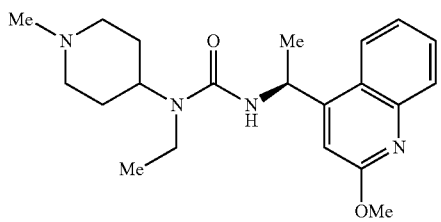 [SMILES: CCN(C(=O)N[C@@H](C)c1cc(OC)nc2ccccc12)C1CCN(C)CC1] | (S)-1-ethyl-3-(1-(2-methoxyquinolin-4-yl)ethyl)-1-(1-methylpiperidin-4-yl)urea, |
| GA82 | 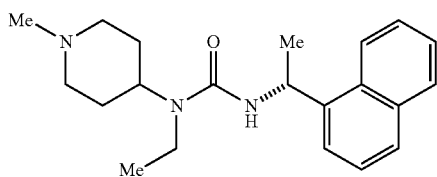 | (R)-1-ethyl-1-(1-methylpiperidin-4-yl)-3-(1-(naphthalen-1-yl)ethyl)urea, |
| GA83 | 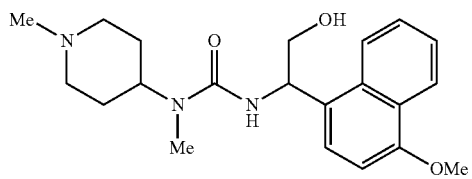 [SMILES: COc1ccc(C(CO)NC(=O)N(C)C2CCN(C)CC2)c2ccccc12] | 3-(2-hydroxy-1-(4-methoxynaphthalen-1-yl)ethyl)-1-methyl-1-(1-methylpiperidin-4-yl)urea, |

-continued

| | | |
|---|---|---|
| GA84 | 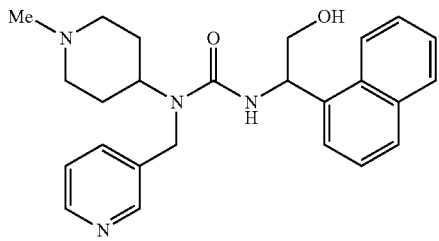 | 3-(2-hydroxy-1-(naphthalen-1-yl)ethyl)-1-(1-methylpiperidin-4-yl)-1-(pyridin-3-ylmethyl)urea, |
| GA85 | 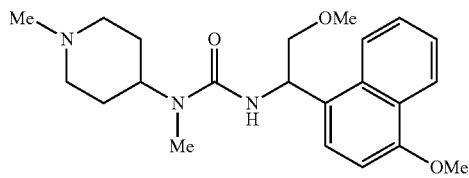 | 3-(2-methoxy-1-(4-methoxynaphthalen-1-yl)ethyl)-1-methyl-1-(1-methylpiperidin-4-yl)urea, |
| GA86 | 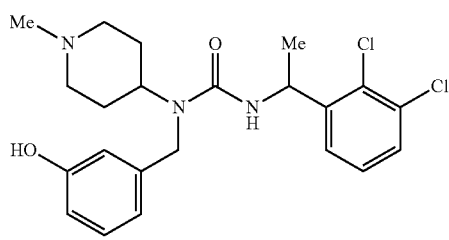 [SMILES: CC(NC(=O)N(Cc1cccc(O)c1)C1CCN(C)CC1)c1cccc(Cl)c1Cl] | 3-(1-(2,3-dichlorophenyl)ethyl)-1-(3-hydroxybenzyl)-1-(1-methylpiperidin-4-yl)urea, |
| GA87 | 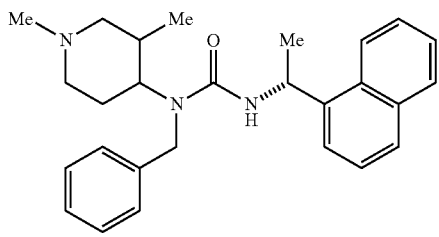 | 1-benzyl-1-(1,3-dimethylpiperidin-4-yl)-3-((R)-1-(naphthalen-1-yl)ethyl)urea, |
| GA88 | 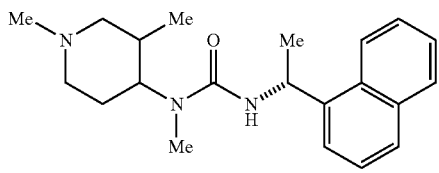 | 1-(1,3-dimethylpiperidin-4-yl)-1-methyl-3-((R)-1-(naphthalen-1-yl)ethyl)urea, |
| GA89 | 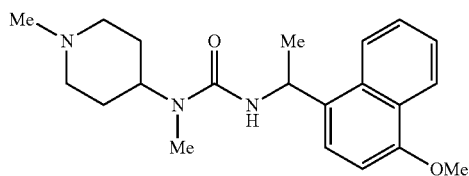 | 3-(1-(4-methoxynaphthalen-1-yl)ethyl)-1-methyl-1-(1-methylpiperidin-4-yl)urea, |
| GA90 | 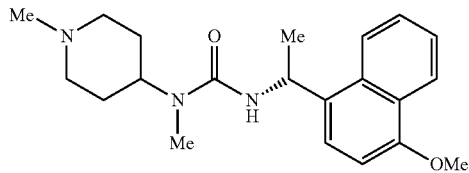 | (R)-3-(1-(4-methoxynaphthalen-1-yl)ethyl)-1-methyl-1-(1-methylpiperidin-4-yl)urea, |
| GA91 | 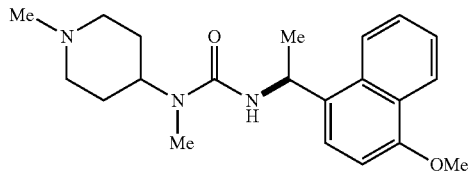 | (S)-3-(1-(4-methoxynaphthalen-1-yl)ethyl)-1-methyl-1-(1-methylpiperidin-4-yl)urea, |

-continued

| | | |
|---|---|---|
| GA92 | 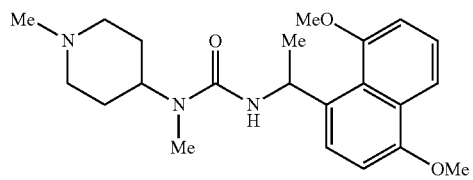 [SMILES: COc1ccc(C(C)NC(=O)N(C)C2CCN(C)CC2)c2c(OC)cccc12] | 3-(1-(4,8-dimethoxynaphthalen-1-yl)ethyl)-1-methyl-1-(1-methylpiperidin-4-yl)urea, |
| GA93 | 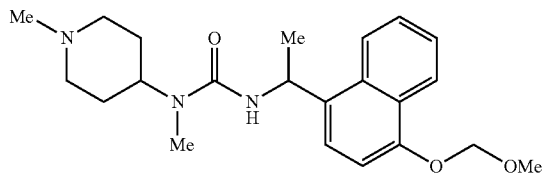 [SMILES: COCOc1ccc(C(C)NC(=O)N(C)C2CCN(C)CC2)c2ccccc12] | 3-(1-(4-(methoxymethoxy)naphthalen-1-yl)ethyl)-1-methyl-1-(1-methylpiperidin-4-yl)urea, |
| GA94 | 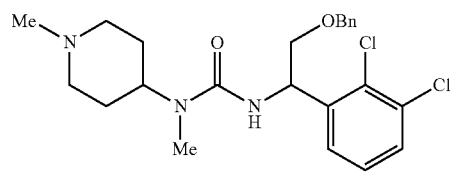 | 3-(2-(benzyloxy)-1-(2,3-dichlorophenyl)ethyl)-1-methyl-1-(1-methylpiperidin-4-yl)urea, |
| GA95 | 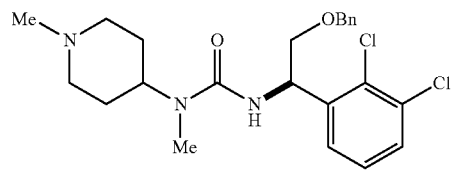 | (R)-3-(2-(benzyloxy)-1-(2,3-dichlorophenyl)ethyl)-1-methyl-1-(1-methylpiperidin-4-yl)urea, |
| GA96 | 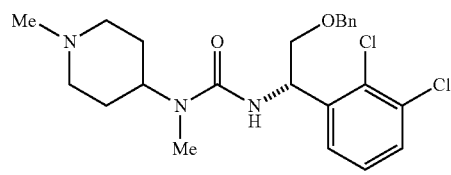 | (S)-3-(2-(benzyloxy)-1-(2,3-dichlorophenyl)ethyl)-1-methyl-1-(1-methylpiperidin-4-yl)urea, |
| GA97 | 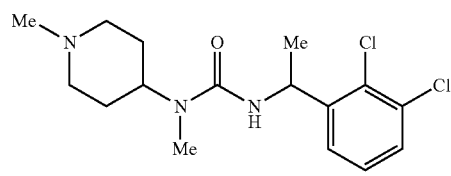 [SMILES: CC(NC(=O)N(C)C1CCN(C)CC1)c1cccc(Cl)c1Cl] | 3-(1-(2,3-dichlorophenyl)ethyl)-1-methyl-1-(1-methylpiperidin-4-yl)urea, |
| GA98 | 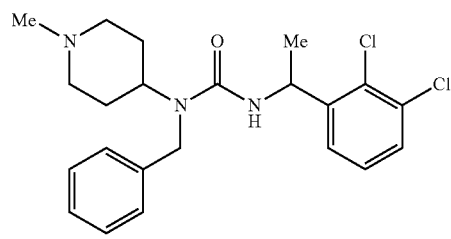 [SMILES: CC(NC(=O)N(Cc1ccccc1)C1CCN(C)CC1)c1cccc(Cl)c1Cl] | 1-benzyl-3-(1-(2,3-dichlorophenyl)ethyl)-1-(1-methylpiperidin-4-yl)urea, |
| GA99 | 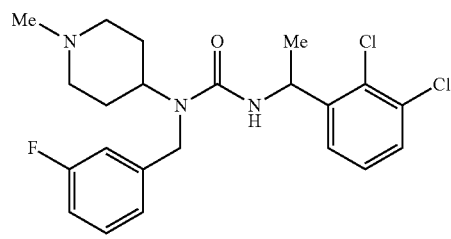 | 3-(1-(2,3-dichlorophenyl)ethyl)-1-(3-fluorobenzyl)-1-(1-methylpiperidin-4-yl)urea, |

| | | |
|---|---|---|
| GA100 | 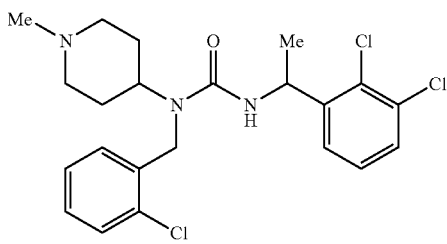 | 1-(2-chlorobenzyl)-3-(1-(2,3-dichlorophenyl)ethyl)-1-(1-methylpiperidin-4-yl)urea, |
| GA101 | 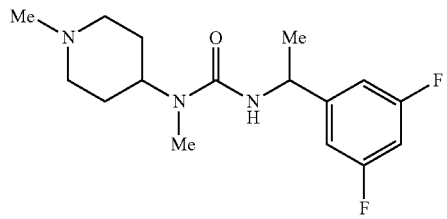 [SMILES: CC(NC(=O)N(C)C1CCN(C)CC1)c1cc(F)cc(F)c1] | 3-(1-(3,5-difluorophenyl)ethyl)-1-methyl-1-(1-methylpiperidin-4-yl)urea, |
| GA102 | 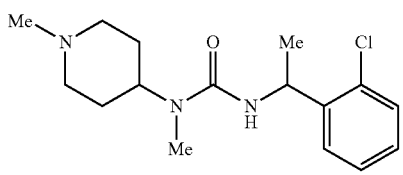 [SMILES: CC(NC(=O)N(C)C1CCN(C)CC1)c1ccccc1Cl] | 3-(1-(2-chlorophenyl)ethyl)-1-methyl-1-(1-methylpiperidin-4-yl)urea, |
| GA103 | 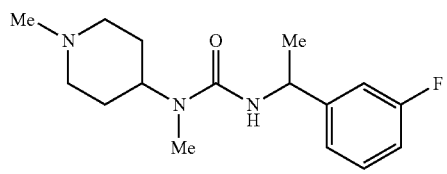 [SMILES: CC(NC(=O)N(C)C1CCN(C)CC1)c1cccc(F)c1] | 3-(1-(3-fluorophenyl)ethyl)-1-methyl-1-(1-methylpiperidin-4-yl)urea, |
| GA104 | 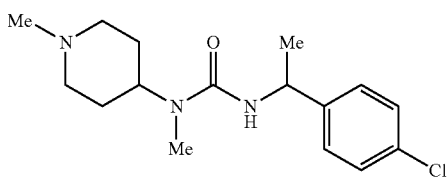 [SMILES: CC(NC(=O)N(C)C1CCN(C)CC1)c1ccc(Cl)cc1] | 3-(1-(4-chlorophenyl)ethyl)-1-methyl-1-(1-methylpiperidin-4-yl)urea, |
| GA105 | 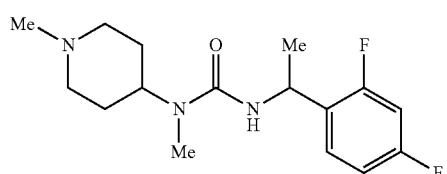 | 3-(1-(2,4-difluorophenyl)ethyl)-1-methyl-1-(1-methylpiperidin-4-yl)urea, |
| GA106 | 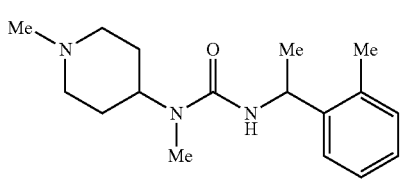 | 1-methyl-1-(1-methylpiperidin-4-yl)-3-(1-(o-tolyl)ethyl)urea, |
| GA107 | 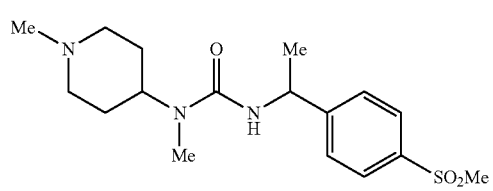 [SMILES: CC(NC(=O)N(C)C1CCN(C)CC1)c1ccc(S(C)(=O)=O)cc1] | 1-methyl-1-(1-methylpiperidin-4-yl)-3-(1-(4-(methylsulfonyl)phenyl)ethyl)urea, |

| | | |
|---|---|---|
| GA108 | 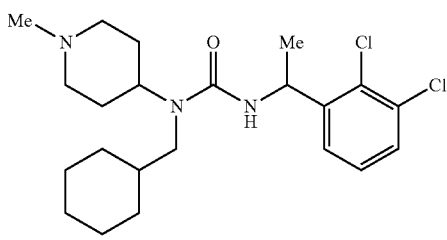 [SMILES: CC(NC(=O)N(CC1CCCCC1)C1CCN(C)CC1)c1cccc(Cl)c1Cl] | 1-(cyclohexylmethyl)-3-(1-(2,3-dichlorophenyl)ethyl)-1-(1-methylpiperidin-4-yl)urea, |
| GA109 | 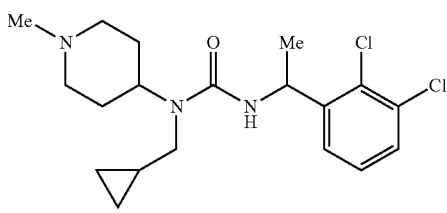 [SMILES: CC(NC(=O)N(CC1CC1)C1CCN(C)CC1)c1cccc(Cl)c1Cl] | 1-(cyclopropylmethyl)-3-(1-(2,3-dichlorophenyl)ethyl)-1-(1-methylpiperidin-4-yl)urea, |
| GA110 | 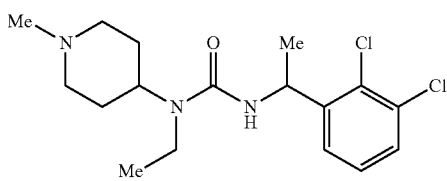 | 3-(1-(2,3-dichlorophenyl)ethyl)-1-ethyl-1-(1-methylpiperidin-4-yl)urea, |
| GA111 | 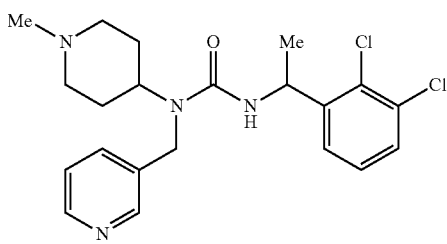 [SMILES: CC(NC(=O)N(Cc1cccnc1)C1CCN(C)CC1)c1cccc(Cl)c1Cl] | 3-(1-(2,3-dichlorophenyl)ethyl)-1-(1-methylpiperidin-4-yl)-1-(pyridin-3-ylmethyl)urea, |
| GA112 | 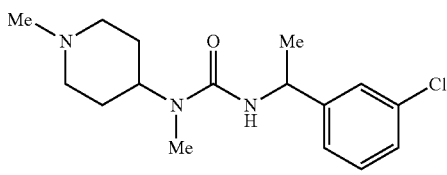 [SMILES: CC(NC(=O)N(C)C1CCN(C)CC1)c1cccc(Cl)c1] | 3-(1-(3-chlorophenyl)ethyl)-1-methyl-1-(1-methylpiperidin-4-yl)urea, |
| GA113 | 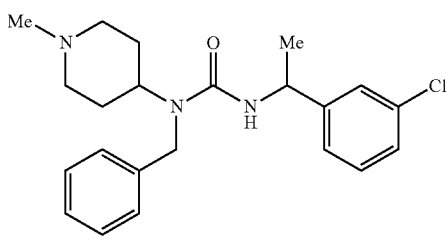 [SMILES: CC(NC(=O)N(Cc1ccccc1)C1CCN(C)CC1)c1cccc(Cl)c1] | 1-benzyl-3-(1-(3-chlorophenyl)ethyl)-1-(1-methylpiperidin-4-yl)urea, |
| GA114 | 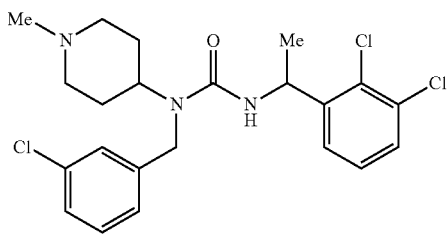 [SMILES: CC(NC(=O)N(Cc1cccc(Cl)c1)C1CCN(C)CC1)c1cccc(Cl)c1Cl] | 1-(3-chlorobenzyl)-3-(1-(2,3-dichlorophenyl)ethyl)-1-(1-methylpiperidin-4-yl)urea, |

-continued

| | | |
|---|---|---|
| GA115 | 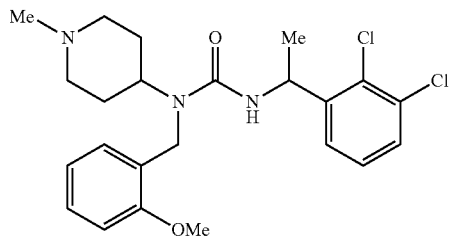 [SMILES: COc1ccccc1CN(C(=O)NC(C)c1cccc(Cl)c1Cl)C1CCN(C)CC1] | 3-(1-(2,3-dichlorophenyl)ethyl)-1-(2-methoxybenzyl)-1-(1-methylpiperidin-4-yl)urea, |
| GA116 | 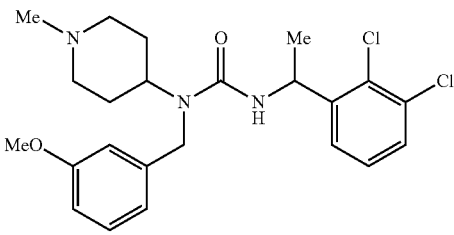 [SMILES: COc1cccc(CN(C(=O)NC(C)c2cccc(Cl)c2Cl)C2CCN(C)CC2)c1] | 3-(1-(2,3-dichlorophenyl)ethyl)-1-(3-methoxybenzyl)-1-(1-methylpiperidin-4-yl)urea, |
| GA117 | 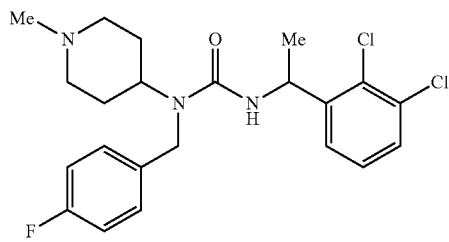 | 3-(1-(2,3-dichlorophenyl)ethyl)-1-(4-fluorobenzyl)-1-(1-methylpiperidin-4-yl)urea, |
| GA118 | 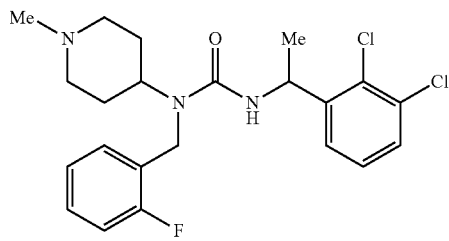 | 3-(1-(2,3-dichlorophenyl)ethyl)-1-(2-fluorobenzyl)-1-(1-methylpiperidin-4-yl)urea, |
| GA119 | 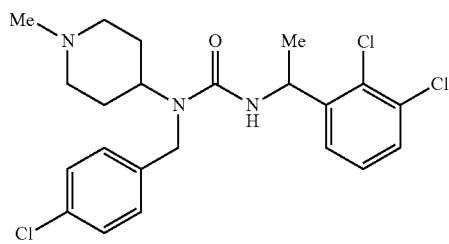 | 1-(4-chlorobenzyl)-3-(1-(2,3-dichlorophenyl)ethyl)-1-(1-methylpiperidin-4-yl)urea, |
| GA120 | 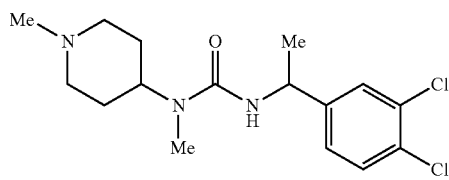 [SMILES: CC(NC(=O)N(C)C1CCN(C)CC1)c1ccc(Cl)c(Cl)c1] | 3-(1-(3,4-dichlorophenyl)ethyl)-1-methyl-1-(1-methylpiperidin-4-yl)urea, |
| GA121 | 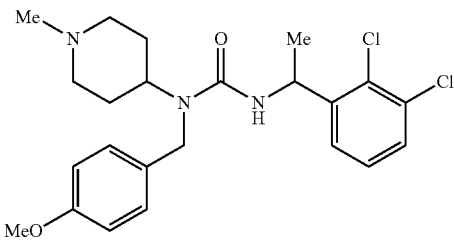 [SMILES: COc1ccc(CN(C(=O)NC(C)c2cccc(Cl)c2Cl)C2CCN(C)CC2)cc1] | 3-(1-(2,3-dichlorophenyl)ethyl)-1-(4-methoxybenzyl)-1-(1-methylpiperidin-4-yl)urea, |

| | | |
|---|---|---|
| GA122 | 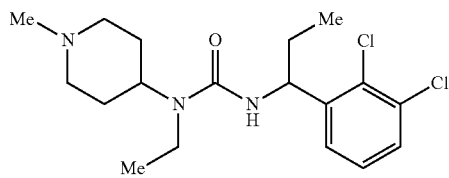 [SMILES: CCC(NC(=O)N(CC)C1CCN(C)CC1)c1cccc(Cl)c1Cl] | 3-(1-(2,3-dichlorophenyl)propyl)-1-ethyl-1-(1-methylpiperidin-4-yl)urea, |
| GA123 | 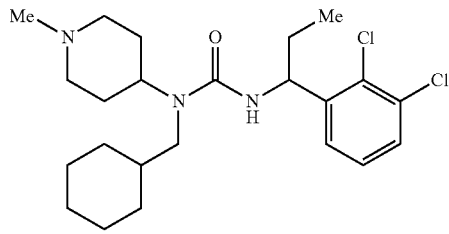 [SMILES: CCC(NC(=O)N(CC1CCCCC1)C1CCN(C)CC1)c1cccc(Cl)c1Cl] | 1-(cyclohexylmethyl)-3-(1-(2,3-dichlorophenyl)propyl)-1-(1-methylpiperidin-4-yl)urea, |
| GA124 | 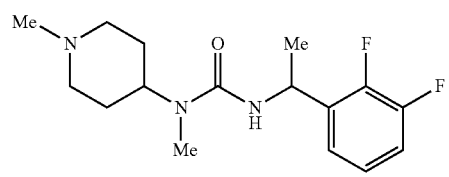 [SMILES: CC(NC(=O)N(C)C1CCN(C)CC1)c1cccc(F)c1F] | 3-(1-(2,3-difluorophenyl)ethyl)-1-methyl-1-(1-methylpiperidin-4-yl)urea, |
| GA125 | 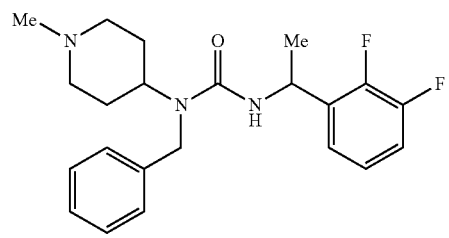 [SMILES: CC(NC(=O)N(Cc1ccccc1)C1CCN(C)CC1)c1cccc(F)c1F] | 1-benzyl-3-(1-(2,3-difluorophenyl)ethyl)-1-(1-methylpiperidin-4-yl)urea, |
| GA126 | 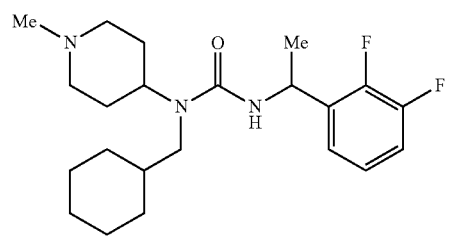 [SMILES: CC(NC(=O)N(CC1CCCCC1)C1CCN(C)CC1)c1cccc(F)c1F] | 1-(cyclohexylmethyl)-3-(1-(2,3-difluorophenyl)ethyl)-1-(1-methylpiperidin-4-yl)urea, |
| GA127 | 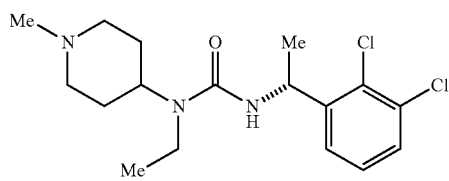 | (R)-3-(1-(2,3-dichlorophenyl)ethyl)-1-ethyl-1-(1-methylpiperidin-4-yl)urea, |
| GA128 | 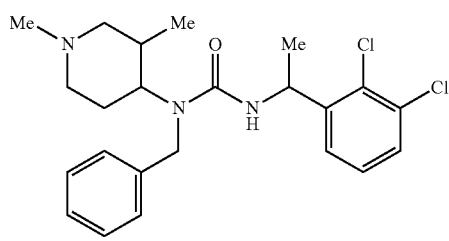 [SMILES: CC(NC(=O)N(Cc1ccccc1)C1CCN(C)CC1C)c1cccc(Cl)c1Cl] | 1-benzyl-3-(1-(2,3-dichlorophenyl)ethyl)-1-(1,3-dimethylpiperidin-4-yl)urea, |

-continued

| | | |
|---|---|---|
| GA129 | 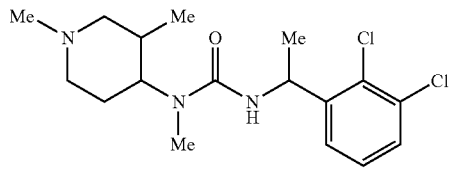 [SMILES: CC(NC(=O)N(C)C1CCN(C)CC1C)c1cccc(Cl)c1Cl] | 3-(1-(2,3-dichlorophenyl)ethyl)-1-(1,3-dimethylpiperidin-4-yl)-1-methylurea, |
| GA130 | 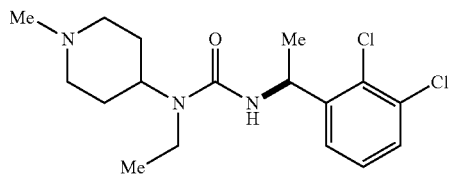 | (S)-3-(1-(2,3-dichlorophenyl)ethyl)-1-ethyl-1-(1-methylpiperidin-4-yl)urea, |
| GA131 | 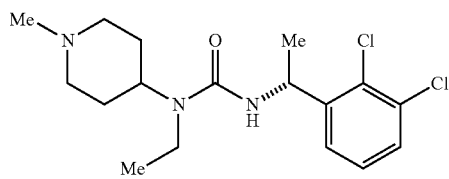 | (R)-3-(1-(2,3-dichlorophenyl)ethyl)-1-ethyl-1-(1-methylpiperidin-4-yl)urea, |
| GA132 | 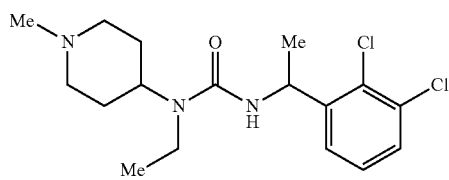 | 3-(1-(2,3-dichlorophenyl)ethyl)-1-ethyl-1-(1-methylpiperidin-4-yl)urea, |
| GA133 | 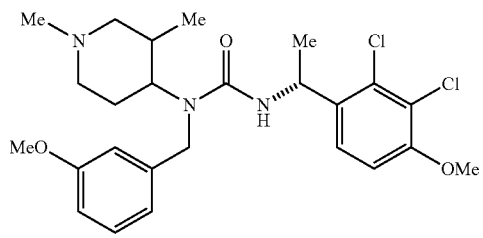 | 3-((R)-1-(2,3-dichloro-4-methoxyphenyl)ethyl)-1-(1,3-dimethylpiperidin-4-yl)-1-(3-methoxybenzyl)urea, |
| GA134 | 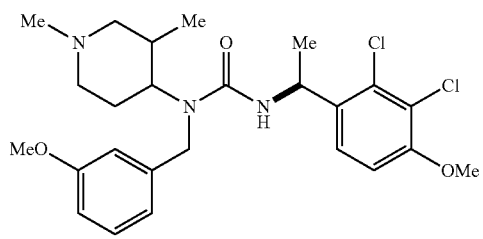 | 3-((S)-1-(2,3-dichloro-4-methoxyphenyl)ethyl)-1-(1,3-dimethylpiperidin-4-yl)-1-(3-methoxybenzyl)urea, |
| GA135 | 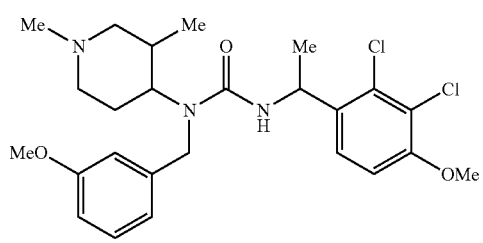 [SMILES: COc1cccc(CN(C(=O)NC(C)c2ccc(OC)c(Cl)c2Cl)C2CCN(C)CC2C)c1] | 3-(1-(2,3-dichloro-4-methoxyphenyl)ethyl)-1-(1,3-dimethylpiperidin-4-yl)-1-(3-methoxybenzyl)urea, |

-continued

| | | |
|---|---|---|
| GA136 | 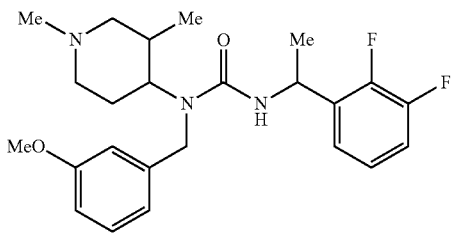 [SMILES: COc1cccc(CN(C(=O)NC(C)c2cccc(F)c2F)C2CCN(C)CC2C)c1] | 3-(1-(2,3-difluorophenyl)ethyl)-1-(1,3-dimethylpiperidin-4-yl)-1-(3-methoxybenzyl)urea, |
| GA137 | 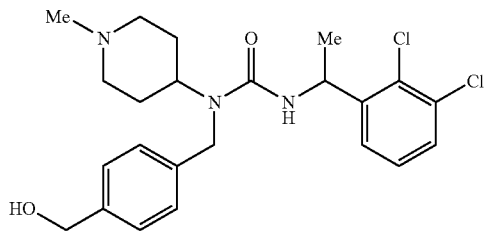 [SMILES: CC(NC(=O)N(Cc1ccc(CO)cc1)C1CCN(C)CC1)c1cccc(Cl)c1Cl] | 3-(1-(2,3-dichlorophenyl)ethyl)-1-(4-(hydroxymethyl)benzyl)-1-(1-methylpiperidin-4-yl)urea, |
| GA138 | 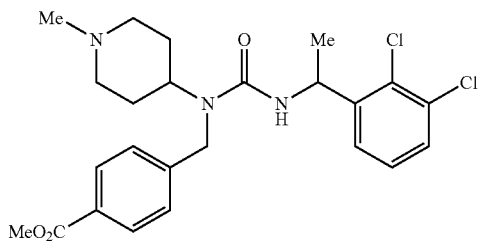 | methyl 4-((3-(1-(2,3-dichlorophenyl)ethyl)-1-(1-methylpiperidin-4-yl)ureido)methyl)benzoate, |
| GA139 | 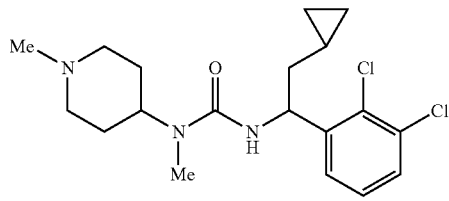 [SMILES: CN1CCC(N(C)C(=O)NC(CC2CC2)c2cccc(Cl)c2Cl)CC1] | 3-(2-cyclopropyl-1-(2,3-dichlorophenyl)ethyl)-1-methyl-1-(1-methylpiperidin-4-yl)urea, |
| GA140 | 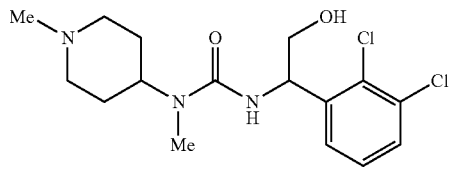 [SMILES: CN1CCC(N(C)C(=O)NC(CO)c2cccc(Cl)c2Cl)CC1] | 3-(1-(2,3-dichlorophenyl)-2-hydroxyethyl)-1-methyl-1-(1-methylpiperidin-4-yl)urea, |
| GA141 | 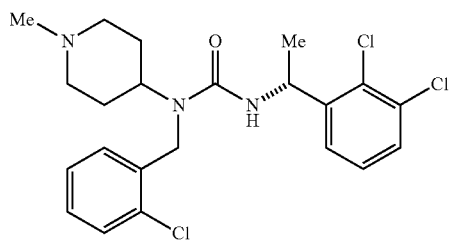 | (R)-1-(2-chlorobenzyl)-3-(1-(2,3-dichlorophenyl)ethyl)-1-(1-methylpiperidin-4-yl)urea, |
| GA142 | 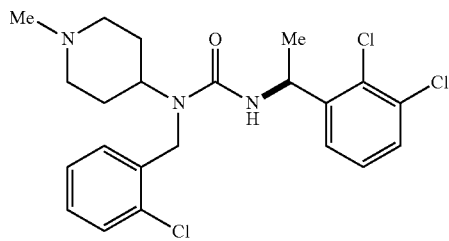 | (S)-1-(2-chlorobenzyl)-3-(1-(2,3-dichlorophenyl)ethyl)-1-(1-methylpiperidin-4-yl)urea, |

-continued

| | | |
|---|---|---|
| GA143 | 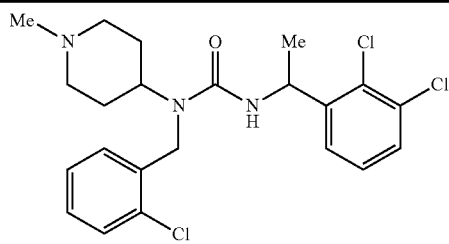 | 1-(2-chlorobenzyl)-3-(1-(2,3-dichlorophenyl)ethyl)-1-(1-methylpiperidin-4-yl)urea, |
| GA144 | 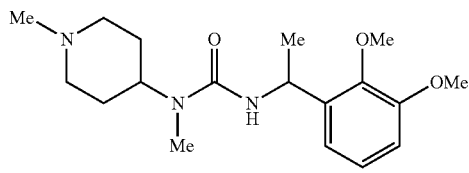 [SMILES: COc1cccc(C(C)NC(=O)N(C)C2CCN(C)CC2)c1OC] | 3-(1-(2,3-dimethoxyphenyl)ethyl)-1-methyl-1-(1-methylpiperidin-4-yl)urea, |
| GA145 | 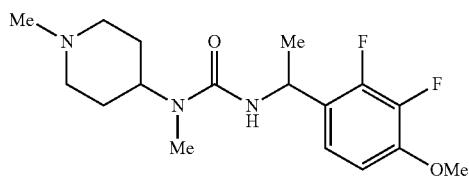 | 3-(1-(2,3-difluoro-4-methoxyphenyl)ethyl)-1-methyl-1-(1-methylpiperidin-4-yl)urea, |
| GA146 | 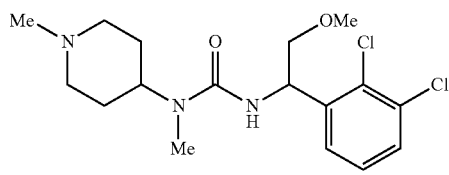 | 3-(1-(2,3-dichlorophenyl)-2-methoxyethyl)-1-methyl-1-(1-methylpiperidin-4-yl)urea, |
| GA147 | 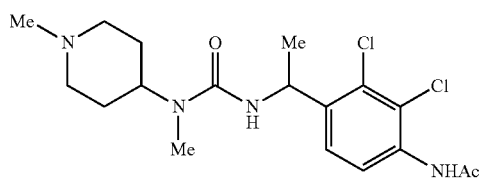 [SMILES: CC(=O)Nc1ccc(C(C)NC(=O)N(C)C2CCN(C)CC2)c(Cl)c1Cl] | N-(2,3-dichloro-4-(1-(3-methyl-3-(1-methylpiperidin-4-yl)ureido)ethyl)phenyl)acetamide, |
| GA148 | 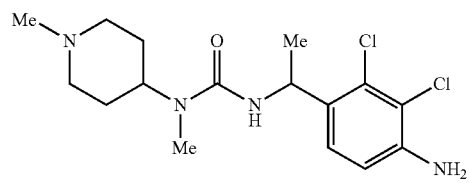 [SMILES: CC(NC(=O)N(C)C1CCN(C)CC1)c1ccc(N)c(Cl)c1Cl] | 3-(1-(4-amino-2,3-dichlorophenyl)ethyl)-1-methyl-1-(1-methylpiperidin-4-yl)urea, |
| GA149 | 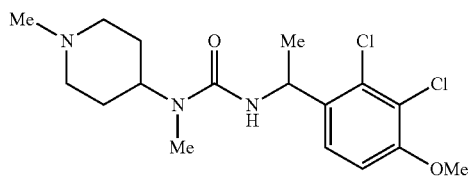 | 3-(1-(2,3-dichloro-4-methoxyphenyl)ethyl)-1-methyl-1-(1-methylpiperidin-4-yl)urea, |
| GA150 | 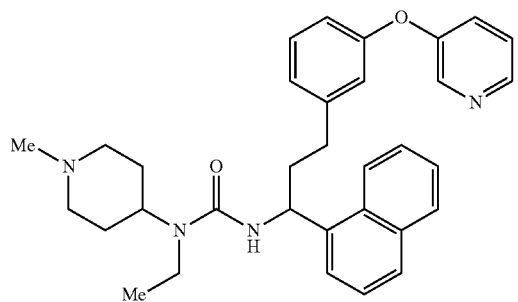 [SMILES: CCN(C(=O)NC(CCc1cccc(Oc2cccnc2)c1)c1cccc2ccccc12)C1CCN(C)CC1] | 1-ethyl-1-(1-methylpiperidin-4-yl)-3-(1-(naphthalen-1-yl)-3-(3-(pyridin-3-yloxy)phenyl)propyl)urea, |

-continued
GA151 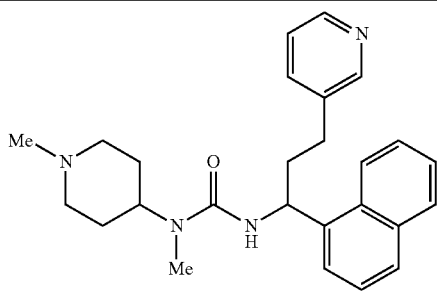 1-methyl-1-(1-methylpiperidin-4-yl)-3-(1-(naphthalen-1-yl)-3-(pyridin-3-yl)propyl)urea,
GA152 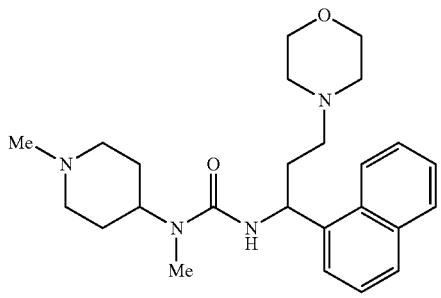 [SMILES: CN1CCC(N(C)C(=O)NC(CCN2CCOCC2)c2cccc3ccccc23)CC1] 1-methyl-1-(1-methylpiperidin-4-yl)-3-(3-morpholino-1-(naphthalen-1-yl)propyl)urea,
GA153 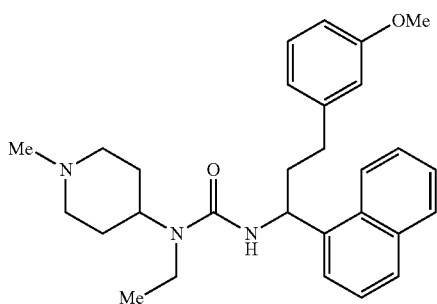 1-ethyl-3-(3-(3-methoxyphenyl)-1-(naphthalen-1-yl)propyl)-1-(1-methylpiperidin-4-yl)urea,
GA154 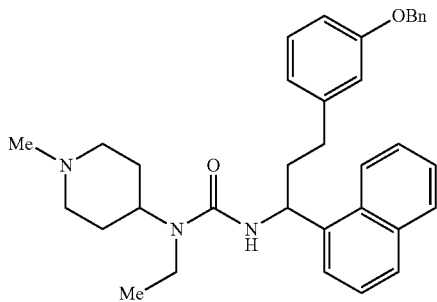 3-(3-(3-(benzyloxy)phenyl)-1-(naphthalen-1-yl)propyl)-1-ethyl-1-(1-methylpiperidin-4-yl)urea,
GA155 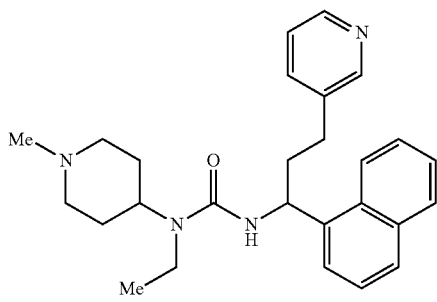 1-ethyl-1-(1-methylpiperidin-4-yl)-3-(1-(naphthalen-1-yl)-3-(pyridin-3-yl)propyl)urea,

| | | |
|---|---|---|
| GA156 | 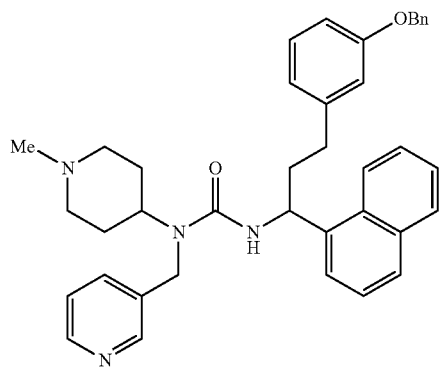 [SMILES: CN1CCC(N(Cc2cccnc2)C(=O)NC(CCc2cccc(OCc3ccccc3)c2)c2cccc3ccccc23)CC1] | 3-(3-(3-(benzyloxy)phenyl)-1-(naphthalen-1-yl)propyl)-1-(1-methylpiperidin-4-yl)-1-(pyridin-3-ylmethyl)urea, |
| GA157 | 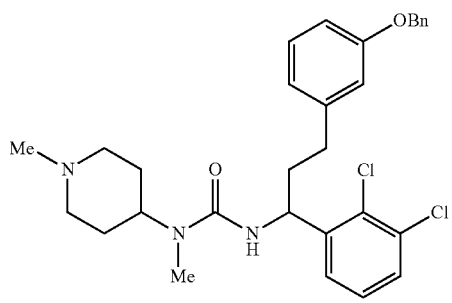 [SMILES: CN1CCC(N(C)C(=O)NC(CCc2cccc(OCc3ccccc3)c2)c2cccc(Cl)c2Cl)CC1] | 3-(3-(3-(benzyloxy)phenyl)-1-(2,3-dichlorophenyl)propyl)-1-methyl-1-(1-methylpiperidin-4-yl)urea, |
| GA158 | 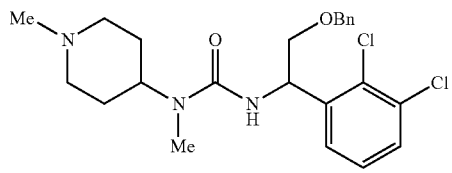 | 3-(2-(benzyloxy)-1-(2,3-dichlorophenyl)ethyl)-1-methyl-1-(1-methylpiperidin-4-yl)urea, |
| GA159 | 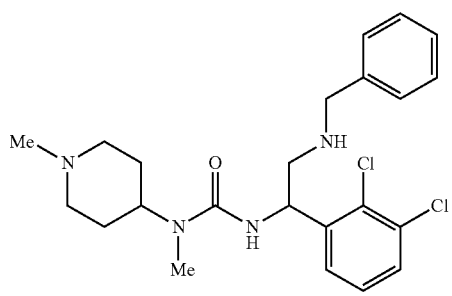 [SMILES: CN1CCC(N(C)C(=O)NC(CNCc2ccccc2)c2cccc(Cl)c2Cl)CC1] | 3-(2-(benzylamino)-1-(2,3-dichlorophenyl)ethyl)-1-methyl-1-(1-methylpiperidin-4-yl)urea, |
| GA160 | 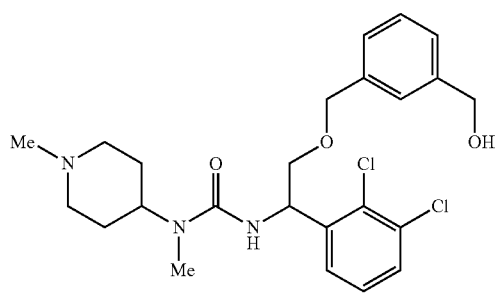 [SMILES: CN1CCC(N(C)C(=O)NC(COCc2cccc(CO)c2)c2cccc(Cl)c2Cl)CC1] | 3-(1-(2,3-dichlorophenyl)-2((3-(hydroxymethyl)benzyl)oxy)ethyl)-1-methyl-1-(1-methylpiperidin-4-yl)urea, |

-continued

| | | |
|---|---|---|
| GA161 | 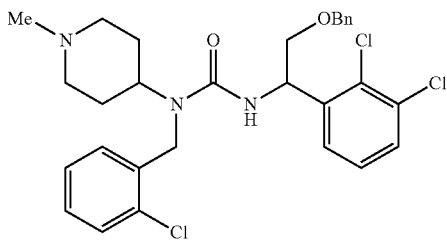 [SMILES: CN1CCC(N(Cc2ccccc2Cl)C(=O)NC(COCc2ccccc2)c2cccc(Cl)c2Cl)CC1] | 3-(2-(benzyloxy)-1-(2,3-dichlorophenyl)ethyl)-1-(2-chlorobenzyl)-1-(1-methylpiperidin-4-yl)urea, |
| GA162 | 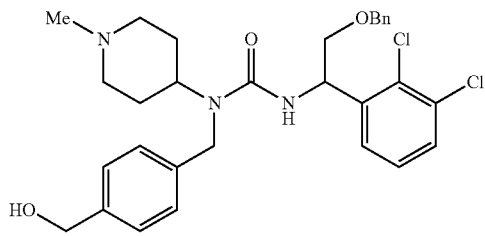 [SMILES: CN1CCC(N(Cc2ccc(CO)cc2)C(=O)NC(COCc2ccccc2)c2cccc(Cl)c2Cl)CC1] | 3-(2-(benzyloxy)-1-(2,3-dichlorophenyl)ethyl)-1-(4-(hydroxymethyl)benzyl)-1-(1-methylpiperidin-4-yl)urea, |
| GA163 | 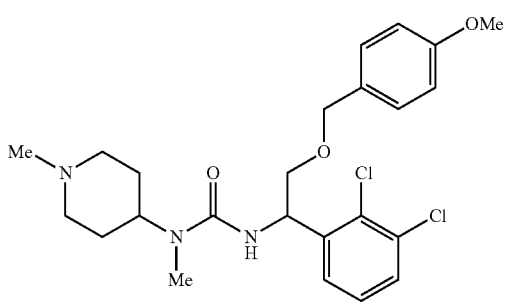 [SMILES: COc1ccc(COCC(NC(=O)N(C)C2CCN(C)CC2)c2cccc(Cl)c2Cl)cc1] | 3-(1-(2,3-dichlorophenyl)-2-((4-methoxybenzyl)oxy)ethyl)-1-methyl-1-(1-methylpiperidin-4-yl)urea, |
| GA164 | 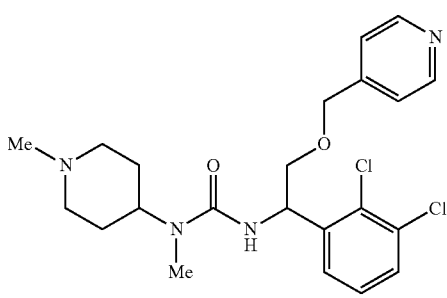 [SMILES: CN1CCC(N(C)C(=O)NC(COCc2ccncc2)c2cccc(Cl)c2Cl)CC1] | 3-(1-(2,3-dichlorophenyl)-2-(pyridin-4-ylmethoxy)ethyl)-1-methyl-1-(1-methylpiperidin-4-yl)urea, |
| GA165 | 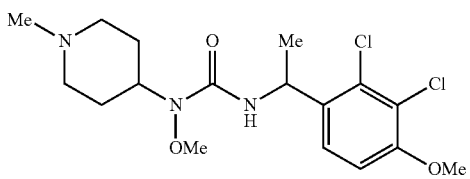 | 3-(1-(2,3-dichloro-4-methoxyphenyl)ethyl)-1-methoxy-1-(1-methylpiperidin-4-yl)urea, |
| GA166 | 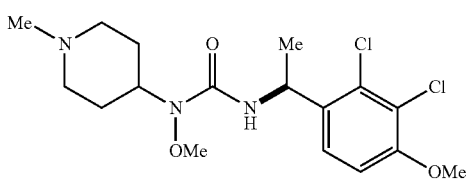 | (S)-3-(1-(2,3-dichloro-4-methoxyphenyl)ethyl)-1-methoxy-1-(1-methylpiperidin-4-yl)urea, |
| GA167 | 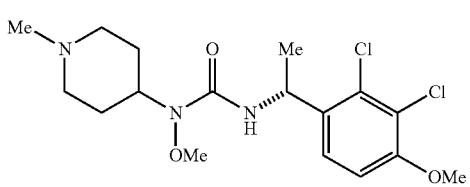 | (R)-3-(1-(2,3-dichloro-4-methoxyphenyl)ethyl)-1-methoxy-1-(1-methylpiperidin-4-yl)urea, |

-continued

| | | |
|---|---|---|
| GA168 | 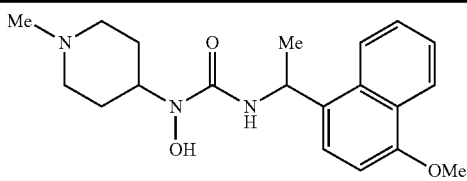 | 1-hydroxy-3-(1-(4-methoxynaphthalen-1-yl)ethyl)-1-(1-methylpiperidin-4-yl)urea, |
| GA169 | 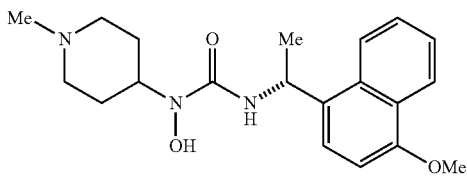 | (R)-1-hydroxy-3-(1-(4-methoxynaphthalen-1-yl)ethyl)-1-(1-methylpiperidin-4-yl)urea, |
| GA170 | 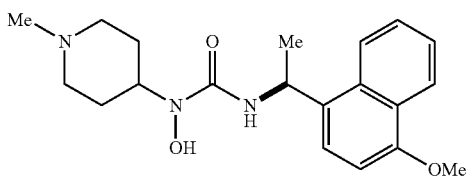 | (S)-1-hydroxy-3-(1-(4-methoxynaphthalen-1-yl)ethyl)-1-(1-methylpiperidin-4-yl)urea, |
| GA171 | 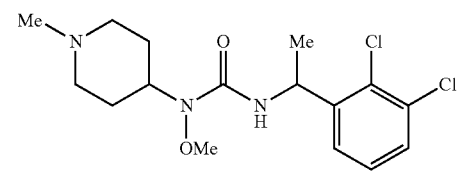 | 3-(1-(2,3-dichlorophenyl)ethyl)-1-methoxy-1-(1-methylpiperidin-4-yl)urea, |
| GA172 | 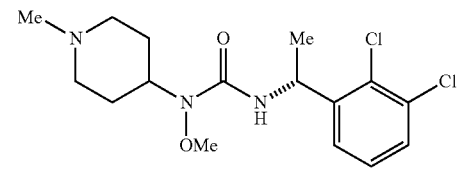 | (R)-3-(1-(2,3-dichlorophenyl)ethyl)-1-methoxy-1-(1-methylpiperidin-4-yl)urea, |
| GA173 | 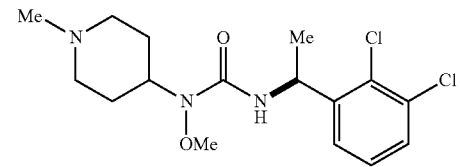 | (S)-3-(1-(2,3-dichlorophenyl)ethyl)-1-methoxy-1-(1-methylpiperidin-4-yl)urea, |
| GA174 | 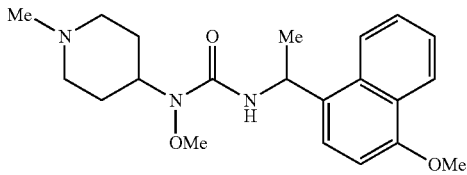 | 1-methoxy-3-(1-(4-methoxynaphthalen-1-yl)ethyl)-1-(1-methylpiperidin-4-yl)urea, |
| GA175 | 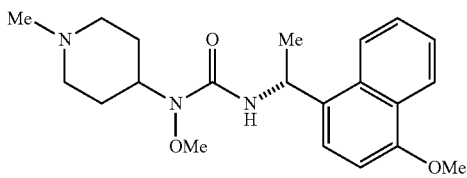 | (R)-1-methoxy-3-(1-(4-methoxynaphthalen-1-yl)ethyl)-1-(1-methylpiperidin-4-yl)urea, |
| GA176 | 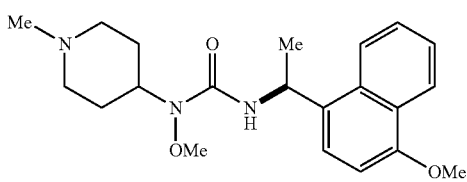 | (S)-1-methoxy-3-(1-(4-methoxynaphthalen-1-yl)ethyl)-1-(1-methylpiperidin-4-yl)urea, |

-continued

| | | |
|---|---|---|
| GA177 | 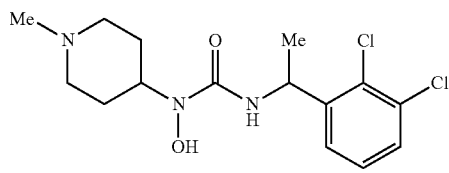 | 3-(1-(2,3-dichlorophenyl)ethyl)-1-hydroxy-1-(1-methylpiperidin-4-yl)urea, |
| GA178 | 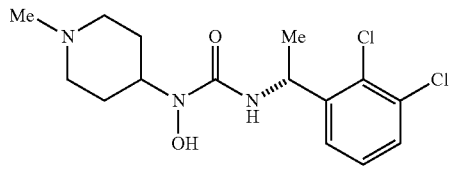 | (R)-3-(1-(2,3-dichlorophenyl)ethyl)-1-hydroxy-1-(1-methylpiperidin-4-yl)urea, |
| GA179 | 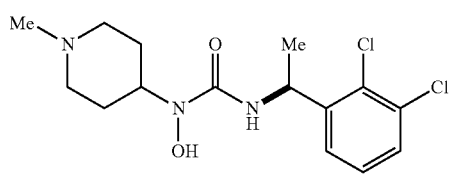 | (S)-3-(1-(2,3-dichlorophenyl)ethyl)-1-hydroxy-1-(1-methylpiperidin-4-yl)urea, |
| GA180 | 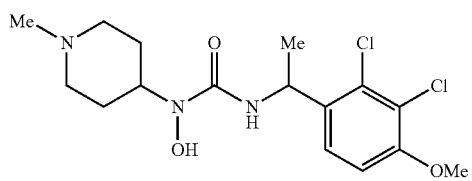 | 3-(1-(2,3-dichloro-4-methoxyphenyl)ethyl)-1-hydroxy-1-(1-methylpiperidin-4-yl)urea, |
| GA181 | 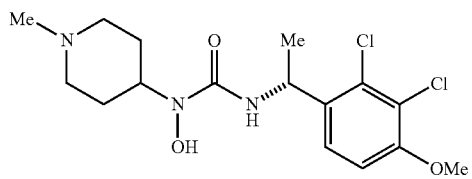 | (R)-3-(1-(2,3-dichloro-4-methoxyphenyl)ethyl)-1-hydroxy-1-(1-methylpiperidin-4-yl)urea, |
| GA182 | 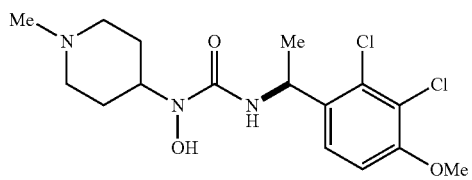 | (S)-3-(1-(2,3-dichloro-4-methoxyphenyl)ethyl)-1-hydroxy-1-(1-methylpiperidin-4-yl)urea, |
| GA183 | 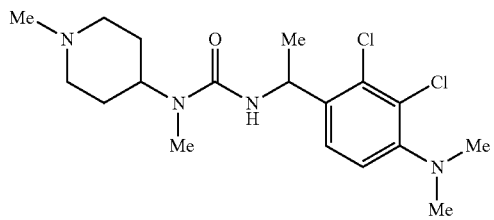 [SMILES: CC(NC(=O)N(C)C1CCN(C)CC1)c1ccc(N(C)C)c(Cl)c1Cl] | 3-(1-(2,3-dichloro-4-(dimethylamino)phenyl)ethyl)-1-methyl-1-(1-methylpiperidin-4-yl)urea, |
| GA184 | 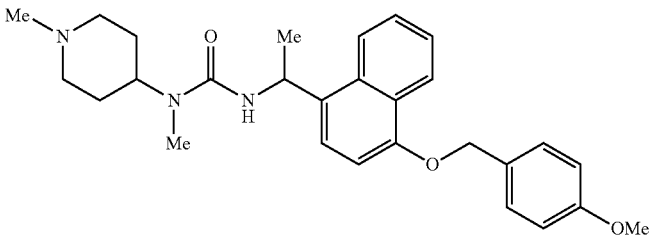 [SMILES: COc1ccc(COc2ccc(C(C)NC(=O)N(C)C3CCN(C)CC3)c3ccccc23)cc1] | 3-(1-(4-((4-methoxybenzyl)oxy)naphthalen-1-yl)ethyl)-1-methyl-1-(1-methylpiperidin-4-yl)urea, |

| | | |
|---|---|---|
| GA185 | 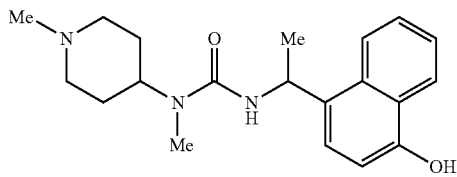 [SMILES: CC(NC(=O)N(C)C1CCN(C)CC1)c1ccc(O)c2ccccc12] | 3-(1-(4-hydroxynaphthalen-1-yl)ethyl)-1-methyl-1-(1-methylpiperidin-4-yl)urea, |
| GA186 | 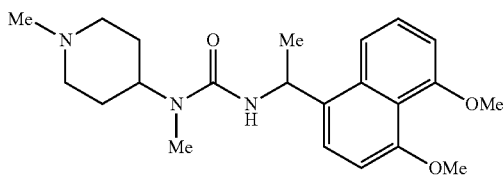 [SMILES: COc1cccc2c(C(C)NC(=O)N(C)C3CCN(C)CC3)ccc(OC)c12] | 3-(1-(4,5-dimethoxynaphthalen-1-yl)ethyl)-1-methyl-1-(1-methylpiperidin-4-yl)urea, |
| GA187 | 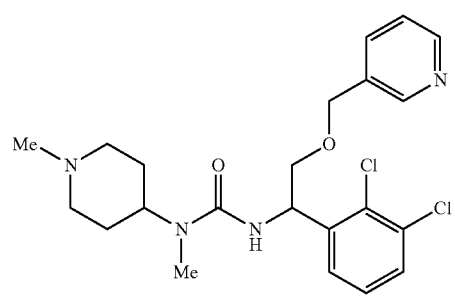 [SMILES: CN1CCC(N(C)C(=O)NC(COCc2cccnc2)c2cccc(Cl)c2Cl)CC1] | 3-(1-(2,3-dichlorophenyl)-2-(pyridin-3-ylmethoxy)ethyl)-1-methyl-1-(1-methylpiperidin-4-yl)urea, |
| GA188 | 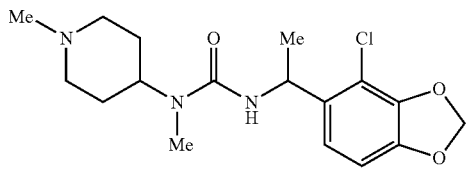 [SMILES: CC(NC(=O)N(C)C1CCN(C)CC1)c1ccc2c(c1Cl)OCO2] | 3-(1-(4-chlorobenzo[d][1,3]dioxol-5-yl)ethyl)-1-methyl-1-(1-methylpiperidin-4-yl)urea, |
| GA189 | 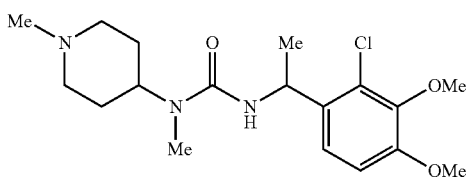 [SMILES: COc1ccc(C(C)NC(=O)N(C)C2CCN(C)CC2)c(Cl)c1OC] | 3-(1-(2-chloro-3,4-dimethoxyphenyl)ethyl)-1-methyl-1-(1-methylpiperidin-4-yl)urea, |
| GA190 | 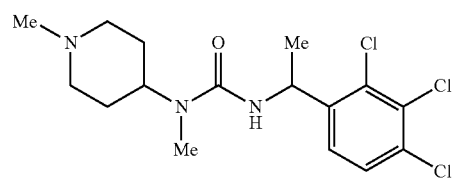 [SMILES: CC(NC(=O)N(C)C1CCN(C)CC1)c1ccc(Cl)c(Cl)c1Cl] | 1-methyl-1-(1-methylpiperidin-4-yl)-3-(1-(2,3,4-trichlorophenyl)ethyl)urea, |
| GA191 | 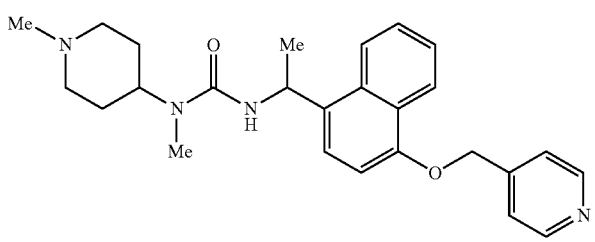 [SMILES: CC(NC(=O)N(C)C1CCN(C)CC1)c1ccc(OCc2ccncc2)c2ccccc12] | 1-methyl-1-(1-methylpiperidin-4-yl)-3-(1-(4-(pyridin-4-ylmethoxy)naphthalen-1-yl)ethyl)urea, |

| | | |
|---|---|---|
| GA192 | 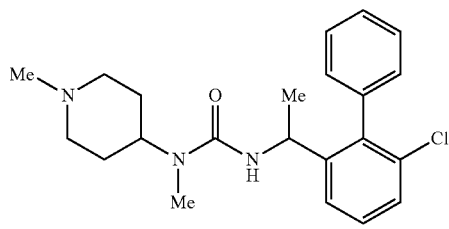 [SMILES: CC(NC(=O)N(C)C1CCN(C)CC1)c1cccc(Cl)c1-c1ccccc1] | 3-(1-(6-chloro-[1,1'-biphenyl]-2-yl)ethyl)-1-methyl-1-(1-methylpiperidin-4-yl)urea, |
| GA193 | 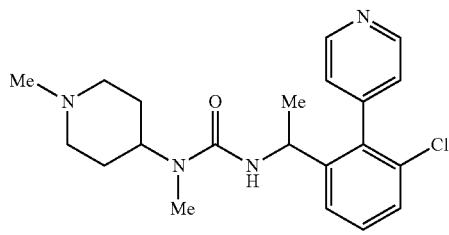 [SMILES: CC(NC(=O)N(C)C1CCN(C)CC1)c1cccc(Cl)c1-c1ccncc1] | 3-(1-(3-chloro-2-(pyridin-4-yl)phenyl)ethyl)-1-methyl-1-(1-methylpiperidin-4-yl)urea, |
| GA194 | 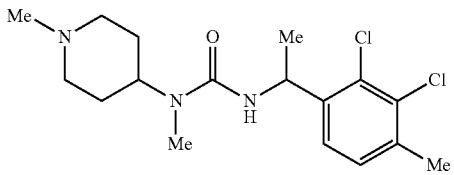 [SMILES: Cc1ccc(C(C)NC(=O)N(C)C2CCN(C)CC2)c(Cl)c1Cl] | 3-(1-(2,3-dichloro-4-methylphenyl)ethyl)-1-methyl-1-(1-methylpiperidin-4-yl)urea, |
| GA195 | 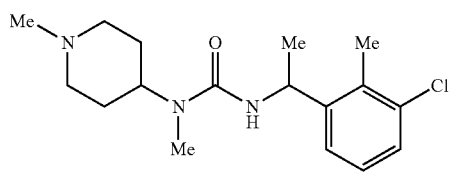 [SMILES: Cc1c(Cl)cccc1C(C)NC(=O)N(C)C1CCN(C)CC1] | 3-(1-(3-chloro-2-methylphenyl)ethyl)-1-methyl-1-(1-methylpiperidin-4-yl)urea, |
| GA196 | 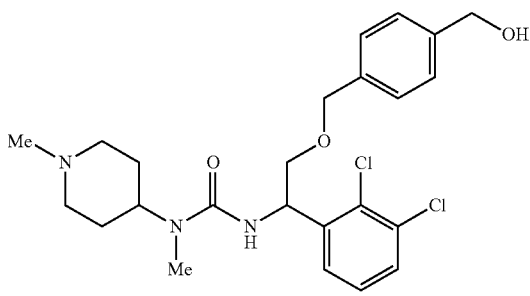 [SMILES: CN1CCC(N(C)C(=O)NC(COCc2ccc(CO)cc2)c2cccc(Cl)c2Cl)CC1] | 3-(1-(2,3-dichlorophenyl)-2-((4-(hydroxymethyl)benzyl)oxy)ethyl)-1-methyl-1-(1-methylpiperidin-4-yl)urea, |
| GA197 | 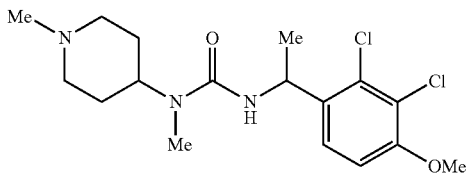 | 3-(1-(2,3-dichloro-4-methoxyphenyl)ethyl)-1-methyl-1-(1-methylpiperidin-4-yl)urea, |
| GA198 | 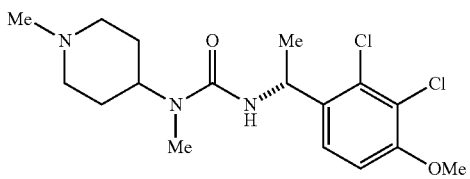 | (R)-3-(1-(2,3-dichloro-4-methoxyphenyl)ethyl)-1-methyl-1-(1-methylpiperidin-4-yl)urea, |

| | | |
|---|---|---|
| GA199 | 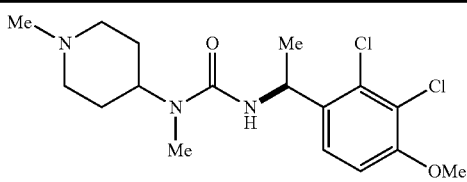 | (S)-3-(1-(2,3-dichloro-4-methoxyphenyl)ethyl)-1-methyl-1-(1-methylpiperidin-4-yl)urea, |
| GA200 | 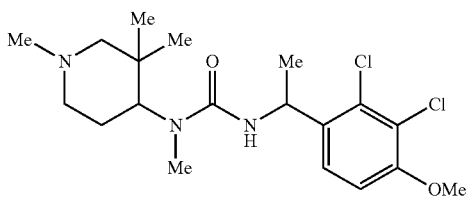 | 3-(1-(2,3-dichloro-4-methoxyphenyl)ethyl)-1-methyl-1-(1,3,3-trimethylpiperidin-4-yl)urea, |
| GA201 | 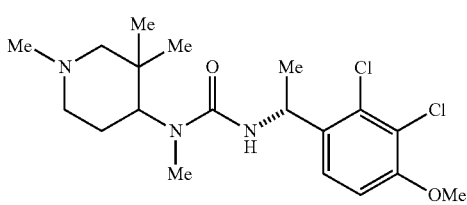 | 3-((R)-1-(2,3-dichloro-4-methoxyphenyl)ethyl)-1-methyl-1-(1,3,3-trimethylpiperidin-4-yl)urea, |
| GA202 | 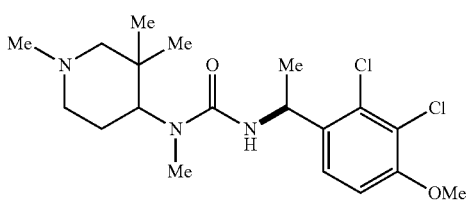 | 3-((S)-1-(2,3-dichloro-4-methoxyphenyl)ethyl)-1-methyl-1-(1,3,3-trimethylpiperidin-4-yl)urea, and |
| GA203 | 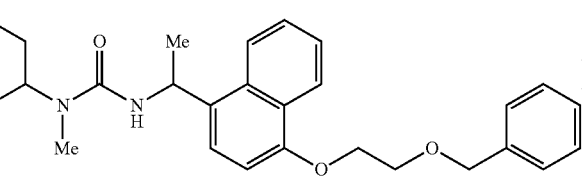 | 3-(1-(4-(2-(benzyloxy)ethoxy)naphthalen-1-yl)ethyl)-1-methyl-1-(1-methylpiperidin-4-yl)urea. |

16. A pharmaceutical composition comprising a therapeutically effective amount of a compound according to claim 1, and one or more pharmaceutically acceptable excipients.

17. 3-(1-(2,3-dichloro-4-methoxyphenyl)ethyl)-1-methyl-1-(1,3,3-trimethylpiperidin-4-yl)urea (GA23), or a pharmaceutically acceptable salt thereof.

18. 1-hydroxy-3-(1-(4-methoxynaphthalen-1-yl)ethyl)-1-(1-methylpiperidin-4-yl)urea (GA168), or a pharmaceutically acceptable salt thereof.

19. 3-(1-(2,3-dichloro-4-methoxyphenyl)ethyl)-1-hydroxy-1-(1-methylpiperidin-4-yl)urea (GA180), or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 8,658,797 B2 | Page 1 of 1 |
| APPLICATION NO. | : 13/404165 | |
| DATED | : February 25, 2014 | |
| INVENTOR(S) | : Silvina Garcia Rubio et al. | |

It is certified that error appears in the above-identified patent and that said Letters Patent is hereby corrected as shown below:

Title Page 1, following item (65) and the publication data, Insert

--Foreign Application Priority Data

February 25, 2011  (CN) .................. PCT/CN2011/000298--

Signed and Sealed this
Seventeenth Day of June, 2014

Michelle K. Lee
*Deputy Director of the United States Patent and Trademark Office*